US 7,951,791 B2

(12) United States Patent
Schrimpf et al.

(10) Patent No.: US 7,951,791 B2
(45) Date of Patent: May 31, 2011

(54) AMINO-SUBSTITUTED TRICYCLIC DERIVATIVES AND METHODS OF USE

(75) Inventors: Michael R. Schrimpf, Grayslake, IL (US); Kevin B. Sippy, Antioch, IL (US); Jianguo Ji, Libertyville, IL (US); Tao Li, Grayslake, IL (US); Jennifer M. Frost, Grayslake, IL (US); Clark A. Briggs, Libertyville, IL (US); William H. Bunnelle, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 39 days.

(21) Appl. No.: 12/046,599

(22) Filed: Mar. 12, 2008

(65) Prior Publication Data

US 2008/0161281 A1    Jul. 3, 2008

Related U.S. Application Data

(63) Continuation of application No. 11/051,437, filed on Feb. 4, 2005, now Pat. No. 7,365,193.

(60) Provisional application No. 60/541,651, filed on Feb. 4, 2004.

(51) Int. Cl.
| | |
|---|---|
| *A01N 43/00* | (2006.01) |
| *A01N 43/62* | (2006.01) |
| *A61K 31/33* | (2006.01) |
| *C07D 245/00* | (2006.01) |
| *C07D 487/00* | (2006.01) |
| *C07D 243/00* | (2006.01) |
| *C07D 491/00* | (2006.01) |
| *C07D 498/00* | (2006.01) |

(52) U.S. Cl. ......... 514/183; 514/221; 540/473; 540/555
(58) Field of Classification Search ................. None
See application file for complete search history.

(56) References Cited

U.S. PATENT DOCUMENTS

| | | | | |
|---|---|---|---|---|
| 2,656,357 | A | 10/1953 | Kushner | |
| 3,838,131 | A | 9/1974 | Gauthier | 260/286 |
| 3,838,134 | A | 9/1974 | Gauthier | 260/286 |
| 3,932,643 | A | 1/1976 | Gauthier | 424/258 |
| 4,059,702 | A | 11/1977 | Meyer | 424/248.55 |
| 4,169,897 | A | 10/1979 | Meyer et al. | 424/330 |
| 6,004,959 | A | 12/1999 | Jones et al. | 514/238.8 |
| 6,379,590 | B1 | 4/2002 | Wu et al. | 252/582 |

FOREIGN PATENT DOCUMENTS

| | | |
|---|---|---|
| JP | 06228094 | 8/1994 |
| JP | 08134067 | 5/1996 |
| JP | 10101591 | 4/1998 |
| JP | 11217348 | 8/1999 |
| WO | 93/15073 | 8/1993 |
| WO | 95/00468 | 1/1995 |
| WO | 96/26938 | 9/1996 |
| WO | 97/45397 | 12/1997 |
| WO | 00/10990 | 3/2000 |
| WO | 00/44755 | 8/2000 |
| WO | 00/66586 | 11/2000 |
| WO | 01/07409 | 2/2001 |
| WO | 01/44243 | 6/2001 |
| WO | 01/51479 | 7/2001 |
| WO | 02/02564 | 1/2002 |
| WO | 02/44183 | 6/2002 |
| WO | 02/096911 | 12/2002 |
| WO | 02/100857 | 12/2002 |
| WO | 03/070732 | 8/2003 |
| WO | 2004/016608 | 2/2004 |
| WO | 2004/113334 | 12/2004 |

OTHER PUBLICATIONS

Abadi, A.H., et al., "Synthesis, antitumor, and antitubercular evaluation of certain new xanthenone and acridinone analogs", *Chem Abstr. Serv.*, Database Acc. #: 1999:225991.

Adams et al., "Development of α7 nicotinic cholinergic receptor in rat hippocampal formation," Developmental Brain Research 139:175-187 (2002).

Adler et al, "Schizophrenia, sensory gating, and nicotinic receptors," Schizophrenia Bulletin 24(2):189-202 (1998).

Albrecht et al., "Bis-basic-substituted polycyclic aromatic compounds. A new class of antiviral agents.[1-3] 8. Bis-basic derivatives of carbazole, dibenzofuran, and dibenzothiophene," J. Med. Chem. 20(3):364-371 (1977).

Albrecht et al., "Bis-basic-substituted polycyclic aromatic compounds. A new class of antiviral agents.[1-4] 3. 2,7-bi (aminoacyl)flurenes and—fluorenones," J. Med. Chem. 17(8):886-889 (1974).

Anderson et al, "Palladium-catalyzed amination of aryl nonaflates," J. Org. Chem.. 68(25):9563-9573 (2003).

(Continued)

*Primary Examiner* — Noble Jarrell
(74) *Attorney, Agent, or Firm* — Antonia M. Holland

(57) ABSTRACT

Compounds of formula (I)

(I)

wherein A and B are amine-substituted sidechains, $Y^1$ and $Y^2$ form various tricyclic cores, $X^a$ and $X^b$ are C, CH, or N, as defined herein, and $R^x$ is an optional substituent. Compounds and compositions of formula (I) are contemplated as well as methods for treating conditions or disorders prevented by or ameliorated by α7 nAChR ligands that encompass compounds of formula (I) and other tricyclic derivatives. Methods of using amino-substituted tricyclic derivatives also are described herein.

4 Claims, No Drawings

OTHER PUBLICATIONS

Andrews et al., "Bis-basic-substituted polycyclic aromatic compounds. A new class of antiviral agents.[1,2] 2. Tilorone and related bis-basic ethers of fluorennone, fluorenol, and fluorene," J. Med. Chem. 17(8):882-886 (1974).

Baron, "Cigarette smoking and Parkinson's Disease" Neurology, 36:1490-1496 (Nov. 1986).

Burke et al., "New synthetic pathways to tilorone hydrochloride," Synth. Commun. 6:371-376 (1976).

Burke et al., "New synthetic routes to tilorone dihydrochloride and some of its analogues," Journal of Medicinal Chemistry 21(10):1084-1086 (1978).

Campo et al., "Synthesis of fluoren-9-ones y the palladium-catalyzed cyclocarbonylation of o-halobiaryls," J. Org. Chem. 67:5616-5620 (2002).

Cappelli, A., et al., "Novel Potent and Selective Central 5-HT3 Receptor Ligands Provided with Different Intrinsic Efficacy. 1. Mapping the Central 5-HT3 Receptor Binding Site by Arylpiperazine Derivatives", Chem. Abst. Serv., Database acc. #:1998:85302.

Carr et al., "Bis-basic-substituted polycyclic aromatic compounds. A new class of antiviral agents.[1,2] 7. Bisalkamine esters of 9-oxoxanthene-2,7-dicarboxylic acid, 3,6-bis-basic ethers of xanthen-9-one, and 2,7-bis(aminoacyl)xanthen-9-ones,-xanthenes, and—thioxanthenes" J. Med. Chem. 19(9):1142-1148 (1976).

Ciske et al., "An efficient synthesis of dihydroxyfluorenones via in situ Pd(0)-catalyzed cross-coupling," Synthesis 1195-1198 (1998).

Coe et al., "Convenient preparation of n-substituted I doles by modified leimgruber-batcho indole synthesis," Tetrahedron Letters 37(34):6045-6048 (1996).

Cordero-Erausquin et al., "Tonic nicotinic modulation of serotoninergic transmission in the spinal cord," PNAS 98(5):2803-2807 (2001).

Dannhardt, et al., "Studies on the Preparation of 5-(β-aminoethyl)-thioisoxazoles" Chimiker-Zeitung, 113(3):109-113 (1989).

Dulenko, V.I., et al., "Recyclization of indolo [2,3-c]pyrylium salts by secondary amines", Chem. Abstr. Serv., Database acc. #:1990:591297.

Ebeid, F.A., et al., "Preliminary study of antischistosomal activity of new synthetic compounds", Rec. Res. Devel. Chem. Pharm. Sci. ,2:237-252 (2002).

El-Shemy, K.R., et al., "Synthesis of 6-substituted-5H[1] benzothiopyrano (2,3,b)pyridin-5-one derivatives as potential schistosomicidal agents", Chem. Abstr. Serv., Database acc. #: 2002-679159.

Falk et al., "Higher expression of α7 nicotinic acetylcholine receptors in human fetal compared to adult brain," Developmental Brain Research 142:151-160 (2003).

Familioni et al., "Intramolecular anionic friedel-crafts equivalents. A general regiospecific route to substituted and naturally occurring xanthen-9-ones," Synlett. 1081-1083 (1997).

Friedman et al., "A double blind placebo controlled trial of donepezil adjunctive treatment to risperidone for the cognitive impairment of schizophrenia," Biol. Psychiatry 51:349-357 (2002).

Fu et al., "Remote aromatic metalation. An anionic friedel-crafts equivalent for the regioselective synthesis of condensed fluorenones from biaryl and m-teraryl 2-amides,"J. Org. Chem. 56:1683 (1991).

Fujioka, H., et al., "Activities of new acridone alkaloid derivatives against Plasmodium yoelii in vitro", Chem. Abstr. Serv., Database acc. #: 1991:3311.

Furuta, Y., et al., "Preparation of 6-heterocyclyl-9,10-dihydro-9-acridinone derivatives and their nigrogen-containing tri- and tetracyclic analogs as antiviral agents", Chem. Abstr. Serv., Database acc. #:1999:468342.

Glatzhofer et al., "Conversion of n-aromatic amides to o-aromatic esters," Organic Letters 4(14):2349-2352 (2002).

Goerdeler, et al., "Synthese Von 5-Chlor-1,2,4-Thiodiazolen Laus Perchlormethylmercaptan Und Amidinen" Eingegangen am 14:182-187 (Nov. 1956).

Gobbi et al., "Synthesis and antitumor activity of new derivatives of xanthen-9-one-4-acetic acid," J. Med. Chem. 45:4931-4939 (2002).

Grisar et al., "Bis-basic-substituted polycyclic aromatic compounds. A new class of antiviral agents. [1,2] 4. Bis-basic sulfonamides of anthraquinone," J. Med. Chem. 17(8):890-893 (1974).

Hallberg, A., et al., "1,2-Didehydrophenothiazines: preparation of 1-alkyl and 1-aryl-substituted phenothiazines by lithium-directed alkylation", Chem. Abstr. Serv., Database acc. #: 1985:487825.

Hartman, P.E., et al., "Microsomal activation to mutagens of antischistosomal methyl thioxanthenones and initial tests on a possibly nonmutagenic analog", Chem. Abstr. Serv., Database acc. #:1975:133025.

Heeschen et al., "Nicotine stimulates angiogenesis and promotes tumor growth and athersclerosis," Nature Medicine 7(7):833-839 (2001).

Heeschen et al., "A novel angiogenic pathway mediated by non-neuronal nicotinic acetycholine receptors," Journal of Clinical investigation 110(4):527-536 (2002).

Hori, M., et al., "10-Thiaanthracenes. III. Synthesis of 10-phenyl-10-thiaanthracenes having a basic group at the position1", Chem. Abstr. Serv., Database acc. #: 1975:496952.

IUPAC 1974 Recommendations for Section E, Fundamental Stereochemistry, Pure Appl. Chem. 45:13-30 (1976).

Jacobi et al., "Nicotine accelerates angiogenesis and would healing in genetically diabetic mice," American Journal of Pathology 161:97-104 (2002).

Jantzen and Robinson, Modern Pharmaceutics, 596, (1996).

Jones, D.H., Phenothiazynes: preparation of 2- and 3-tertiary aminophenothiazines, Chem. Abstr. Serv., Database acc. #: 1971:53694.

Jonnala et al., "Relationship between the increased cell surface α7 nicotinic receptor expression and neuroprotection induced by several nicotinic receptor agonists," Journal of Neuroscience Research 66:565-572 (2001).

Kihara et al., "α7 nicotinic receptor transduces signals to phosphatidylinositol 3-kinase to block A β-amyloid-induced neurotoxicity," Journal of Biological Chemistry 276(17):13541-13546 (2001).

Kmonicek, V., et al., "Synthesis of potential neuroleptics and tranquillizers: 2-(tert-amino)-9-[3-(dimethylamino)propylidene] thioxanthenes", Chem. Abstr. Serv., Database acc. #:1987:49969.

Kryska et al., "Improved, acid-catalyzed iodinating procedures for activated aromatics with (diacetoxyiodo)benzene as the oxidant," J. Chem. Research. (S) 590-591 (1999).

Kym et al., "Bisphenolic compounds that enhance cell cation transport are found in commercial phenol red," J. Med. Chem. 39:4897-4904 (1996).

Leonard et al., "Smoking and schizophrenia: abnormal nicotinic receptor expression," European Journal of Pharmacology 393:237-242 (2000).

Levin, "Nicotinic receptor subtypes and cognitive function," J. Neurobiol. 53:633-640 (2002).

Ley et al., "Modern synthetic methods for copper-mediated C(aryl)-O, C(aryl)-N, and C(aryl)-S bond formation," Angew. Chem. Int. Ed. 42:5400-5449 (2003).

Liu et al., "β-Amyloid peptide blocks the response of α7-containing nicotinic receptors on hippocampal neurons," PNAS 98(8):4734-4739 (2001).

Lynch et al., "Efficient asymmetric synthesis of ABT-594; a potent, orally effective analgesic," Tetrahedron Asymmetry 9:2791-2794 (1998).

Mari, S., et al., "Flavone and xanthone derivatives related to fluoroquinolones", Chem. Abstr. Serv., Database acc. #: 1999:470681.

Menkovic, et al., Phytochemistry, 61:415-420 (2002).

Muci et al., "Practical palladium catalysts for C—N and C—O bond formation," Topics Current Chem. 219:131-209 (2002).

Olah et al., Nafion-H catalysed intramolecular friedel-crafts acylation: formation of cyclic ketones and related heterocycles,: Synlett. 7:1067-1068 (1999).

Pabreza et al., "[3H]cytosine binding to nicotinic cholingergic receptors in brain," Mol. Pharm. 39:9-12 (1991).

Pedro, et al., Bioorganic and Medicinal Chemistry, 10:3725-3730 (2002).

Perry et al., "2,7-disubstituted amidofluorenone derivatives as inhibitors of human telomerase," J. Med. Chem. 42:2679-2684 (1999).

Pirrung et al., "Photochmically removable silyl protecting groups," J. Am. Chem. Soc. 123:3638-3643 (2001).

Poste, et al., Methods in Cell Biology, vol. XIV, Academic Press, New York, NY, 33 et seq. (1976).

Protiva, M., et al., "Antimicrobial 1-(2-fluorenyl)-piperazines", Chem, Abstr. Serv., Database 1981:192373.

Protiva, M., et al.. "Preparation of 2-(tertiary amino)-9-(3-dimethylaminopropylidene)thio xanthenes and their salts as antimicrobials and tranquilizers", Chem. Abstr. Serv., Database Acc. #: 1989:439190.

Radl, S., Preparation of 1-hydroxyxanthen-9(9H)-ones and 1-hydroxyacridin-9(10H)-ones via corresponding 3,4-dihydro-1,9(2H)-diones, Chem. Abstr. Serv., Database acc. #:1996:123342.

Rowley et al., "Current and novel approaches to the drug treatment of schizophrenia," Journal of Medicinal Chemistry 44(4):477-501 (2001).

Rudorf, W.D., "Product class 7: benzothiopyrylium salts", Chem. Abstr. Serv.,Database acc. No. 2003-807797.

Sharp. T.M., "New Synthesis of lucanthone (miracil D, nilodin)", Chem. Abstr. Serv., Database acc. #1952:54608.

Sawa et al., "Schizophrenia: neural mechanisms for novel therapies," Mol. Med. 9:3-9 (2003).

Shimohama et al., "Nicotinic $\alpha 7$ receptors protect against glutamate neurotoxicity and neuronal ischemic damage," Brain Research 779:359-363 (1998).

Sill et al., "Bis-basic-substituted polycyclic aromatic compounds. A new class of antiviral agents. 1. Bisalkamine esters of fluorenone-, fluorenol-, and fluorenedicarboxylic acids," J. Med. Chem. 16(3):240-245 (1973).

Son et al., "Evidence suggesting that the mouse sperm acrosome reaction initiated by the zona pellucida involves an $\alpha 7$ nicotinic acetylcholine receptor," Biology of Reproduction 68:1348-1351 (2003).

Stevens et al., "Selective $\alpha_7$-nicotinic agonists normalize inhibition of auditory response in DBA mice," Psychopharmacology 136:320-327 (1998).

Tabarrini, O., et al., "Design and Synthesis of Modified Quinolones as Antitumoral Acridones", J. Med. Chem., 42:2136-2144 (1999).

Ting et al., "The synthesis of substituted fluorenes as novel non-imidazole histamine $H_3$ inhibitors," Bioorganic & Medicinal Chemistry Letters 12:2643-2646 (2002).

Torii et al., "A versatile cycloaddition for the generation of pyrrolidine derivatives via C—N—C 1,3-dipoles," Chemistry Letters 747-748 (1996).

Toyoshima, S., et al., "Anthelmintic piperazine salts", Chem. Abstr. Serv., Database acc. #1964:60965.

Tsuneki et al., "Mouse muscle denervation increases expression of an $\alpha 7$ nicotinic recptor with unusual pharmacology," J. Physiol. (London) 547:169-179 (2003).

Tsunoda et al., "1,1'-(Azoclicarbonyl)dipiperidine-tributylphosphine, a new reagent system for mitsunobu reaction," Tetrahedron Letters 34(10):1639-1642 (1993).

Tunoori et al., "Polymer-bound triphenylphosphine as traceless reagent for mitsunobu reactions in combinatorial chemistry: synthesis of aryl ethers from phenols and alcohols," Tedrahedron Letters 39:8751-8754 (1998).

Valenta, V., et al., "Neurotropic and psychotropic agents. XCVII. Synthesis of some 1-(2-fluorenyl)piperazines", Chem. Abstr. Serv., Database acc. #: 1976:592663.

Wang et al., "Nicotinic acetylcholine receptor $\alpha 7$ subunit is an essential regulator of inflammation," Nature 421:384-388 (2003).

Wolff, M. Burger's Medicinal Chemistry and Drug Discovery, 975-977 (1995).

Davies, R.R., et al., "Indazole Derivatives: The synthesis of various amino-and hydroxy-indazoles and derived sulphonic acids," J. Chem. Soc. Abstract 1565 (1955).

Prescott, D.M., Ed. "Methods in cell biology," vol. XIV, Academic Press, New York, NY 33 et seq. (1976).

Hughes, D.L., "The Mitsunobu Reaction," Chapter 2, Department of Process Research, Merck Sharp and Dohme Research Laboratories, Merck and Co., Inc., Rahway, NJ; "Organic Reactions," vol. 42, Published by John Wiley & Sons, Inc., 1992.

De La Llosa, M.J., et al., "No. 254—Ill. Systematic degradation of peptides by reduction of their N, nitro-2 methanesulfonyl-4 phenyl derivatives," Laboratoire de Morphologie Experimentale et Endocrinologie, College de France, Paris; Istituto di Chimica Organica dell 'Universita, Padova, Italy (Manuscrit received Jun. 25 60). (English Translation).

AMINO-SUBSTITUTED TRICYCLIC DERIVATIVES AND METHODS OF USE

This application is a continuation application of the U.S. application Ser. No. 11/051,437, filed Feb. 4, 2005, which claims priority from the U.S. Provisional Patent Application Ser. No. 60/541,651, filed Feb. 4, 2004, which are hereby incorporated by reference in entirety.

BACKGROUND OF THE INVENTION

1. Technical Field

The invention relates to amine-substituted tricyclic derivatives, compositions comprising such compounds, and methods of treating conditions and disorders using such compounds and compositions.

2. Description of Related Technology

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of the nAChR exist in the CNS and periphery. Each subtype has a different effect on regulating the overall physiological function.

Typically, nAChRs are ion channels that are constructed from a pentameric assembly of subunit proteins. At least 12 subunit proteins, $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is comprised of homomeric $(\alpha 7)_5$ (the $\alpha 7$ subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha 7$ nAChRs have been shown to play a significant role in enhancing cognitive function, including aspects of learning, memory and attention (Levin, E. D., J. Neurobiol. 53: 633-640, 2002). For example, $\alpha 7$ nAChRs have been linked to conditions and disorders related to attention deficit disorder, attention deficit hyperactivity disorder (ADHD), Alzheimer's disease (AD), mild cognitive impairment, senile dementia, dementia associated with Lewy bodies, dementia associated with Down's syndrome, AIDS dementia, Pick's Disease, as well as cognitive deficits associated with schizophrenia, among other systemic activities.

The activity at the $\alpha 7$ nAChRs can be modified or regulated by the administration of $\alpha 7$ nAChR ligands. The ligands can exhibit antagonist, agonist, or partial agonist properties. Thus, $\alpha 7$ ligands have potential in treatment of various cognitive disorders.

Although various classes of tricyclic compounds are known, it would be beneficial to provide additional compounds demonstrating activity at the $\alpha 7$ nAChRs that can be incorporated into pharmaceutical compositions useful for therapeutic methods. Specifically, it would be beneficial to provide tricyclic compounds that interact selectively with $\alpha 7$-containing neuronal nAChRs compared to other subtypes.

SUMMARY OF THE INVENTION

The invention is directed to amine-substituted tricyclic derivative compounds as well as compositions comprising such compounds, and method of using the same. Compounds of the invention have the formula (I):

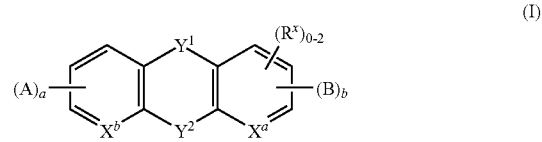

(I)

or a pharmaceutically acceptable salt, ester, amide, or prodrug thereof, wherein:

A and B are each independently selected from the group consisting of hydroxy; halogen; alkoxy; amino; alkylamino; acylamino; dialkylamino; cyano; nitro;
—N(R$^z$)C(=O)(OR$^y$); and
a group of formula (a):

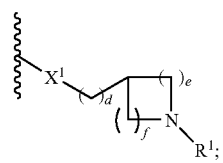

(a)

a group of formula (b):

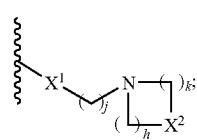

(b)

a group of formula (c):

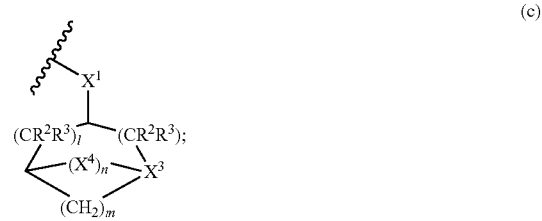

(c)

a group of formula (d):

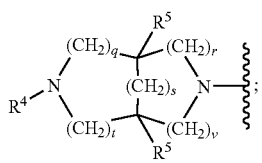

a group of formula (e):

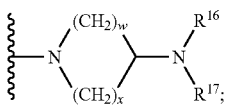

a group of formula (f):

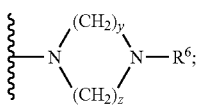

a group of formula (g):

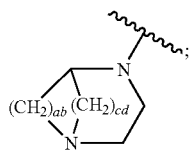

(h) —C≡CCH$_2$NR$^7$R$^8$; and (i) —O—(C(R$^{20a}$R$^{20b}$))$_{2-3}$N(R$^{21}$)(R$^{22}$); provided that at least one of A or B is a group selected from (a)-(i); with the proviso that if A or B is selected from group (a), (b), or (f) when y and z are both two, then A and B are different;

X$^a$ and X$^b$ are each independently selected from the group consisting of C, C(H) and N; provided that when one of X$^a$ and X$^b$ is N, the other is C or C(H);

X$^1$ at each occurrence is selected from the group consisting of O, S, and —N(R$^9$)—;

X$^2$ at each occurrence is selected from the group consisting of O, S, —CH$_2$—, and —N(R$^{10}$)—;

X$^3$ is C(H) or N;

X$^4$ is CH$_2$ or N(R$^{13}$); provided that when X$^3$ is N, X$^4$ is CH$_2$ or when X$^4$ is N(R$^{13}$), X$^3$ is C(H);

Y$^1$ is independently selected from the group consisting of —C(O)—, —CH$_2$—, —CH(OH)—, —C(S)—, —N(R$^{11}$)—, —O—, —S—, —S(O)—, —S(O)$_2$—, —C(O)NH—, and —S(O)$_2$NH—, provided that if Y$^1$ is —C(O)—, —O—, —S—, or —N(R$^{11}$)— and one of A or B is selected from a group (a), (b), or (f), then the other of A or B is selected from the group consisting of dialkylamino and cyano;

Y$^2$ is a bond or Y$^2$ is independently selected from —O—, —S—, and —N(R$^{12}$)—;

R$^1$ is independently selected from hydrogen and alkyl;

R$^2$ and R$^3$ at each occurrence are each independently selected from the group consisting of hydrogen and alkyl;

R$^4$ and R$^6$ at each occurrence are each independently selected from the group consisting of hydrogen and alkyl;

R$^5$ at each occurrence are each independently selected from the group consisting of hydrogen, alkyl, and alkoxycarbonyl;

R$^7$ and R$^8$ are each independently selected from hydrogen and alkyl or R$^7$ and R$^8$ taken together with the nitrogen atom to which each is attached form a 4- to 8-membered cyclic amine;

R$^9$, R$^{10}$, R$^{11}$, R$^{12}$ and R$^{13}$ at each occurrence are each independently selected from hydrogen and alkyl;

R$^{16}$ and R$^{17}$ are each independently selected from hydrogen and alkyl, or R$^{16}$ and R$^{17}$ taken together with the nitrogen atom to which each is attached form a 4- to 8-membered cyclic amine;

R$^{20a}$ and R$^{20b}$ are each independently selected from the group consisting of hydrogen and alkyl;

R$^{21}$ and R$^{22}$ are each independently selected from the group consisting of hydrogen and alkyl;

R$^x$ is independently selected at each occurrence from the group consisting of halogen, alkoxy, amino, alkylamino, dialkylamino, acylamino, dialkylaminoalkyl, and cyano;

R$^y$ and R$^z$ are each independently selected from the group consisting of hydrogen and alkyl;

a is 0 or 1;

b is 0 or 1; provided that when one of a and b is 0, the other is 1;

d is independently selected from 0 and 1;

e and f are each independently selected from 0, 1, 2, and 3, provided that the sum total of e and f is 2, 3, or 4, provided that when d is 0, e and f are selected from 1, 2, and 3;

j is independently selected from 2 and 3;

h and k are each independently selected from 0, 1, and 2, provided that the sum total of h and k is 2, 3, or 4, provided that when X$^2$ is O, S, or N(R$^{10}$), h and k are both 2;

l is 0 or 1, m is 2 or 3, and n is 0, 1, or 2, provided that the sum total of l, m, and n is 4, 5, or 6;

q, r, s, t, and v are each independently selected from 0, 1, or 2, provided that the sum of q and r; t and v; q, s, and t; and r, s, and v; are each at least 1, and further provided that the sum total of q, r, s, t, and v is 2, 3, 4, or 5, provided that when the sum total is 5 and Y$^1$ is —O—, —S—, or —N(R$^{11}$)— and Y$^2$ is a bond, both A and B are other than hydrogen;

w and x are each independently selected from 1, 2, or 3, provided that the sum total of w and x is 3, 4, 5, or 6;

y and z are each independently selected from 2, 3, or 4, provided that the sum total of y and z is 4, 5, or 6; and ab is 2 or 3, and cd is 1 or 2.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity.

Yet another aspect of the invention relates to a method of selectively modulating to nAChR activity, for example α7 nAChR activity. The method is useful for treating and/or preventing conditions and disorders related to α7 nAChR activity modulation in mammals. More particularly, the method is useful for conditions and disorders related to attention deficit disorder, attention deficit hyperactivity disorder (ADHD), Alzheimer's disease (AD), mild cognitive impairment, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, wound healing, and other complications associated with diabetes, among other systemic activities.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl", as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy", as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino", as used herein, means —$NH_2$.

The term "acylamino", as used herein, means an acyl group, as defined herein, appended to the parent molecular moiety through an amino group, as defined herein.

The term "alkylamino", as used herein, means an alkyl group, as defined herein, appended to the parent molecular moiety through an amino group, as defined herein.

The term "dialkylamino", as used herein, means two independently selected alkyl groups, as defined herein, appended to the parent molecular moiety through an amino group, as defined herein.

The term "dialkylaminoalkyl", as used herein, means a dialkylamino, as defined herein, appended to the parent molecular moiety through an alkyl group, as defined herein.

The term "amido", as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl", as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amino, carboxy, cyano, formyl, haloalkoxy, haloalkyl, halo, hydroxy, hydroxyalkyl, mercapto, nitro, thioalkoxy, —$NR_AR_B$, $(NR_AR_B)$alkyl, $(NR_AR_B)$alkoxy, $(NR_AR_B)$carbonyl, and $(NR_AR_B)$sulfonyl.

The term "carbonyl", as used herein, means a —C(O)— group.

The term "carboxy", as used herein, means a —CO$_2$H group.

The term "cyano", as used herein, means a —CN group.

The term "cyclic amine", as used herein, means a heterocycle group, as defined herein, wherein the heteroatom is nitrogen. Typically, cyclic amine groups are 4- to 6-membered rings containing one nitrogen atom.

The term "formyl", as used herein, means a —C(O)H group.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl" means an aromatic five- or six-membered ring containing 1, 2, 3, or 4 heteroatoms independently selected from nitrogen, oxygen, or sulfur. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridinyl, pyrimidinyl, pyrrolyl, tetrazolyl, thiadiazolyl, thiazolyl, thienyl, triazinyl, and triazolyl.

The heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "heterocycle," as used herein, refers to a four, five, six, seven or eight membered ring containing one, two, or three heteroatoms independently selected from the group consisting of nitrogen, oxygen, and sulfur. The four membered ring has zero double bond and five membered ring has zero or one double bond. The six membered ring has zero, one, or two double bonds. The seven and eight membered rings have zero. one, two, or three double bonds. The term "heterocycle" also includes bicyclic groups in which the heterocycle ring is fused to a phenyl group, a monocyclic cycloalkenyl group, as defined herein, a monocyclic cycloalkyl group, as defined herein, or another monocyclic heterocycle group, as defined herein; and tricyclic groups in which a bicyclic system is fused to a phenyl group, a monocyclic cycloalkenyl group, as defined herein, a monocyclic cycloalkyl group, as defined herein, or another monocyclic heterocycle group. The heterocycle groups of the present invention can be attached to the parent molecular moiety through a carbon atom or a nitrogen atom. Representative examples of heterocycle include, but are not limited to, azetidinyl, azepanyl, azocanyl, morpholinyl, piperazinyl, piperidinyl, pyrrolidinyl, and thiomorpholinyl.

The heterocycles of the present invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halo, hydroxy, hydroxyalkyl, mercapto, nitro, oxo, thioalkoxy, —NR$_A$R$_B$, and (NR$_A$R$_B$)sulfonyl.

The term "heterocycloalkyl", as used herein, refers to a heterocycle group, as defined herein, appended to the parent molecular moiety through an alkyl group, as defined herein. Representative examples of heterocycloalkyl include, but are not limited to, 1-methylpyrrolidin-2-ylmethyl, azetidin-2-ylmethyl, 1-methylazetidin-2-ylmethyl, pyrrolidin-3-ylethyl, and 1-methylpyrrolidin-3-ylethyl.

The term "bicyclic heteroaryl" refers to fused aromatic nine- and ten-membered bicyclic rings containing 1, 2, 3, or 4 heteroatoms independently selected from nitrogen, oxygen, or sulfur, or a tautomer thereof. The bicyclic heteroaryl groups are connected to the parent molecular moiety through a carbon or nitrogen atom. Representative examples of bicyclic heteroaryl rings include, but are not limited to, indolyl, benzothiazolyl, benzofuranyl, isoquinolinyl, and quinolinyl. Bicyclic heteroaryl groups of the invention are substituted with 0, 1, 2, or 3 substituents independently selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkynyl, carboxy, cyano, formyl, haloalkoxy, haloalkyl, halo, hydroxy, hydroxyalkyl, mercapto, nitro, —NR$_A$R$_B$, (NR$_A$R$_B$)alkyl, (NR$_A$R$_B$)alkoxy, (NR$_A$R$_B$)carbonyl, and (NR$_A$R$_B$)sulfonyl.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —NO$_2$ group.

The term "—NR$_A$R$_B$", as used herein, means two groups, R$_A$ and R$_B$, which are appended to the parent molecular moiety through a nitrogen atom. R$_A$ and R$_B$ are each independently hydrogen, alkyl, alkylcarbonyl, or formyl. Representative examples of —NR$_A$R$_B$ include, but are not limited to, amino, methylamino, acetylamino, and acetylmethylamino.

The term "(NR$_A$R$_B$)alkyl", as used herein, means a —NR$_A$R$_B$ group, as defined herein, appended to the parent molecular moiety through an alkyl group, as defined herein. Representative examples of (NR$_A$R$_B$)alkyl include, but are not limited to, (amino)methyl, (dimethylamino)methyl, and (ethylamino)methyl.

The term "(NR$_A$R$_B$)alkoxy", as used herein, means a —NR$_A$R$_B$ group, as defined herein, appended to the parent molecular moiety through an alkoxy group, as defined herein. Representative examples of (NR$_A$R$_B$)alkoxy include, but are not limited to, (amino)methoxy, (dimethylamino)methoxy, and (diethylamino)ethoxy.

The term "(NR$_A$R$_B$)carbonyl", as used herein, means a —NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)sulfonyl", as used herein, means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl, and (ethylmethylamino)sulfonyl.

The term "sulfonyl", as used herein, means a —S(O)$_2$— group.

The term "thioalkoxy", as used herein, means an alkyl group, as defined herein, appended to the parent molecular moiety through a sulfur atom. Representative examples of thioalkoxy include, but are no limited to, methylthio, ethylthio, and propylthio.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

Compounds of the Invention

Compounds of the invention can have the formula (I) as described above.

Preferred moieties for the group of formula (a) are azetidinyloxy, N-methylazetidinyloxy, pyrrolidinyloxy, N-methylpyrrolidinyloxy, piperidinyloxy, N-methyl piperidinyloxy; azetidinylmethoxy, N-methylazetidinyl methoxy, pyrrolidinylmethoxy, N-methylpyrrolidinylmethoxy, piperidinylmethoxy, N-methylpiperidinylmethoxy, and the like.

Specific examples of rings suitable for a group of formula (b) include, but are not limited to,

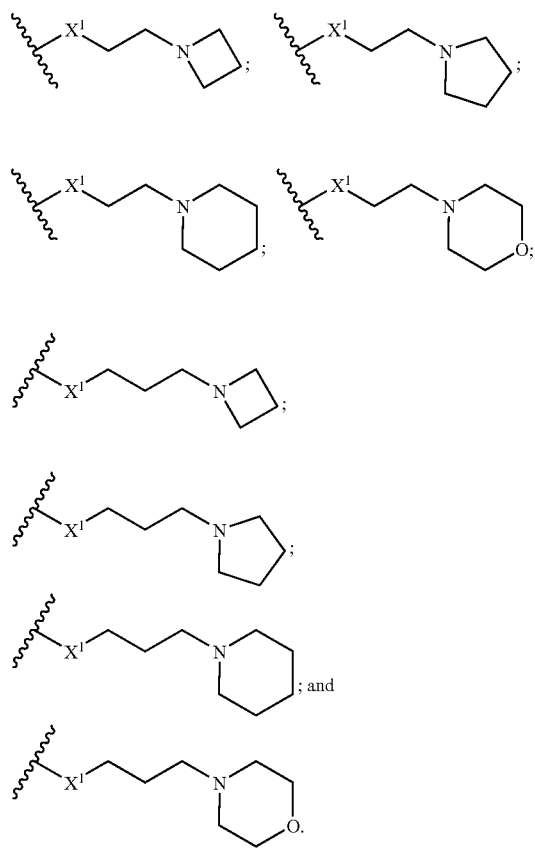

Specific examples of rings suitable for a group of formula (c) include, but are not limited to,

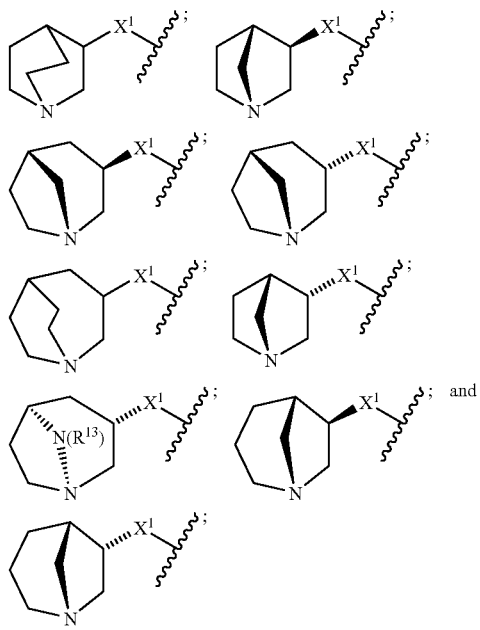

wherein X$^1$ and R$^{13}$ are as defined for compounds of formula (I), and enantiomers thereof. Preferably, X$^1$ is O or NR$^9$, wherein R$^9$ is hydrogen or alkyl. Wherein A and B of formula (I) are a group of formula (c) or one of A and B is a group of formula (c) and the other is halogen when a is 1 and b is 1, or one of A and B is a group of formula (c) when one of a and b is 1 and the other is 0; wherein l is 0 or 1, n is 1 or 2, and m is 2, Y$^1$ is —C(O)—, —CH$_2$—, —S(O)$_2$— or —N(R$^{11}$)—, Y$^2$ is a bond or —O—; R$^{11}$ at each occurrence is independently selected from the group consisting of hydrogen and alkyl; X$^1$ is selected from the group consisting of O and —N(R$^9$)—; R$^2$ and R$^3$ are hydrogen; X$^3$, X$^4$, R$^9$ and R$^{13}$ are as defined in formula (I).

Specific examples of rings suitable for a group of formula (d) include, but are not limited to,

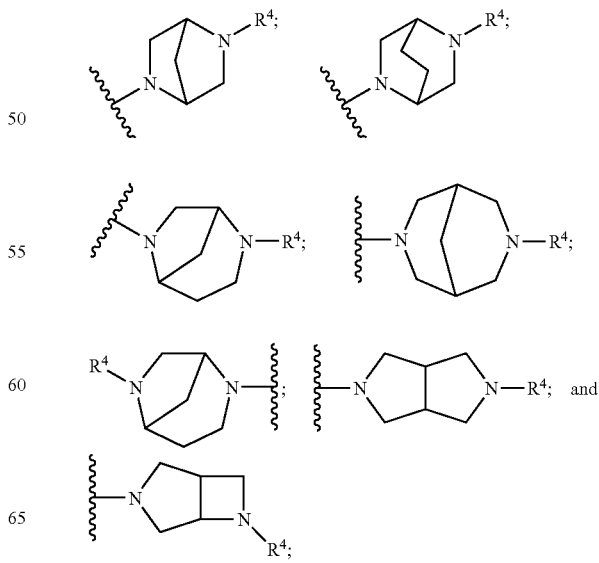

and enantiomers thereof, wherein R⁴ is as defined for compounds of formula (I). Preferably, R⁴ is hydrogen. Wherein one of A or B is selected from a group of formula (d), it can be particularly beneficial if the other of A or B is a group selected from bromo, hydroxy, amino, dialkylamino, acylamino, and —N(H)C(=O)(OCH₃) when both a and b are 1. Particularly, it is preferred that the group of formula (d) is

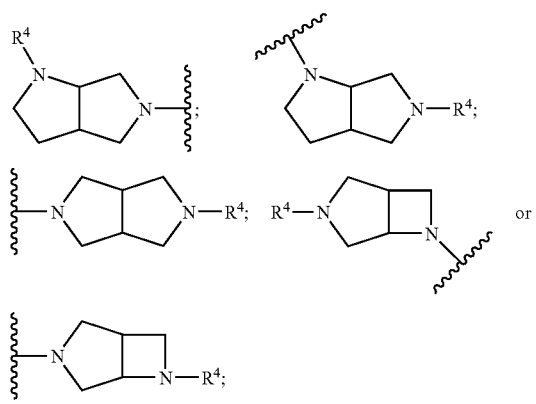

wherein R⁴ is hydrogen or alkyl. More particularly, it can be beneficial that the one of A or B is a group of formula (d) and the other is amino.

Specific examples of rings suitable for a group of formula (e) include, but are not limited to,

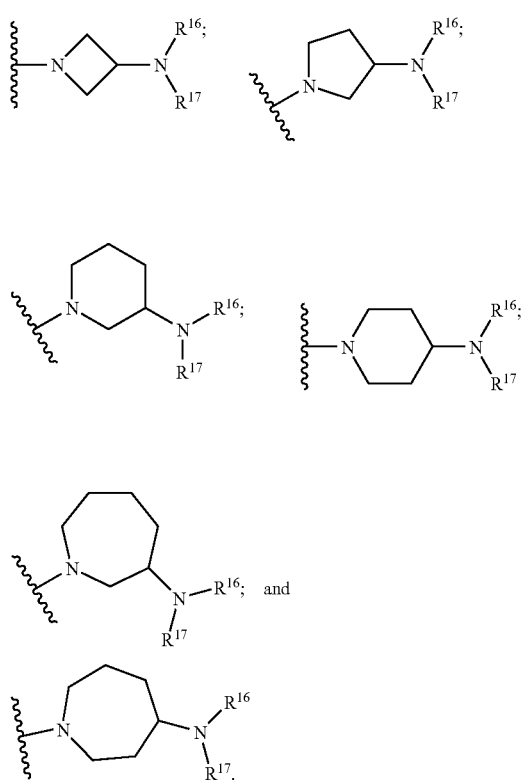

wherein R¹⁶ and R¹⁷ are as defined for compounds of formula (I); and enantiomers thereof.

Specific examples of rings suitable for a group of formula (f) include, but are not limited to,

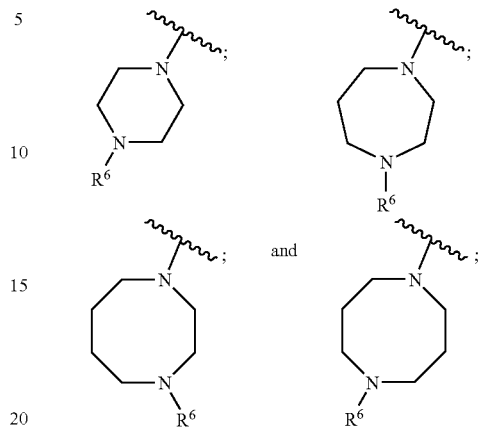

and enantiomers thereof, wherein R⁶ is as defined for compounds of formula (I).

Specific examples of rings suitable for a group of formula (g) include, but are not limited to,

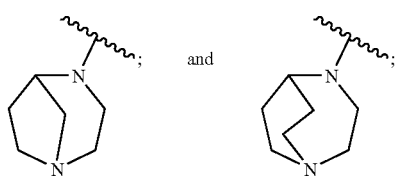

and enantiomers thereof.

Specific compounds of formula (I) contemplated as part of the invention include, but are not limited to:
2,7-bis-[(3R)-1-azabicyclo[2.2.2]octan-3-yloxy]-fluoren-9-one;
2,7-bis[(3S)-1-azabicyclo[2.2.2]octan-3-yloxy]-fluoren-9-one;
2-[(3R)-1-azabicyclo[2.2.2]octan-3-yloxy]-fluoren-9-one;
2-[(3S)-1-azabicyclo[2.2.2]octan-3-yloxy]-fluoren-9-one;
2,7-bis(4-methyl-[1,4]diazepan-1-yl)-fluoren-9-one;
2,7-bis[3,7-diazabicyclo[3.3.0]octan-3-yl]-fluoren-9-one;
2,7-bis[7-methyl-3,7-diazabicyclo[3.3.0]octan-3-yl]fluoren-9-one;
2-[3,7-diazabicyclo[3.3.0]octan-3-yl]-fluoren-9-one;
2-[7-methyl-3,7-diazabicyclo[3.3.0]octan-3-yl]-fluoren-9-one;
2,7-bis(3-diethylamino-propyn-1-yl)-fluoren-9-one;
3,7-bis(2-diethylaminoethoxy)dibenzothiophene;
3,7-bis(2-diethylaminoethoxy)dibenzothiophene-5-oxide;
3,7-bis[(3S)-1-azabicyclo[2.2.2]octan-3-yloxy]-dibenzothiophene;
2-[(1S,5S)-3,6-diazabicyclo[3.2.0]heptan-3-yl]-dibenzothiophene-5,5-dioxide;
2-amino-7-[3,7-diazabicyclo[3.3.0]octan-3-yl]-fluoren-9-one;
2-[(3R)-1-azabicyclo[2.2.2]octan-3-yloxy]-xanthen-9-one;
2-(1-azabicyclo[2.2.2]octan-3-yloxy)-9H-carbazole;
2-(3,7-diazabicyclo[3.3.0]octan-3-yl)-7-methylamino-fluoren-9-one;
2-(3,7-diazabicyclo[3.3.0]octan-3-yl)-7-dimethylamino-fluoren-9-one;

2-amino-7-(7-methyl-3,7-diazabicyclo[3.3.0]octan-3-yl)-fluoren-9-one;
2-methylamino-7-(7-methyl-3,7-diazabicyclo[3.3.0]octan-3-yl)-fluoren-9-one;
2-dimethylamino-7-(7-methyl-3,7-diazabicyclo[3.3.0]octan-3-yl)-fluoren-9-one;
2-(3,7-diazabicyclo[3.3.0]octan-3-yl)-xanthen-9-one;
2-(7-methyl-3,7-diazabicyclo[3.3.0]octan-3-yl)-xanthen-9-one;
2-amino-7-(3,7-diazabicyclo[3.3.0]octan-3-yl)-xanthen-9-one;
2-amino-7-(7-methyl-3,7-diazabicyclo[3.3.0]octan-3-yl)-xanthen-9-one;
2-(3,7-diazabicyclo[3.3.0]octan-3-yl)-7-methylamino-xanthen-9-one;
2-methylamino-7-(7-methyl-3,7-diazabicyclo[3.3.0]octan-3-yl)-xanthen-9-one;
2-(3,7-diazabicyclo[3.3.0]octan-3-yl)-7-dimethylamino-xanthen-9-one;
2-dimethylamino-7-(7-methyl-3,7-diazabicyclo[3.3.0]octan-3-yl)-xanthen-9-one;
2-amino-7-[(3R)-1-azabicyclo[2.2.2]oct-3-yloxy]-fluoren-9-one;
2-amino-7-[(3S)-1-azabicyclo[2.2.2]oct-3-yloxy]-fluoren-9-one;
2-[(3R)-1-azabicyclo[2.2.2]oct-3-yloxy]-7-methylamino-fluoren-9-one;
2-[(3S)-1-azabicyclo[2.2.2]oct-3-yloxy]-7-methylamino-fluoren-9-one;
2-[(3R)-1-azabicyclo[2.2.2]oct-3-yloxy]-7-dimethylamino-fluoren-9-one;
2-[(3S)-1-azabicyclo[2.2.2]oct-3-yloxy]-7-dimethylamino-fluoren-9-one;
3,7-bis[(3R)-1-azabicyclo[2.2.2]octan-3-yloxy]-dibenzothiophene;
3,7-bis[(3S)-1-azabicyclo[2.2.2]octan-3-yloxy]-dibenzothiophene-5,5-dioxide;
3,7-bis[(3R)-1-azabicyclo[2.2.2]octan-3-yloxy]-dibenzothiophene-5,5-dioxide;
3,7-bis[3,7-diazabicyclo[3.3.0]octan-3-yl]-dibenzothiophene-5,5-dioxide;
3,7-bis[7-methyl-3,7-diazabicyclo[3.3.0]octan-3-yl]-dibenzothiophene-5,5-dioxide;
3-[3,7-diazabicyclo[3.3.0]octan-3-yl]-dibenzothiophene-5,5-dioxide;
3-[7-methyl-3,7-diazabicyclo[3.3.0]octan-3-yl]-dibenzothiophene-5,5-dioxide;
3-amino-7-[3,7-diazabicyclo[3.3.0]octan-3-yl]-dibenzothiophene-5,5-dioxide;
2-[(3S)-1-azabicyclo[2.2.2]octan-3-yloxy]-xanthen-9-one;
2,7-bis-(8-methyl-8-aza-bicyclo[3.2.1]oct-3-yloxy)-fluoren-9-one;
2,7-bis-[(1S,5S)-3,6-diazabicyclo[3.2.0]hept-3-yl]-fluoren-9-one;
2,7-bis-[(1S,5S)-6-methyl-3,6-diazabicyclo[3.2.0]hept-3-yl]-fluoren-9-one;
2,7-bis-[(1R,5R)-6-methyl-3,6-diazabicyclo[3.2.0]hept-3-yl]-fluoren-9-one;
2,7-bis-[(S)-3-dimethylaminopyrrolidin-1-yl]-fluoren-9-one;
{3-[7-(3-diethylaminoprop-1-ynyl)-5,5-dioxo-5H-5$\lambda^6$-dibenzothiophen-3-yl]-prop-2-ynyl}-diethylamine;
2,7-bis-[3,7-diazabicyclo[3.3.0]octan-3-yl]-dibenzothiophene-5,5-dioxide;
2-[(S)-pyrrolidin-3-yloxy]-fluoren-9-one;
2-[(S)-1-methylpyrrolidin-3-yloxy]-fluoren-9-one;
2-(piperidin-4-yloxy)-fluoren-9-one;
2-(1-azabicyclo[2.2.2]oct-3-ylamino)-fluoren-9-one;
2-[(1R,5R)-6-methyl-3,6-diazabicyclo[3.2.0]hept-3-yl]-fluoren-9-one;
2-[(1S,5S)-3,6-diazabicyclo[3.2.0]hept-3-yl]-fluoren-9-one;
2-[(1S,5S)-6-methyl-3,6-diazabicyclo[3.2.0]hept-3-yl]-fluoren-9-one;
2-(1,4-diazabicyclo[3.2.2]non-4-yl)-fluoren-9-one;
2-(9H-fluoren-2-yl)-octahydropyrrolo[3,4-c]pyrrole;
(1-azabicyclo[2.2.2]oct-3-yl)-(9H-fluoren-2-yl)-amine;
(R)-3-(9H-fluoren-2-yloxy)-1-azabicyclo[2.2.2]octane;
(S)-3-(9H-fluoren-2-yloxy)-1-azabicyclo[2.2.2]octane;
(R)-3-(5,5-dioxo-5H-5$\lambda^6$-dibenzothiophen-3-yloxy)-1-azabicyclo[2.2.2]octane;
(S)-3-(5,5-dioxo-5H-5$\lambda^6$-dibenzothiophen-3-yloxy)-1-azabicyclo[2.2.2]octane;
1-(5,5-dioxo-5H-5$\lambda^6$-dibenzothiophen-3-yl)-4-methylpiperazine;
(1S,5S)-3-(5,5-dioxo-5H-5$\lambda^6$-dibenzothiophen-3-yl)-3,6-diazabicyclo[3.2.0]heptane;
(1S,5S)-3-(5,5-dioxo-5H-5$\lambda^6$-dibenzothiophen-3-yl)-6-methyl-3,6-diazabicyclo[3.2.0]heptane;
4-(5,5-dioxo-5H-5$\lambda^6$-dibenzothiophen-3-yl)-1,4-diazabicyclo[3.2.2]nonane;
(S)-2-(1-azabicyclo[2.2.2]oct-3-yloxy)-xanthen-9-one;
2-(3,7-diazabicyclo[3.3.0]oct-3-yl)-xanthen-9-one;
2-(7-methyl-3,7-diazabicyclo[3.3.0]oct-3-yl)-xanthen-9-one;
2-(2-diethylaminoethoxy)-7-(3-diethylaminoprop-1-ynyl)-fluoren-9-one;
2-bromo-7-[(1R,5R)-6-methyl-3,6-diazabicyclo[3.2.0]hept-3-yl]-fluoren-9-one;
2-(1-azabicyclo[2.2.2]oct-3-yloxy)-7-bromo-fluoren-9-one;
2-(hexahydropyrrolo[3,4-c]pyrrol-2-yl)-7-hydroxy-fluoren-9-one;
2-amino-7-(5-methylhexahydropyrrolo[3,4-c]pyrrol-2-yl)-fluoren-9-one;
2-dimethylamino-7-(hexahydropyrrolo[3,4-c]pyrrol-2-yl)-fluoren-9-one;
2-dimethylamino-7-(5-methylhexahydropyrrolo[3,4-c]pyrrol-2-yl)-fluoren-9-one;
N-{7-(hexahydropyrrolo[3,4-c]pyrrol-2-yl)-9-oxo-9H-fluoren-2-yl}-acetamide;
{7-(hexahydropyrrolo[3,4-c]pyrrol-2-yl)-9-oxo-9H-fluoren-2-yl}-carbamic acid methyl ester;
6-(hexahydropyrrolo[3,4-c]pyrrol-2-yl)-9-oxa-1-azaanthracen-10-one; and
6-(5-methyl-hexahydropyrrolo[3,4-c]pyrrol-2-yl)-9-oxa-1-azaanthracen-10-one;
or pharmaceutically acceptable salts, esters, amides, and prodrugs thereof.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods of the Invention

Compounds and compositions of the invention are useful for modulating the effects of nAChRs, and more particularly α7 nAChRs. In particular, the compounds and compositions of the invention can be used for treating or preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

In addition, the invention relates to a method for treating or preventing a condition or disorder modulated by an α7 nicotinic acetylcholine receptor comprising the step of administering a compound of the formula (II):

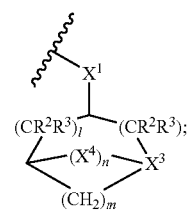
(II)

or a pharmaceutically acceptable salt, ester, amide, or prodrug thereof, wherein:

A and B are each independently selected from the group consisting of hydroxy, halogen; alkoxy; amino; alkylamino; acylamino; dialkylamino; cyano; nitro;

—N($R^z$)C(=O)(O$R^y$); and a group of formula (a):

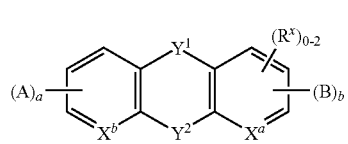
(a)

a group of formula (b):

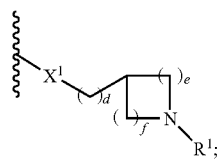
(b)

a group of formula (c):

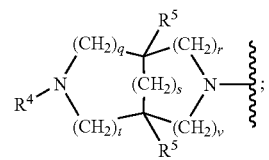
(c)

a group of formula (d):

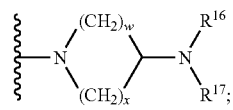
(d)

a group of formula (e):

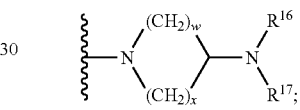
(e)

a group of formula (f):

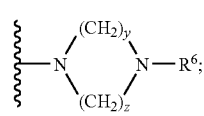
(f)

a group of formula (g):

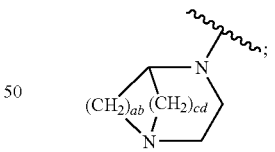
(g)

(h) —C≡CCH$_2$N$R^7R^8$; (i) —O—(C($R^{20a}R^{20b}$))$_{2\text{-}3}$N($R^{21}$)($R^{22}$); and (j) —O—(C$R^{23a}R^{23b}$)$_{2\text{-}3}$N$^+$($R^{24}$)($R^{25}$)($R^{26}$);

$X^a$ and $X^b$ are each independently selected from the group consisting of C, C(H) and N; provided that when one of $X^a$ and $X^b$ is N, the other is C or C(H);

$X^1$ at each occurrence is selected from the group consisting of O, S, and —N($R^9$)—;

$X^2$ at each occurrence is selected from the group consisting of O, S, —CH$_2$—, and —N($R^{10}$)—;

$X^3$ is C(H) or N;

$X^4$ is CH$_2$ or N($R^{13}$); provided that when $X^3$ is N, $X^4$ is CH$_2$ or when $X^4$ is N($R^{13}$), $X^3$ is C(H);

Y¹ is independently selected from the group consisting of —C(O)—, —CH₂—, —CH(OH)—, —C(S)—, —N(R¹¹)—, —O—, —S—, —S(O)—, —S(O)₂—, —C(O)NH—, and —S(O)₂NH—;

Y² is a bond or Y² is independently selected from —O—, —S—, and —N(R¹²)—;

R¹ is independently selected from hydrogen and alkyl;

R² and R³ at each occurrence are each independently selected from the group consisting of hydrogen and alkyl;

R⁴ and R⁶ at each occurrence are each independently selected from the group consisting of hydrogen and alkyl;

R⁵ at each occurrence are each independently selected from the group consisting of hydrogen, alkyl, and alkoxycarbonyl;

R⁷ and R⁸ are each independently selected from hydrogen and alkyl or R⁷ and R⁸ taken together with the nitrogen atom to which each is attached form a 4- to 8-membered cyclic amine;

R⁹, R¹⁰, R¹¹, R¹² and R¹³ at each occurrence are each independently selected from hydrogen and alkyl;

R¹⁶ and R¹⁷ are each independently selected from hydrogen and alkyl, or R¹⁶ and R¹⁷ taken together with the nitrogen atom to which each is attached form a 4- to 8-membered cyclic amine;

R²⁰ᵃ, R²⁰ᵇR²³ᵃ, R²³ᵇ are each independently are each independently selected from the group consisting of hydrogen and alkyl;

R²¹ and R²² are each independently selected from the group consisting of hydrogen and alkyl;

R²⁴, R²⁵, and R²⁶ are alkyl, or one pair of substituents selected from R²⁴, R²⁵, and R²⁶ is taken together with the nitrogen atom to which each is attached form a 4- to 8-membered cyclic amine and the remaining substituent is selected from hydrogen and alkyl;

Rˣ is independently selected at each occurrence from the group consisting of halogen, alkoxy, amino, alkylamino, dialkylamino, acylamino, dialkylaminoalkyl, and cyano;

Rʸ and Rᶻ are each independently selected from the group consisting of hydrogen and alkyl;

a is 0 or 1;

b is 0 or 1; provided that when one of a and b is 0, the other is 1;

d is independently selected from 0 and 1;

e and f are each independently selected from 0, 1, 2 and 3, provided that the sum total of e and f is 2, 3, or 4, provided that when d is 0, e and f are selected from 1, 2 or 3;

j is independently selected from 2 and 3;

h and k are each independently selected from 0, 1, and 2, provided that the sum total of h and k is 2, 3, or 4, provided that when X² is O, S, or N(R¹⁰), h and k are both 2;

l is 0 or 1, m is 2 or 3, and n is 0, 1, or 2, provided that the sum total of l, m, and n is 4, 5, or 6;

q, r, s, t, and v are each independently selected from 0, 1, or 2, provided that the sum of q and r; t and v; q, s, and t; and r, s, and v; are each at least 1;

w and x are each independently selected from 1, 2, or 3, provided that the sum total of w and x is 3, 4, 5, or 6;

y and z are each independently selected from 2, 3, or 4, provided that the sum total of y and z is 4, 5, or 6; and ab is 2 or 3, and cd is 1 or 2.

Preferred compounds for the method of the invention are those wherein the group A, the group B, or both groups A and B are selected from the group consisting of substituents (a)-(j). More preferably, the compound for the method is one wherein the group A, the group B, or both groups A and B is a substituent (d). When one of A or B is selected from a group of formula (d) it can be beneficial that the other is selected from bromo, hydroxy, amino, dialkylamino, acylamino, and —N(H)C(=O)(OCH₃). It is particularly preferred when the group of formula (d) is

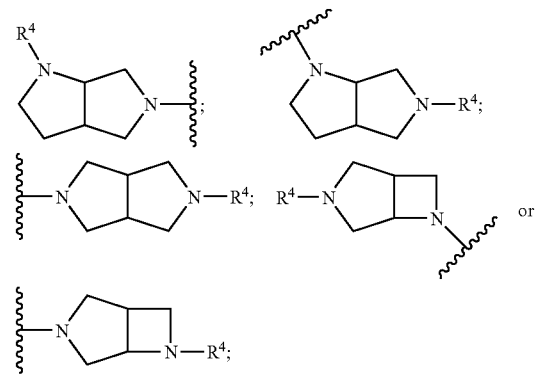

wherein R⁴ is hydrogen or alkyl, and more particularly, when the other substituent of A or B is amino.

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention can be useful for the treatment or prevention of a number of α7 nAChR-mediated diseases or conditions.

Specific examples of compounds that can be useful for the treatment or prevention of α7 nAChR-mediated diseases or conditions include, but are not limited to, compounds described in the Examples, such as 2,7-bis[(2R)-1-methylpyrrolidin-2-ylmethoxy]-fluoren-9-one;
2,7-bis[(2R)-azetidin-2-ylmethoxy]-fluoren-9-one;
2,7-bis[(2R)-1-methylazetidin-2-ylmethoxy]-fluoren-9-one;
2,7-bis[(3S)-pyrrolidin-3-yloxy]-fluoren-9-one;
2,7-bis[(3S)-1-methylpyrrolidin-3-yloxy]-fluoren-9-one;
2,7-bis-[(3R)-1-azabicyclo[2.2.2]octan-3-yloxy]-fluoren-9-one;
2,7-bis[(3S)-1-azabicyclo[2.2.2]octan-3-yloxy]-fluoren-9-one;
2-[(3R)-1-azabicyclo[2.2.2]octan-3-yloxy]-fluoren-9-one;
2-[(3S)-1-azabicyclo[2.2.2]octan-3-yloxy]-fluoren-9-one;
2,7-bis(4-methyl-[1,4]diazepan-1-yl)-fluoren-9-one;
2,7-bis[3,7-diazabicyclo[3.3.0]octan-3-yl]-fluoren-9-one;
2,7-bis[7-methyl-3,7-diazabicyclo[3.3.0]octan-3-yl]fluoren-9-one;
2-[3,7-diazabicyclo[3.3.0]octan-3-yl]-fluoren-9-one;
2-[7-methyl-3,7-diazabicyclo[3.3.0]octan-3-yl]-fluoren-9-one;
2,7-bis(3-diethylamino-propyn-1-yl)-fluoren-9-one;
3,7-bis(2-diethylaminoethoxy)dibenzothiophene;
3,7-bis(2-diethylaminoethoxy)dibenzothiophene-5-oxide;
3,7-bis[(3S)-1-azabicyclo[2.2.2]octan-3-yloxy]-dibenzothiophene;
2-[(1S,5S)-3,6-diazabicyclo[3.2.0]heptan-3-yl]-dibenzothiophene-5,5-dioxide;
2-amino-7-[3,7-diazabicyclo[3.3.0]octan-3-yl]-fluoren-9-one;
2-[(3R)-1-azabicyclo[2.2.2]octan-3-yloxy]-xanthen-9-one;
2-(1-azabicyclo[2.2.2]octan-3-yloxy)-9H-carbazole;
2,7-bis-(piperidin-4-yloxy)-fluoren-9-one;
2,7-bis-(1-methyl-piperidin-4-yloxy)-fluoren-9-one;

2,7-bis-(8-methyl-8-aza-bicyclo[3.2.1]oct-3-yloxy)-fluoren-9-one;
2,7-bis-[(S)-1-methylpyrrolidin-2-ylmethoxy]-fluoren-9-one;
2,7-bis-(4-methylpiperazin-1-yl)-fluoren-9-one;
2,7-bis-[(1S,5S)-3,6-diazabicyclo[3.2.0]hept-3-yl]-fluoren-9-one;
2,7-bis-[(1S,5S)-6-methyl-3,6-diazabicyclo[3.2.0]hept-3-yl]-fluoren-9-one;
2,7-bis-[(1R,5R)-6-methyl-3,6-diazabicyclo[3.2.0]hept-3-yl]-fluoren-9-one;
2,7-bis-[(S)-3-dimethylaminopyrrolidin-1-yl]-fluoren-9-one;
{3-[7-(3-diethylaminoprop-1-ynyl)-5,5-dioxo-5H-5λ$^6$-dibenzothiophen-3-yl]-prop-2-ynyl}-diethylamine;
2,7-bis-[3,7-diazabicyclo[3.3.0]octan-3-yl]-dibenzothiophene-5,5-dioxide;
2-[(S)-pyrrolidin-3-yloxy]-fluoren-9-one;
2-[(S)-1-methylpyrrolidin-3-yloxy]-fluoren-9-one;
2-(piperidin-4-yloxy)-fluoren-9-one;
2-(1-azabicyclo[2.2.2]oct-3-ylamino)-fluoren-9-one;
2-[(1R,5R)-6-methyl-3,6-diazabicyclo[3.2.0]hept-3-yl]-fluoren-9-one;
2-[(1S,5S)-3,6-diazabicyclo[3.2.0]hept-3-yl]-fluoren-9-one;
2-[(1S,5S)-6-methyl-3,6-diazabicyclo[3.2.0]hept-3-yl]-fluoren-9-one;
2-(1,4-diazabicyclo[3.2.2]non-4-yl)-fluoren-9-one;
2-(9H-fluoren-2-yl)-octahydropyrrolo[3,4-c]pyrrole;
(1-azabicyclo[2.2.2]oct-3-yl)-(9H-fluoren-2-yl)-amine;
(R)-3-(9H-fluoren-2-yloxy)-1-azabicyclo[2.2.2]octane;
(S)-3-(9H-fluoren-2-yloxy)-1-azabicyclo[2.2.2]octane;
(R)-3-(5,5-dioxo-5H-5λ$^6$-dibenzothiophen-3-yloxy)-1-azabicyclo[2.2.2]octane;
(S)-3-(5,5-dioxo-5H-5λ$^6$-dibenzothiophen-3-yloxy)-1-azabicyclo[2.2.2]octane;
1-(5,5-dioxo-5H-5λ$^6$-dibenzothiophen-3-yl)-4-methylpiperazine;
(1S,5S)-3-(5,5-dioxo-5H-5λ$^6$-dibenzothiophen-3-yl)-3,6-diazabicyclo[3.2.0]heptane;
(1S,5S)-3-(5,5-dioxo-5H-5λ$^6$-dibenzothiophen-3-yl)-6-methyl-3,6-diazabicyclo[3.2.0]heptane;
4-(5,5-dioxo-5H-5λ$^6$-dibenzothiophen-3-yl)-1,4-diazabicyclo[3.2.2]nonane;
(S)-2-(1-azabicyclo[2.2.2]oct-3-yloxy)-xanthen-9-one;
2-(3,7-diazabicyclo[3.3.0]oct-3-yl)-xanthen-9-one;
2-(7-methyl-3,7-diazabicyclo[3.3.0]oct-3-yl)-xanthen-9-one;
2-(2-diethylaminoethoxy)-7-(3-diethylaminoprop-1-ynyl)-fluoren-9-one;
2-bromo-7-[(1R,5R)-6-methyl-3,6-diazabicyclo[3.2.0]hept-3-yl]-fluoren-9-one;
2-(1-azabicyclo[2.2.2]oct-3-yloxy)-7-bromo-fluoren-9-one;
2-(1-methylpiperidin-4-yloxy)-7-(piperidin-4-yloxy)-fluoren-9-one;
2-(hexahydropyrrolo[3,4-c]pyrrol-2-yl)-7-hydroxy-fluoren-9-one;
2-amino-7-(5-methylhexahydropyrrolo[3,4-c]pyrrol-2-yl)-fluoren-9-one;
2-dimethylamino-7-(hexahydropyrrolo[3,4-c]pyrrol-2-yl)-fluoren-9-one;
2-dimethylamino-7-(5-methylhexahydropyrrolo[3,4-c]pyrrol-2-yl)-fluoren-9-one;
N-{7-(hexahydropyrrolo[3,4-c]pyrrol-2-yl)-9-oxo-9H-fluoren-2-yl}-acetamide;
{7-(hexahydropyrrolo[3,4-c]pyrrol-2-yl)-9-oxo-9H-fluoren-2-yl}-carbamic acid methyl ester;
6-(hexahydropyrrolo[3,4-c]pyrrol-2-yl)-9-oxa-1-azaanthracen-10-one; and
6-(5-methyl-hexahydropyrrolo[3,4-c]pyrrol-2-yl)-9-oxa-1-azaanthracen-10-one;

and pharmaceutically acceptable salts, esters, amides, and prodrugs thereof. Additionally, compounds that can be prepared by methods described in the Schemes and methods readily available to one with skill in the art include, but are not limited to, for example, 2,7-bis-(2-aminoethoxy)-fluorene;
2,7-bis-(3-aminopropoxy)-fluorene;
2,7-bis-(2-methylaminoethoxy)-fluorene;
2,7-bis-(2-ethylaminoethoxy)-fluorene;
2,7-bis-(2-n-propylaminoethoxy)-fluorene;
2,7-bis-(3-methylaminopropoxy)-fluorene;
2,7-bis-(3-ethylaminopropoxy)-fluorene;
2,7-bis-(3-n-propylaminopropoxy)-fluorene;
2,7-bis-(2-dimethylaminoethoxy)-fluorene;
2,7-bis-(2-diethylaminoethoxy)-fluorene;
2,7-bis-(2-di-n-propylaminoethoxy)-fluorene;
2,7-bis-(3-dimethylaminopropoxy)-fluorene;
2,7-bis-(3-diethylaminopropoxy)-fluorene;
2,7-bis-(3-di-n-propylaminopropoxy)-fluorene;
2,7-bis-(2-azetidin-1-yl-ethoxy)-fluorene;
2,7-bis-(2-pyrrolidin-1-yl-ethoxy)-fluorene;
2,7-bis-(2-piperidin-1-yl-ethoxy)-fluorene;
2,7-bis-(2-azetidin-1-yl-propoxy)-fluorene;
2,7-bis-(3-pyrrolidin-1-yl-propoxy)-fluorene;
2,7-bis-(3-piperidin-1-yl-propoxy)-fluorene;
2,7-bis-(2-trimethylammoniumethoxy)-fluorene;
2,7-bis-(3-trimethylammoniumpropoxy)-fluorene;
2,6-bis-(2-aminoethoxy)-fluorene;
2,6-bis-(3-aminopropoxy)-fluorene;
2,6-bis-(2-methylaminoethoxy)-fluorene;
2,6-bis-(2-ethylaminoethoxy)-fluorene;
2,6-bis-(2-n-propylaminoethoxy)-fluorene;
2,6-bis-(3-methylaminopropoxy)-fluorene;
2,6-bis-(3-ethylaminopropoxy)-fluorene;
2,6-bis-(3-n-propylaminopropoxy)-fluorene;
2,6-bis-(2-dimethylaminoethoxy)-fluorene;
2,6-bis-(2-diethylaminoethoxy)-fluorene;
2,6-bis-(2-di-n-propylaminoethoxy)-fluorene;
2,6-bis-(3-dimethylaminopropoxy)-fluorene;
2,6-bis-(3-diethylaminopropoxy)-fluorene;
2,6-bis-(3-di-n-propylaminopropoxy)-fluorene;
2,6-bis-(2-azetidin-1-yl-ethoxy)-fluorene;
2,6-bis-(2-pyrrolidin-1-yl-ethoxy)-fluorene;
2,6-bis-(2-piperidin-1-yl-ethoxy)-fluorene;
2,6-bis-(3-azetidin-1-yl-propoxy)-fluorene;
2,6-bis-(3-pyrrolidin-1-yl-propoxy)-fluorene;
2,6-bis-(3-piperidin-1-yl-propoxy)-fluorene;
2,6-bis-(2-trimethylammoniumethoxy)-fluorene;
2,6-bis-(3-trimethylammoniumpropoxy)-fluorene;
3,6-bis-(2-aminoethoxy)-fluorene;
3,6-bis-(3-aminopropoxy)-fluorene;
3,6-bis-(2-methylaminoethoxy)-fluorene;
3,6-bis-(2-ethylaminoethoxy)-fluorene;
3,6-bis-(2-n-propylaminoethoxy)-fluorene;
3,6-bis-(3-methylaminopropoxy)-fluorene;
3,6-bis-(3-ethylaminopropoxy)-fluorene;
3,6-bis-(3-n-propylaminopropoxy)-fluorene;
3,6-bis-(2-dimethylaminoethoxy)-fluorene;
3,6-bis-(2-diethylaminoethoxy)-fluorene;
3,6-bis-(2-di-n-propylaminoethoxy)-fluorene;
3,6-bis-(3-dimethylaminopropoxy)-fluorene;
3,6-bis-(3-diethylaminopropoxy)-fluorene;
3,6-bis-(3-di-n-propylaminopropoxy)-fluorene;
3,6-bis-(2-azetidin-1-yl-ethoxy)-fluorene;

3,6-bis-(2-pyrrolidin-1-yl-ethoxy)-fluorene;
3,6-bis-(2-piperidin-1-yl-ethoxy)-fluorene;
3,6-bis-(3-azetidin-1-yl-propoxy)-fluorene;
3,6-bis-(3-pyrrolidin-1-yl-propoxy)-fluorene;
3,6-bis-(3-piperidin-1-yl-propoxy)-fluorene;
3,6-bis-(2-trimethylammoniumethoxy)-fluorene;
3,6-bis-(3-trimethylammoniumpropoxy)-fluorene;
2,7-bis-(2-aminoethoxy)-fluoren-9-ol;
2,7-bis-(3-aminopropoxy)-fluoren-9-ol;
2,7-bis-(2-methylaminoethoxy)-fluoren-9-ol;
2,7-bis-(2-ethylaminoethoxy)-fluoren-9-ol;
2,7-bis-(2-n-propylaminoethoxy)-fluoren-9-ol;
2,7-bis-(3-methylaminopropoxy)-fluoren-9-ol;
2,7-bis-(3-ethylaminopropoxy)-fluoren-9-ol;
2,7-bis-(3-n-propylaminopropoxy)-fluoren-9-ol;
2,7-bis-(2-dimethylaminoethoxy)-fluoren-9-ol;
2,7-bis-(2-diethylaminoethoxy)-fluoren-9-ol;
2,7-bis-(2-di-n-propylaminoethoxy)-fluoren-9-ol;
2,7-bis-(3-dimethylaminopropoxy)-fluoren-9-ol;
2,7-bis-(3-diethylaminopropoxy)-fluoren-9-ol;
2,7-bis-(3-di-n-propylaminopropoxy)-fluoren-9-ol;
2,7-bis-(2-azetidin-1-yl-ethoxy)-fluoren-9-ol;
2,7-bis-(2-pyrrolidin-1-yl-ethoxy)-fluoren-9-ol;
2,7-bis-(2-piperidin-1-yl-ethoxy)-fluoren-9-ol;
2,7-bis-(3-azetidin-1-yl-propoxy)-fluoren-9-ol;
2,7-bis-(3-pyrrolidin-1-yl-propoxy)-fluoren-9-ol;
2,7-bis-(3-piperidin-1-yl-propoxy)-fluoren-9-ol;
2,7-bis-(2-trimethylammoniumethoxy)-fluoren-9-ol;
2,7-bis-(3-trimethylammoniumpropoxy)-fluoren-9-ol;
2,6-bis-(2-aminoethoxy)-fluoren-9-ol;
2,6-bis-(3-aminopropoxy)-fluoren-9-ol;
2,6-bis-(2-methylaminoethoxy)-fluoren-9-ol;
2,6-bis-(2-ethylaminoethoxy)-fluoren-9-ol;
2,6-bis-(2-n-propylaminoethoxy)-fluoren-9-ol;
2,6-bis-(3-methylaminopropoxy)-fluoren-9-ol;
2,6-bis-(3-ethylaminopropoxy)-fluoren-9-ol;
2,6-bis-(3-n-propylaminopropoxy)-fluoren-9-ol;
2,6-bis-(2-dimethylaminoethoxy)-fluoren-9-ol;
2,6-bis-(2-diethylaminoethoxy)-fluoren-9-ol;
2,6-bis-(2-di-n-propylaminoethoxy)-fluoren-9-ol;
2,6-bis-(3-dimethylaminopropoxy)-fluoren-9-ol;
2,6-bis-(3-diethylaminopropoxy)-fluoren-9-ol;
2,6-bis-(3-di-n-propylaminopropoxy)-fluoren-9-ol;
2,6-bis-(2-azetidin-1-yl-ethoxy)-fluoren-9-ol;
2,6-bis-(2-pyrrolidin-1-yl-ethoxy)-fluoren-9-ol;
2,6-bis-(2-piperidin-1-yl-ethoxy)-fluoren-9-ol;
2,6-bis-(3-azetidin-1-yl-propoxy)-fluoren-9-ol;
2,6-bis-(3-pyrrolidin-1-yl-propoxy)-fluoren-9-ol;
2,6-bis-(3-piperidin-1-yl-propoxy)-fluoren-9-ol;
2,6-bis-(2-trimethylammoniumethoxy)-fluoren-9-ol;
2,6-bis-(3-trimethylammoniumpropoxy)-fluoren-9-ol;
3,6-bis-(2-aminoethoxy)-fluoren-9-ol;
3,6-bis-(3-aminopropoxy)-fluoren-9-ol;
3,6-bis-(2-methylaminoethoxy)-fluoren-9-ol;
3,6-bis-(2-ethylaminoethoxy)-fluoren-9-ol;
3,6-bis-(2-n-propylaminoethoxy)-fluoren-9-ol;
3,6-bis-(3-methylaminopropoxy)-fluoren-9-ol;
3,6-bis-(3-ethylaminopropoxy)-fluoren-9-ol;
3,6-bis-(3-n-propylaminopropoxy)-fluoren-9-ol;
3,6-bis-(2-dimethylaminoethoxy)-fluoren-9-ol;
3,6-bis-(2-diethylaminoethoxy)-fluoren-9-ol;
3,6-bis-(2-di-n-propylaminoethoxy)-fluoren-9-ol;
3,6-bis-(3-dimethylaminopropoxy)-fluoren-9-ol;
3,6-bis-(3-diethylaminopropoxy)-fluoren-9-ol;
3,6-bis-(3-di-n-propylaminopropoxy)-fluoren-9-ol;
3,6-bis-(2-azetidin-1-yl-ethoxy)-fluoren-9-ol;
3,6-bis-(2-pyrrolidin-1-yl-ethoxy)-fluoren-9-ol;
3,6-bis-(2-piperidin-1-yl-ethoxy)-fluoren-9-ol;
3,6-bis-(3-azetidin-1-yl-propoxy)-fluoren-9-ol;
3,6-bis-(3-pyrrolidin-1-yl-propoxy)-fluoren-9-ol;
3,6-bis-(3-piperidin-1-yl-propoxy)-fluoren-9-ol;
3,6-bis-(2-trimethylammoniumethoxy)-fluoren-9-ol;
3,6-bis-(3-trimethylammoniumpropoxy)-fluoren-9-ol;
2,7-bis-(2-aminoethoxy)-fluoren-9-one;
2,7-bis-(3-aminopropoxy)-fluoren-9-one;
2,7-bis-(2-methylaminoethoxy)-fluoren-9-one;
2,7-bis-(2-ethylaminoethoxy)-fluoren-9-one;
2,7-bis-(2-n-propylaminoethoxy)-fluoren-9-one;
2,7-bis-(3-methylaminopropoxy)-fluoren-9-one;
2,7-bis-(3-ethylaminopropoxy)-fluoren-9-one;
2,7-bis-(3-n-propylaminopropoxy)-fluoren-9-one;
2,7-bis-(2-dimethylaminoethoxy)-fluoren-9-one;
2,7-bis-(2-diethylaminoethoxy)-fluoren-9-one;
2,7-bis-(2-di-n-propylaminoethoxy)-fluoren-9-one;
2,7-bis-(3-dimethylaminopropoxy)-fluoren-9-one;
2,7-bis-(3-diethylaminopropoxy)-fluoren-9-one;
2,7-bis-(3-di-n-propylaminopropoxy)-fluoren-9-one;
2,7-bis-(2-azetidin-1-yl-ethoxy)-fluoren-9-one;
2,7-bis-(2-pyrrolidin-1-yl-ethoxy)-fluoren-9-one;
2,7-bis-(2-piperidin-1-yl-ethoxy)-fluoren-9-one;
2,7-bis-(3-azetidin-1-yl-propoxy)-fluoren-9-one;
2,7-bis-(3-pyrrolidin-1-yl-propoxy)-fluoren-9-one;
2,7-bis-(3-piperidin-1-yl-propoxy)-fluoren-9-one;
2,7-bis-(2-trimethylammoniumethoxy)-fluoren-9-one;
2,7-bis-(3-trimethylammoniumpropoxy)-fluoren-9-one;
2,6-bis-(2-aminoethoxy)-fluoren-9-one;
2,6-bis-(3-aminopropoxy)-fluoren-9-one;
2,6-bis-(2-methylaminoethoxy)-fluoren-9-one;
2,6-bis-(2-ethylaminoethoxy)-fluoren-9-one;
2,6-bis-(2-n-propylaminoethoxy)-fluoren-9-one;
2,6-bis-(3-methylaminopropoxy)-fluoren-9-one;
2,6-bis-(3-ethylaminopropoxy)-fluoren-9-one;
2,6-bis-(3-n-propylaminopropoxy)-fluoren-9-one;
2,6-bis-(2-dimethylaminoethoxy)-fluoren-9-one;
2,6-bis-(2-diethylaminoethoxy)-fluoren-9-one;
2,6-bis-(2-di-n-propylaminoethoxy)-fluoren-9-one;
2,6-bis-(3-dimethylaminopropoxy)-fluoren-9-one;
2,6-bis-(3-diethylaminopropoxy)-fluoren-9-one;
2,6-bis-(3-di-n-propylaminopropoxy)-fluoren-9-one;
2,6-bis-(2-azetidin-1-yl-ethoxy)-fluoren-9-one;
2,6-bis-(2-pyrrolidin-1-yl-ethoxy)-fluoren-9-one;
2,6-bis-(2-piperidin-1-yl-ethoxy)-fluoren-9-one;
2,6-bis-(3-azetidin-1-yl-propoxy)-fluoren-9-one;
2,6-bis-(3-pyrrolidin-1-yl-propoxy)-fluoren-9-one;
2,6-bis-(3-piperidin-1-yl-propoxy)-fluoren-9-one;
2,6-bis-(2-trimethylammoniumethoxy)-fluoren-9-one;
2,6-bis-(3-trimethylammoniumpropoxy)-fluoren-9-one;
3,6-bis-(2-aminoethoxy)-fluoren-9-one;
3,6-bis-(3-aminopropoxy)-fluoren-9-one;
3,6-bis-(2-methylaminoethoxy)-fluoren-9-one;
3,6-bis-(2-ethylaminoethoxy)-fluoren-9-one;
3,6-bis-(2-n-propylaminoethoxy)-fluoren-9-one;
3,6-bis-(3-methylaminopropoxy)-fluoren-9-one;
3,6-bis-(3-ethylaminopropoxy)-fluoren-9-one;
3,6-bis-(3-n-propylaminopropoxy)-fluoren-9-one;
3,6-bis-(2-dimethylaminoethoxy)-fluoren-9-one;
3,6-bis-(2-diethylaminoethoxy)-fluoren-9-one;
3,6-bis-(2-di-n-propylaminoethoxy)-fluoren-9-one;
3,6-bis-(3-dimethylaminopropoxy)-fluoren-9-one;
3,6-bis-(3-diethylaminopropoxy)-fluoren-9-one;
3,6-bis-(3-di-n-propylaminopropoxy)-fluoren-9-one;
3,6-bis-(2-azetidin-1-yl-ethoxy)-fluoren-9-one;
3,6-bis-(2-pyrrolidin-1-yl-ethoxy)-fluoren-9-one;
3,6-bis-(2-piperidin-1-yl-ethoxy)-fluoren-9-one;

3,6-bis-(3-azetidin-1-yl-propoxy)-fluoren-9-one;
3,6-bis-(3-pyrrolidin-1-yl-propoxy)-fluoren-9-one;
3,6-bis-(3-piperidin-1-yl-propoxy)-fluoren-9-one;
3,6-bis-(2-trimethylammoniumethoxy)-fluoren-9-one;
3,6-bis-(3-trimethylammoniumpropoxy)-fluoren-9-one;
3,7-bis-(2-aminoethoxy)-dibenzofuran;
3,7-bis-(3-aminopropoxy)-dibenzofuran;
3,7-bis-(2-methylaminoethoxy)-dibenzofuran;
3,7-bis-(2-ethylaminoethoxy)-dibenzofuran;
3,7-bis-(2-n-propylaminoethoxy)-dibenzofuran;
3,7-bis-(3-methylaminopropoxy)-dibenzofuran;
3,7-bis-(3-ethylaminopropoxy)-dibenzofuran;
3,7-bis-(3-n-propylaminopropoxy)-dibenzofuran;
3,7-bis-(2-dimethylaminoethoxy)-dibenzofuran;
3,7-bis-(2-diethylaminoethoxy)-dibenzofuran;
3,7-bis-(2-di-n-propylaminoethoxy)-dibenzofuran;
3,7-bis-(3-dimethylaminopropoxy)-dibenzofuran;
3,7-bis-(3-diethylaminopropoxy)-dibenzofuran;
3,7-bis-(3-di-n-propylaminopropoxy)-dibenzofuran;
3,7-bis-(2-azetidin-1-yl-ethoxy)-dibenzofuran;
3,7-bis-(2-pyrrolidin-1-yl-ethoxy)-dibenzofuran;
3,7-bis-(2-piperidin-1-yl-ethoxy)-dibenzofuran;
3,7-bis-(3-azetidin-1-yl-propoxy)-dibenzofuran;
3,7-bis-(3-pyrrolidin-1-yl-propoxy)-dibenzofuran;
3,7-bis-(3-piperidin-1-yl-propoxy)-dibenzofuran;
3,7-bis-(2-trimethylammoniumethoxy)-dibenzofuran;
3,7-bis-(3-trimethylammoniumpropoxy)-dibenzofuran;
2,7-bis-(2-aminoethoxy)-dibenzofuran;
2,7-bis-(3-aminopropoxy)-dibenzofuran;
2,7-bis-(2-methylaminoethoxy)-dibenzofuran;
2,7-bis-(2-ethylaminoethoxy)-dibenzofuran;
2,7-bis-(2-n-propylaminoethoxy)-dibenzofuran;
2,7-bis-(3-methylaminopropoxy)-dibenzofuran;
2,7-bis-(3-ethylaminopropoxy)-dibenzofuran;
2,7-bis-(3-n-propylaminopropoxy)-dibenzofuran;
2,7-bis-(2-dimethylaminoethoxy)-dibenzofuran;
2,7-bis-(2-diethylaminoethoxy)-dibenzofuran;
2,7-bis-(2-di-n-propylaminoethoxy)-dibenzofuran;
2,7-bis-(3-dimethylaminopropoxy)-dibenzofuran;
2,7-bis-(3-diethylaminopropoxy)-dibenzofuran;
2,7-bis-(3-di-n-propylaminopropoxy)-dibenzofuran;
2,7-bis-(2-azetidin-1-yl-ethoxy)-dibenzofuran;
2,7-bis-(2-pyrrolidin-1-yl-ethoxy)-dibenzofuran;
2,7-bis-(2-piperidin-1-yl-ethoxy)-dibenzofuran;
2,7-bis-(3-azetidin-1-yl-propoxy)-dibenzofuran;
2,7-bis-(3-pyrrolidin-1-yl-propoxy)-dibenzofuran;
2,7-bis-(3-piperidin-1-yl-propoxy)-dibenzofuran;
2,7-bis-(2-trimethylammoniumethoxy)-dibenzofuran;
2,7-bis-(3-trimethylammoniumpropoxy)-dibenzofuran;
2,8-bis-(2-aminoethoxy)-dibenzofuran;
2,8-bis-(3-aminopropoxy)-dibenzofuran;
2,8-bis-(2-methylaminoethoxy)-dibenzofuran;
2,8-bis-(2-ethylaminoethoxy)-dibenzofuran;
2,8-bis-(2-n-propylaminoethoxy)-dibenzofuran;
2,8-bis-(3-methylaminopropoxy)-dibenzofuran;
2,8-bis-(3-ethylaminopropoxy)-dibenzofuran;
2,8-bis-(3-n-propylaminopropoxy)-dibenzofuran;
2,8-bis-(2-dimethylaminoethoxy)-dibenzofuran;
2,8-bis-(2-diethylaminoethoxy)-dibenzofuran;
2,8-bis-(2-di-n-propylaminoethoxy)-dibenzofuran;
2,8-bis-(3-dimethylaminopropoxy)-dibenzofuran;
2,8-bis-(3-diethylaminopropoxy)-dibenzofuran;
2,8-bis-(3-di-n-propylaminopropoxy)-dibenzofuran;
2,8-bis-(2-azetidin-1-yl-ethoxy)-dibenzofuran;
2,8-bis-(2-pyrrolidin-1-yl-ethoxy)-dibenzofuran;
2,8-bis-(2-piperidin-1-yl-ethoxy)-dibenzofuran;
2,8-bis-(3-azetidin-1-yl-propoxy)-dibenzofuran;
2,8-bis-(3-pyrrolidin-1-yl-propoxy)-dibenzofuran;
2,8-bis-(3-piperidin-1-yl-propoxy)-dibenzofuran;
2,8-bis-(2-trimethylammoniumethoxy)-dibenzofuran;
2,8-bis-(3-trimethylammoniumpropoxy)-dibenzofuran;
3,7-bis-(2-aminoethoxy)-dibenzothiophene;
3,7-bis-(3-aminopropoxy)-dibenzothiophene;
3,7-bis-(2-methylaminoethoxy)-dibenzothiophene;
3,7-bis-(2-ethylaminoethoxy)-dibenzothiophene;
3,7-bis-(2-n-propylaminoethoxy)-dibenzothiophene;
3,7-bis-(3-methylaminopropoxy)-dibenzothiophene;
3,7-bis-(3-ethylaminopropoxy)-dibenzothiophene;
3,7-bis-(3-n-propylaminopropoxy)-dibenzothiophene;
3,7-bis-(2-dimethylaminoethoxy)-dibenzothiophene;
3,7-bis-(2-diethylaminoethoxy)-dibenzothiophene;
3,7-bis-(2-di-n-propylaminoethoxy)-dibenzothiophene;
3,7-bis-(3-dimethylaminopropoxy)-dibenzothiophene;
3,7-bis-(3-diethylaminopropoxy)-dibenzothiophene;
3,7-bis-(3-di-n-propylaminopropoxy)-dibenzothiophene;
3,7-bis-(2-azetidin-1-yl-ethoxy)-dibenzothiophene;
3,7-bis-(2-pyrrolidin-1-yl-ethoxy)-dibenzothiophene;
3,7-bis-(2-piperidin-1-yl-ethoxy)-dibenzothiophene;
3,7-bis-(3-azetidin-1-yl-propoxy)-dibenzothiophene;
3,7-bis-(3-pyrrolidin-1-yl-propoxy)-dibenzothiophene;
3,7-bis-(3-piperidin-1-yl-propoxy)-dibenzothiophene;
3,7-bis-(2-trimethylammoniumethoxy)-dibenzothiophene;
3,7-bis-(3-trimethylammoniumpropoxy)-dibenzothiophene;
2,7-bis-(2-aminoethoxy)-dibenzothiophene;
2,7-bis-(3-aminopropoxy)-dibenzothiophene;
2,7-bis-(2-methylaminoethoxy)-dibenzothiophene;
2,7-bis-(2-ethylaminoethoxy)-dibenzothiophene;
2,7-bis-(2-n-propylaminoethoxy)-dibenzothiophene;
2,7-bis-(3-methylaminopropoxy)-dibenzothiophene;
2,7-bis-(3-ethylaminopropoxy)-dibenzothiophene;
2,7-bis-(3-n-propylaminopropoxy)-dibenzothiophene;
2,7-bis-(2-dimethylaminoethoxy)-dibenzothiophene;
2,7-bis-(2-diethylaminoethoxy)-dibenzothiophene;
2,7-bis-(2-di-n-propylaminoethoxy)-dibenzothiophene;
2,7-bis-(3-dimethylaminopropoxy)-dibenzothiophene;
2,7-bis-(3-diethylaminopropoxy)-dibenzothiophene;
2,7-bis-(3-di-n-propylaminopropoxy)-dibenzothiophene;
2,7-bis-(2-azetidin-1-yl-ethoxy)-dibenzothiophene;
2,7-bis-(2-pyrrolidin-1-yl-ethoxy)-dibenzothiophene;
2,7-bis-(2-piperidin-1-yl-ethoxy)-dibenzothiophene;
2,7-bis-(3-azetidin-1-yl-propoxy)-dibenzothiophene;
2,7-bis-(3-pyrrolidin-1-yl-propoxy)-dibenzothiophene;
2,7-bis-(3-piperidin-1-yl-propoxy)-dibenzothiophene;
2,7-bis-(2-trimethylammoniumethoxy)-dibenzothiophene;
2,7-bis-(3-trimethylammoniumpropoxy)-dibenzothiophene;
2,8-bis-(2-aminoethoxy)-dibenzothiophene;
2,8-bis-(3-aminopropoxy)-dibenzothiophene;
2,8-bis-(2-methylaminoethoxy)-dibenzothiophene;
2,8-bis-(2-ethylaminoethoxy)-dibenzothiophene;
2,8-bis-(2-n-propylaminoethoxy)-dibenzothiophene;
2,8-bis-(3-methylaminopropoxy)-dibenzothiophene;
2,8-bis-(3-ethylaminopropoxy)-dibenzothiophene;
2,8-bis-(3-n-propylaminopropoxy)-dibenzothiophene;
2,8-bis-(2-dimethylaminoethoxy)-dibenzothiophene;
2,8-bis-(2-diethylaminoethoxy)-dibenzothiophene;
2,8-bis-(2-di-n-propylaminoethoxy)-dibenzothiophene;
2,8-bis-(3-dimethylaminopropoxy)-dibenzothiophene;
2,8-bis-(3-diethylaminopropoxy)-dibenzothiophene;
2,8-bis-(3-di-n-propylaminopropoxy)-dibenzothiophene;
2,8-bis-(2-azetidin-1-yl-ethoxy)-dibenzothiophene;
2,8-bis-(2-pyrrolidin-1-yl-ethoxy)-dibenzothiophene;
2,8-bis-(2-piperidin-1-yl-ethoxy)-dibenzothiophene;
2,8-bis-(3-azetidin-1-yl-propoxy)-dibenzothiophene;
2,8-bis-(3-pyrrolidin-1-yl-propoxy)-dibenzothiophene;

2,8-bis-(3-piperidin-1-yl-propoxy)-dibenzothiophene;
2,8-bis-(2-trimethylammoniumethoxy)-dibenzothiophene;
2,8-bis-(3-trimethylammoniumpropoxy)-dibenzothiophene;
3,7-bis-(2-aminoethoxy)-dibenzothiophene-5-oxide;
3,7-bis-(3-aminopropoxy)-dibenzothiophene-5-oxide;
3,7-bis-(2-methylaminoethoxy)-dibenzothiophene-5-oxide;
3,7-bis-(2-ethylaminoethoxy)-dibenzothiophene-5-oxide;
3,7-bis-(2-n-propylaminoethoxy)-dibenzothiophene-5-oxide;
3,7-bis-(3-methylaminopropoxy)-dibenzothiophene-5-oxide;
3,7-bis-(3-ethylaminopropoxy)-dibenzothiophene-5-oxide;
3,7-bis-(3-n-propylaminopropoxy)-dibenzothiophene-5-oxide;
3,7-bis-(2-dimethylaminoethoxy)-dibenzothiophene-5-oxide;
3,7-bis-(2-diethylaminoethoxy)-dibenzothiophene-5-oxide;
3,7-bis-(2-di-n-propylaminoethoxy)-dibenzothiophene-5-oxide;
3,7-bis-(3-dimethylaminopropoxy)-dibenzothiophene-5-oxide;
3,7-bis-(3-diethylaminopropoxy)-dibenzothiophene-5-oxide;
3,7-bis-(3-di-n-propylaminopropoxy)-dibenzothiophene-5-oxide;
3,7-bis-(2-azetidin-1-yl-ethoxy)-dibenzothiophene-5-oxide;
3,7-bis-(2-pyrrolidin-1-yl-ethoxy)-dibenzothiophene-5-oxide;
3,7-bis-(2-piperidin-1-yl-ethoxy)-dibenzothiophene-5-oxide;
3,7-bis-(3-azetidin-1-yl-propoxy)-dibenzothiophene-5-oxide;
3,7-bis-(3-pyrrolidin-1-yl-propoxy)-dibenzothiophene-5-oxide;
3,7-bis-(3-piperidin-1-yl-propoxy)-dibenzothiophene-5-oxide;
3,7-bis-(2-trimethylammoniumethoxy)-dibenzothiophene-5-oxide;
3,7-bis-(3-trimethylammoniumpropoxy)-dibenzothiophene-5-oxide;
2,7-bis-(2-aminoethoxy)-dibenzothiophene-5-oxide;
2,7-bis-(3-aminopropoxy)-dibenzothiophene-5-oxide;
2,7-bis-(2-methylaminoethoxy)-dibenzothiophene-5-oxide;
2,7-bis-(2-ethylaminoethoxy)-dibenzothiophene-5-oxide;
2,7-bis-(2-n-propylaminoethoxy)-dibenzothiophene-5-oxide;
2,7-bis-(3-methylaminopropoxy)-dibenzothiophene-5-oxide;
2,7-bis-(3-ethylaminopropoxy)-dibenzothiophene-5-oxide;
2,7-bis-(3-n-propylaminopropoxy)-dibenzothiophene-5-oxide;
2,7-bis-(2-dimethylaminoethoxy)-dibenzothiophene-5-oxide;
2,7-bis-(2-diethylaminoethoxy)-dibenzothiophene-5-oxide;
2,7-bis-(2-di-n-propylaminoethoxy)-dibenzothiophene-5-oxide;
2,7-bis-(3-dimethylaminopropoxy)-dibenzothiophene-5-oxide;
2,7-bis-(3-diethylaminopropoxy)-dibenzothiophene-5-oxide;
2,7-bis-(3-di-n-propylaminopropoxy)-dibenzothiophene-5-oxide;
2,7-bis-(2-azetidin-1-yl-ethoxy)-dibenzothiophene-5-oxide;
2,7-bis-(2-pyrrolidin-1-yl-ethoxy)-dibenzothiophene-5-oxide;
2,7-bis-(2-piperidin-1-yl-ethoxy)-dibenzothiophene-5-oxide;
2,7-bis-(3-azetidin-1-yl-propoxy)-dibenzothiophene-5-oxide;
2,7-bis-(3-pyrrolidin-1-yl-propoxy)-dibenzothiophene-5-oxide;
2,7-bis-(3-piperidin-1-yl-propoxy)-dibenzothiophene-5-oxide;
2,7-bis-(2-trimethylammoniumethoxy)-dibenzothiophene-5-oxide;
2,7-bis-(3-trimethylammoniumpropoxy)-dibenzothiophene-5-oxide;
2,8-bis-(2-aminoethoxy)-dibenzothiophene-5-oxide;
2,8-bis-(3-aminopropoxy)-dibenzothiophene-5-oxide;
2,8-bis-(2-methylaminoethoxy)-dibenzothiophene-5-oxide;
2,8-bis-(2-ethylaminoethoxy)-dibenzothiophene-5-oxide;
2,8-bis-(2-n-propylaminoethoxy)-dibenzothiophene-5-oxide;
2,8-bis-(3-methylaminopropoxy)-dibenzothiophene-5-oxide;
2,8-bis-(3-ethylaminopropoxy)-dibenzothiophene-5-oxide;
2,8-bis-(3-n-propylaminopropoxy)-dibenzothiophene-5-oxide;
2,8-bis-(2-dimethylaminoethoxy)-dibenzothiophene-5-oxide;
2,8-bis-(2-diethylaminoethoxy)-dibenzothiophene-5-oxide;
2,8-bis-(2-di-n-propylaminoethoxy)-dibenzothiophene-5-oxide;
2,8-bis-(3-dimethylaminopropoxy)-dibenzothiophene-5-oxide;
2,8-bis-(3-diethylaminopropoxy)-dibenzothiophene-5-oxide;
2,8-bis-(3-di-n-propylaminopropoxy)-dibenzothiophene-5-oxide;
2,8-bis-(2-azetidin-1-yl-ethoxy)-dibenzothiophene-5-oxide;
2,8-bis-(2-pyrrolidin-1-yl-ethoxy)-dibenzothiophene-5-oxide;
2,8-bis-(2-piperidin-1-yl-ethoxy)-dibenzothiophene-5-oxide;
2,8-bis-(3-azetidin-1-yl-propoxy)-dibenzothiophene-5-oxide;
2,8-bis-(3-pyrrolidin-1-yl-propoxy)-dibenzothiophene-5-oxide;
2,8-bis-(3-piperidin-1-yl-propoxy)-dibenzothiophene-5-oxide;
2,8-bis-(2-trimethylammoniumethoxy)-dibenzothiophene-5-oxide;
2,8-bis-(3-trimethylammoniumpropoxy)-dibenzothiophene-5-oxide;
3,7-bis-(2-aminoethoxy)-dibenzothiophene-5,5-dioxide;
3,7-bis-(3-aminopropoxy)-dibenzothiophene-5,5-dioxide;
3,7-bis-(2-methylaminoethoxy)-dibenzothiophene-5,5-dioxide;
3,7-bis-(2-ethylaminoethoxy)-dibenzothiophene-5,5-dioxide;
3,7-bis-(2-n-propylaminoethoxy)-dibenzothiophene-5,5-dioxide;
3,7-bis-(3-methylaminopropoxy)-dibenzothiophene-5,5-dioxide;
3,7-bis-(3-ethylaminopropoxy)-dibenzothiophene-5,5-dioxide;
3,7-bis-(3-n-propylaminopropoxy)-dibenzothiophene-5,5-dioxide;
3,7-bis-(2-dimethylaminoethoxy)-dibenzothiophene-5,5-dioxide;
3,7-bis-(2-diethylaminoethoxy)-dibenzothiophene-5,5-dioxide;
3,7-bis-(2-di-n-propylaminoethoxy)-dibenzothiophene-5,5-dioxide;

3,7-bis-(3-dimethylaminopropoxy)-dibenzothiophene-5,5-dioxide;
3,7-bis-(3-diethylaminopropoxy)-dibenzothiophene-5,5-dioxide;
3,7-bis-(3-di-n-propylaminopropoxy)-dibenzothiophene-5,5-dioxide;
3,7-bis-(2-azetidin-1-yl-ethoxy)-dibenzothiophene-5,5-dioxide;
3,7-bis-(2-pyrrolidin-1-yl-ethoxy)-dibenzothiophene-5,5-dioxide;
3,7-bis-(2-piperidin-1-yl-ethoxy)-dibenzothiophene-5,5-dioxide;
3,7-bis-(3-azetidin-1-yl-propoxy)-dibenzothiophene-5,5-dioxide;
3,7-bis-(3-pyrrolidin-1-yl-propoxy)-dibenzothiophene-5,5-dioxide;
3,7-bis-(3-piperidin-1-yl-propoxy)-dibenzothiophene-5,5-dioxide;
3,7-bis-(2-trimethylammoniumethoxy)-dibenzothiophene-5,5-dioxide;
3,7-bis-(3-trimethylammoniumpropoxy)-dibenzothiophene-5,5-dioxide;
2,7-bis-(2-aminoethoxy)-dibenzothiophene-5,5-dioxide;
2,7-bis-(3-aminopropoxy)-dibenzothiophene-5,5-dioxide;
2,7-bis-(2-methylaminoethoxy)-dibenzothiophene-5,5-dioxide;
2,7-bis-(2-ethylaminoethoxy)-dibenzothiophene-5,5-dioxide;
2,7-bis-(2-n-propylaminoethoxy)-dibenzothiophene-5,5-dioxide;
2,7-bis-(3-methylaminopropoxy)-dibenzothiophene-5,5-dioxide;
2,7-bis-(3-ethylaminopropoxy)-dibenzothiophene-5,5-dioxide;
2,7-bis-(3-n-propylaminopropoxy)-dibenzothiophene-5,5-dioxide;
2,7-bis-(2-dimethylaminoethoxy)-dibenzothiophene-5,5-dioxide;
2,7-bis-(2-diethylaminoethoxy)-dibenzothiophene-5,5-dioxide;
2,7-bis-(2-di-n-propylaminoethoxy)-dibenzothiophene-5,5-dioxide;
2,7-bis-(3-dimethylaminopropoxy)-dibenzothiophene-5,5-dioxide;
2,7-bis-(3-diethylaminopropoxy)-dibenzothiophene-5,5-dioxide;
2,7-bis-(3-di-n-propylaminopropoxy)-dibenzothiophene-5,5-dioxide;
2,7-bis-(2-azetidin-1-yl-ethoxy)-dibenzothiophene-5,5-dioxide;
2,7-bis-(2-pyrrolidin-1-yl-ethoxy)-dibenzothiophene-5,5-dioxide;
2,7-bis-(2-piperidin-1-yl-ethoxy)-dibenzothiophene-5,5-dioxide;
2,7-bis-(3-azetidin-1-yl-propoxy)-dibenzothiophene-5,5-dioxide;
2,7-bis-(3-pyrrolidin-1-yl-propoxy)-dibenzothiophene-5,5-dioxide;
2,7-bis-(3-piperidin-1-yl-propoxy)-dibenzothiophene-5,5-dioxide;
2,7-bis-(2-trimethylammoniumethoxy)-dibenzothiophene-5,5-dioxide;
2,7-bis-(3-trimethylammoniumpropoxy)-dibenzothiophene-5,5-dioxide;
2,8-bis-(2-aminoethoxy)-dibenzothiophene-5,5-dioxide;
2,8-bis-(3-aminopropoxy)-dibenzothiophene-5,5-dioxide;
2,8-bis-(2-methylaminoethoxy)-dibenzothiophene-5,5-dioxide;
2,8-bis-(2-ethylaminoethoxy)-dibenzothiophene-5,5-dioxide;
2,8-bis-(2-n-propylaminoethoxy)-dibenzothiophene-5,5-dioxide;
2,8-bis-(3-methylaminopropoxy)-dibenzothiophene-5,5-dioxide;
2,8-bis-(3-ethylaminopropoxy)-dibenzothiophene-5,5-dioxide;
2,8-bis-(3-n-propylaminopropoxy)-dibenzothiophene-5,5-dioxide;
2,8-bis-(2-dimethylaminoethoxy)-dibenzothiophene-5,5-dioxide;
2,8-bis-(2-diethylaminoethoxy)-dibenzothiophene-5,5-dioxide;
2,8-bis-(2-di-n-propylaminoethoxy)-dibenzothiophene-5,5-dioxide;
2,8-bis-(3-dimethylaminopropoxy)-dibenzothiophene-5,5-dioxide;
2,8-bis-(3-diethylaminopropoxy)-dibenzothiophene-5,5-dioxide;
2,8-bis-(3-di-n-propylaminopropoxy)-dibenzothiophene-5,5-dioxide;
2,8-bis-(2-azetidin-1-yl-ethoxy)-dibenzothiophene-5,5-dioxide;
2,8-bis-(2-pyrrolidin-1-yl-ethoxy)-dibenzothiophene-5,5-dioxide;
2,8-bis-(2-piperidin-1-yl-ethoxy)-dibenzothiophene-5,5-dioxide;
2,8-bis-(3-azetidin-1-yl-propoxy)-dibenzothiophene-5,5-dioxide;
2,8-bis-(3-pyrrolidin-1-yl-propoxy)-dibenzothiophene-5,5-dioxide;
2,8-bis-(3-piperidin-1-yl-propoxy)-dibenzothiophene-5,5-dioxide;
2,8-bis-(2-trimethylammoniumethoxy)-dibenzothiophene-5,5-dioxide;
2,8-bis-(3-trimethylammoniumpropoxy)-dibenzothiophene-5,5-dioxide;
2,7-bis-(2-aminoethoxy)-9H-carbazole;
2,7-bis-(3-aminopropoxy)-9H-carbazole;
2,7-bis-(2-methylaminoethoxy)-9H-carbazole;
2,7-bis-(2-ethylaminoethoxy)-9H-carbazole;
2,7-bis-(2-n-propylaminoethoxy)-9H-carbazole;
2,7-bis-(3-methylaminopropoxy)-9H-carbazole;
2,7-bis-(3-ethylaminopropoxy)-9H-carbazole;
2,7-bis-(3-n-propylaminopropoxy)-9H-carbazole;
2,7-bis-(2-dimethylaminoethoxy)-9H-carbazole;
2,7-bis-(2-diethylaminoethoxy)-9H-carbazole;
2,7-bis-(2-di-n-propylaminoethoxy)-9H-carbazole;
2,7-bis-(3-dimethylaminopropoxy)-9H-carbazole;
2,7-bis-(3-diethylaminopropoxy)-9H-carbazole;
2,7-bis-(3-di-n-propylaminopropoxy)-9H-carbazole;
2,7-bis-(2-azetidin-1-yl-ethoxy)-9H-carbazole;
2,7-bis-(2-pyrrolidin-1-yl-ethoxy)-9H-carbazole;
2,7-bis-(2-piperidin-1-yl-ethoxy)-9H-carbazole;
2,7-bis-(3-azetidin-1-yl-propoxy)-9H-carbazole;
2,7-bis-(3-pyrrolidin-1-yl-propoxy)-9H-carbazole;
2,7-bis-(3-piperidin-1-yl-propoxy)-9H-carbazole;
2,7-bis-(2-trimethylammoniumethoxy)-9H-carbazole;
2,7-bis-(3-trimethylammoniumpropoxy)-9H-carbazole;
2,6-bis-(2-aminoethoxy)-9H-carbazole;
2,6-bis-(3-aminopropoxy)-9H-carbazole;
2,6-bis-(2-methylaminoethoxy)-9H-carbazole;
2,6-bis-(2-ethylaminoethoxy)-9H-carbazole;
2,6-bis-(2-n-propylaminoethoxy)-9H-carbazole;

2,6-bis-(3-methylaminopropoxy)-9H-carbazole;
2,6-bis-(3-ethylaminopropoxy)-9H-carbazole;
2,6-bis-(3-n-propylaminopropoxy)-9H-carbazole;
2,6-bis-(2-dimethylaminoethoxy)-9H-carbazole;
2,6-bis-(2-diethylaminoethoxy)-9H-carbazole;
2,6-bis-(2-di-n-propylaminoethoxy)-9H-carbazole;
2,6-bis-(3-dimethylaminopropoxy)-9H-carbazole;
2,6-bis-(3-diethylaminopropoxy)-9H-carbazole;
2,6-bis-(3-di-n-propylaminopropoxy)-9H-carbazole;
2,6-bis-(2-azetidin-1-yl-ethoxy)-9H-carbazole;
2,6-bis-(2-pyrrolidin-1-yl-ethoxy)-9H-carbazole;
2,6-bis-(2-piperidin-1-yl-ethoxy)-9H-carbazole;
2,6-bis-(3-azetidin-1-yl-propoxy)-9H-carbazole;
2,6-bis-(3-pyrrolidin-1-yl-propoxy)-9H-carbazole;
2,6-bis-(3-piperidin-1-yl-propoxy)-9H-carbazole;
2,6-bis-(2-trimethylammoniumethoxy)-9H-carbazole;
2,6-bis-(3-trimethylammoniumpropoxy)-9H-carbazole;
3,6-bis-(2-aminoethoxy)-9H-carbazole;
3,6-bis-(3-aminopropoxy)-9H-carbazole;
3,6-bis-(2-methylaminoethoxy)-9H-carbazole;
3,6-bis-(2-ethylaminoethoxy)-9H-carbazole;
3,6-bis-(2-n-propylaminoethoxy)-9H-carbazole;
3,6-bis-(3-methylaminopropoxy)-9H-carbazole;
3,6-bis-(3-ethylaminopropoxy)-9H-carbazole;
3,6-bis-(3-n-propylaminopropoxy)-9H-carbazole;
3,6-bis-(2-dimethylaminoethoxy)-9H-carbazole;
3,6-bis-(2-diethylaminoethoxy)-9H-carbazole;
3,6-bis-(2-di-n-propylaminoethoxy)-9H-carbazole;
3,6-bis-(3-dimethylaminopropoxy)-9H-carbazole;
3,6-bis-(3-diethylaminopropoxy)-9H-carbazole;
3,6-bis-(3-di-n-propylaminopropoxy)-9H-carbazole;
3,6-bis-(2-azetidin-1-yl-ethoxy)-9H-carbazole;
3,6-bis-(2-pyrrolidin-1-yl-ethoxy)-9H-carbazole;
3,6-bis-(2-piperidin-1-yl-ethoxy)-9H-carbazole;
3,6-bis-(3-azetidin-1-yl-propoxy)-9H-carbazole;
3,6-bis-(3-pyrrolidin-1-yl-propoxy)-9H-carbazole;
3,6-bis-(3-piperidin-1-yl-propoxy)-9H-carbazole;
3,6-bis-(2-trimethylammoniumethoxy)-9H-carbazole;
3,6-bis-(3-trimethylammoniumpropoxy)-9H-carbazole;
2,7-bis-(2-aminoethoxy)-9-methyl-9H-carbazole;
2,7-bis-(3-aminopropoxy)-9-methyl-9H-carbazole;
2,7-bis-(2-methylaminoethoxy)-9-methyl-9H-carbazole;
2,7-bis-(2-ethylaminoethoxy)-9-methyl-9H-carbazole;
2,7-bis-(2-n-propylaminoethoxy)-9-methyl-9H-carbazole;
2,7-bis-(3-methylaminopropoxy)-9-methyl-9H-carbazole;
2,7-bis-(3-ethylaminopropoxy)-9-methyl-9H-carbazole;
2,7-bis-(3-n-propylaminopropoxy)-9-methyl-9H-carbazole;
2,7-bis-(2-dimethylaminoethoxy)-9-methyl-9H-carbazole;
2,7-bis-(2-diethylaminoethoxy)-9-methyl-9H-carbazole;
2,7-bis-(2-di-n-propylaminoethoxy)-9-methyl-9H-carbazole;
2,7-bis-(3-dimethylaminopropoxy)-9-methyl-9H-carbazole;
2,7-bis-(3-diethylaminopropoxy)-9-methyl-9H-carbazole;
2,7-bis-(3-di-n-propylaminopropoxy)-9-methyl-9H-carbazole;
2,7-bis-(2-azetidin-1-yl-ethoxy)-9-methyl-9H-carbazole;
2,7-bis-(2-pyrrolidin-1-yl-ethoxy)-9-methyl-9H-carbazole;
2,7-bis-(2-piperidin-1-yl-ethoxy)-9-methyl-9H-carbazole;
2,7-bis-(3-azetidin-1-yl-propoxy)-9-methyl-9H-carbazole;
2,7-bis-(3-pyrrolidin-1-yl-propoxy)-9-methyl-9H-carbazole;
2,7-bis-(3-piperidin-1-yl-propoxy)-9-methyl-9H-carbazole;
2,7-bis-(2-trimethylammoniumethoxy)-9-methyl-9H-carbazole;
2,7-bis-(3-trimethylammoniumpropoxy)-9-methyl-9H-carbazole;
2,6-bis-(2-aminoethoxy)-9-methyl-9H-carbazole;
2,6-bis-(3-aminopropoxy)-9-methyl-9H-carbazole;
2,6-bis-(2-methylaminoethoxy)-9-methyl-9H-carbazole;
2,6-bis-(2-ethylaminoethoxy)-9-methyl-9H-carbazole;
2,6-bis-(2-n-propylaminoethoxy)-9-methyl-9H-carbazole;
2,6-bis-(3-methylaminopropoxy)-9-methyl-9H-carbazole;
2,6-bis-(3-ethylaminopropoxy)-9-methyl-9H-carbazole;
2,6-bis-(3-n-propylaminopropoxy)-9-methyl-9H-carbazole;
2,6-bis-(2-dimethylaminoethoxy)-9-methyl-9H-carbazole;
2,6-bis-(2-diethylaminoethoxy)-9-methyl-9H-carbazole;
2,6-bis-(2-di-n-propylaminoethoxy)-9-methyl-9H-carbazole;
2,6-bis-(3-dimethylaminopropoxy)-9-methyl-9H-carbazole;
2,6-bis-(3-diethylaminopropoxy)-9-methyl-9H-carbazole;
2,6-bis-(3-di-n-propylaminopropoxy)-9-methyl-9H-carbazole;
2,6-bis-(2-azetidin-1-yl-ethoxy)-9-methyl-9H-carbazole;
2,6-bis-(2-pyrrolidin-1-yl-ethoxy)-9-methyl-9H-carbazole;
2,6-bis-(2-piperidin-1-yl-ethoxy)-9-methyl-9H-carbazole;
2,6-bis-(3-azetidin-1-yl-propoxy)-9-methyl-9H-carbazole;
2,6-bis-(3-pyrrolidin-1-yl-propoxy)-9-methyl-9H-carbazole;
2,6-bis-(3-piperidin-1-yl-propoxy)-9-methyl-9H-carbazole;
2,6-bis-(2-trimethylammoniumethoxy)-9-methyl-9H-carbazole;
2,6-bis-(3-trimethylammoniumpropoxy)-9-methyl-9H-carbazole;
3,6-bis-(2-aminoethoxy)-9-methyl-9H-carbazole;
3,6-bis-(3-aminopropoxy)-9-methyl-9H-carbazole;
3,6-bis-(2-methylaminoethoxy)-9-methyl-9H-carbazole;
3,6-bis-(2-ethylaminoethoxy)-9-methyl-9H-carbazole;
3,6-bis-(2-n-propylaminoethoxy)-9-methyl-9H-carbazole;
3,6-bis-(3-methylaminopropoxy)-9-methyl-9H-carbazole;
3,6-bis-(3-ethylaminopropoxy)-9-methyl-9H-carbazole;
3,6-bis-(3-n-propylaminopropoxy)-9-methyl-9H-carbazole;
3,6-bis-(2-dimethylaminoethoxy)-9-methyl-9H-carbazole;
3,6-bis-(2-diethylaminoethoxy)-9-methyl-9H-carbazole;
3,6-bis-(2-di-n-propylaminoethoxy)-9-methyl-9H-carbazole;
3,6-bis-(3-dimethylaminopropoxy)-9-methyl-9H-carbazole;
3,6-bis-(3-diethylaminopropoxy)-9-methyl-9H-carbazole;
3,6-bis-(3-di-n-propylaminopropoxy)-9-methyl-9H-carbazole;
3,6-bis-(2-azetidin-1-yl-ethoxy)-9-methyl-9H-carbazole;
3,6-bis-(2-pyrrolidin-1-yl-ethoxy)-9-methyl-9H-carbazole;
3,6-bis-(2-piperidin-1-yl-ethoxy)-9-methyl-9H-carbazole;
3,6-bis-(3-azetidin-1-yl-propoxy)-9-methyl-9H-carbazole;
3,6-bis-(3-pyrrolidin-1-yl-propoxy)-9-methyl-9H-carbazole;
3,6-bis-(3-piperidin-1-yl-propoxy)-9-methyl-9H-carbazole;
3,6-bis-(2-trimethylammoniumethoxy)-9-methyl-9H-carbazole;
3,6-bis-(3-trimethylammoniumpropoxy)-9-methyl-9H-carbazole;
2,7-bis-(2-aminoethoxy)-xanthen-9-one;
2,7-bis-(3-aminopropoxy)-xanthen-9-one;
2,7-bis-(2-methylaminoethoxy)-xanthen-9-one;
2,7-bis-(2-ethylaminoethoxy)-xanthen-9-one;
2,7-bis-(2-n-propylaminoethoxy)-xanthen-9-one;
2,7-bis-(3-methylaminopropoxy)-xanthen-9-one;
2,7-bis-(3-ethylaminopropoxy)-xanthen-9-one;
2,7-bis-(3-n-propylaminopropoxy)-xanthen-9-one;
2,7-bis-(2-dimethylaminoethoxy)-xanthen-9-one;
2,7-bis-(2-diethylaminoethoxy)-xanthen-9-one;
2,7-bis-(2-di-n-propylaminoethoxy)-xanthen-9-one;
2,7-bis-(3-dimethylaminopropoxy)-xanthen-9-one;
2,7-bis-(3-diethylaminopropoxy)-xanthen-9-one;
2,7-bis-(3-di-n-propylaminopropoxy)-xanthen-9-one;

2,7-bis-(2-azetidin-1-yl-ethoxy)-xanthen-9-one;
2,7-bis-(2-pyrrolidin-1-yl-ethoxy)-xanthen-9-one;
2,7-bis-(2-piperidin-1-yl-ethoxy)-xanthen-9-one;
2,7-bis-(3-azetidin-1-yl-propoxy)-xanthen-9-one;
2,7-bis-(3-pyrrolidin-1-yl-propoxy)-xanthen-9-one;
2,7-bis-(3-piperidin-1-yl-propoxy)-xanthen-9-one;
2,7-bis-(2-trimethylammoniumethoxy)-xanthen-9-one;
2,7-bis-(3-trimethylammoniumpropoxy)-xanthen-9-one;
2,6-bis-(2-methylaminoethoxy)-xanthen-9-one;
2,6-bis-(2-ethylaminoethoxy)-xanthen-9-one;
2,6-bis-(2-n-propylaminoethoxy)-xanthen-9-one;
2,6-bis-(3-methylaminopropoxy)-xanthen-9-one;
2,6-bis-(3-ethylaminopropoxy)-xanthen-9-one;
2,6-bis-(3-n-propylaminopropoxy)-xanthen-9-one;
2,6-bis-(2-dimethylaminoethoxy)-xanthen-9-one;
2,6-bis-(2-diethylaminoethoxy)-xanthen-9-one;
2,6-bis-(2-di-n-propylaminoethoxy)-xanthen-9-one;
2,6-bis-(3-dimethylaminopropoxy)-xanthen-9-one;
2,6-bis-(3-diethylaminopropoxy)-xanthen-9-one;
2,6-bis-(3-di-n-propylaminopropoxy)-xanthen-9-one;
2,6-bis-(2-azetidin-1-yl-ethoxy)-xanthen-9-one;
2,6-bis-(2-pyrrolidin-1-yl-ethoxy)-xanthen-9-one;
2,6-bis-(2-piperidin-1-yl-ethoxy)-xanthen-9-one;
2,6-bis-(3-azetidin-1-yl-propoxy)-xanthen-9-one;
2,6-bis-(3-pyrrolidin-1-yl-propoxy)-xanthen-9-one;
2,6-bis-(3-piperidin-1-yl-propoxy)-xanthen-9-one;
2,6-bis-(2-trimethylammoniumethoxy)-xanthen-9-one;
2,6-bis-(3-trimethylammoniumpropoxy)-xanthen-9-one;
3,6-bis-(2-aminoethoxy)-xanthen-9-one;
3,6-bis-(3-aminopropoxy)-xanthen-9-one;
3,6-bis-(2-methylaminoethoxy)-xanthen-9-one;
3,6-bis-(2-ethylaminoethoxy)-xanthen-9-one;
3,6-bis-(2-n-propylaminoethoxy)-xanthen-9-one;
3,6-bis-(3-methylaminopropoxy)-xanthen-9-one;
3,6-bis-(3-ethylaminopropoxy)-xanthen-9-one;
3,6-bis-(3-n-propylaminopropoxy)-xanthen-9-one;
3,6-bis-(2-dimethylaminoethoxy)-xanthen-9-one;
3,6-bis-(2-diethylaminoethoxy)-xanthen-9-one;
3,6-bis-(2-di-n-propylaminoethoxy)-xanthen-9-one;
3,6-bis-(3-dimethylaminopropoxy)-xanthen-9-one;
3,6-bis-(3-diethylaminopropoxy)-xanthen-9-one;
3,6-bis-(3-di-n-propylaminopropoxy)-xanthen-9-one;
3,6-bis-(2-azetidin-1-yl-ethoxy)-xanthen-9-one;
3,6-bis-(2-pyrrolidin-1-yl-ethoxy)-xanthen-9-one;
3,6-bis-(2-piperidin-1-yl-ethoxy)-xanthen-9-one;
3,6-bis-(3-azetidin-1-yl-propoxy)-xanthen-9-one;
3,6-bis-(3-pyrrolidin-1-yl-propoxy)-xanthen-9-one;
3,6-bis-(3-piperidin-1-yl-propoxy)-xanthen-9-one;
3,6-bis-(2-trimethylammoniumethoxy)-xanthen-9-one;
3,6-bis-(3-trimethylammoniumpropoxy)-xanthen-9-one;
2,7-bis-(2-aminoethoxy)-thioxanthen-9-one;
2,7-bis-(3-aminopropoxy)-thioxanthen-9-one;
2,7-bis-(2-methylaminoethoxy)-thioxanthen-9-one;
2,7-bis-(2-ethylaminoethoxy)-thioxanthen-9-one;
2,7-bis-(2-n-propylaminoethoxy)-thioxanthen-9-one;
2,7-bis-(3-methylaminopropoxy)-thioxanthen-9-one;
2,7-bis-(3-ethylaminopropoxy)-thioxanthen-9-one;
2,7-bis-(3-n-propylaminopropoxy)-thioxanthen-9-one;
2,7-bis-(2-dimethylaminoethoxy)-thioxanthen-9-one;
2,7-bis-(2-diethylaminoethoxy)-thioxanthen-9-one;
2,7-bis-(2-di-n-propylaminoethoxy)-thioxanthen-9-one;
2,7-bis-(3-dimethylaminopropoxy)-thioxanthen-9-one;
2,7-bis-(3-diethylaminopropoxy)-thioxanthen-9-one;
2,7-bis-(3-di-n-propylaminopropoxy)-thioxanthen-9-one;
2,7-bis-(2-azetidin-1-yl-ethoxy)-thioxanthen-9-one;
2,7-bis-(2-pyrrolidin-1-yl-ethoxy)-thioxanthen-9-one;
2,7-bis-(2-piperidin-1-yl-ethoxy)-thioxanthen-9-one;
2,7-bis-(3-azetidin-1-yl-propoxy)-thioxanthen-9-one;
2,7-bis-(3-pyrrolidin-1-yl-propoxy)-thioxanthen-9-one;
2,7-bis-(3-piperidin-1-yl-propoxy)-thioxanthen-9-one;
2,7-bis-(2-trimethylammoniumethoxy)-thioxanthen-9-one;
2,7-bis-(3-trimethylammoniumpropoxy)-thioxanthen-9-one;
2,6-bis-(2-methylaminoethoxy)-thioxanthen-9-one;
2,6-bis-(2-ethylaminoethoxy)-thioxanthen-9-one;
2,6-bis-(2-n-propylaminoethoxy)-thioxanthen-9-one;
2,6-bis-(3-methylaminopropoxy)-thioxanthen-9-one;
2,6-bis-(3-ethylaminopropoxy)-thioxanthen-9-one;
2,6-bis-(3-n-propylaminopropoxy)-thioxanthen-9-one;
2,6-bis-(2-dimethylaminoethoxy)-thioxanthen-9-one;
2,6-bis-(2-diethylaminoethoxy)-thioxanthen-9-one;
2,6-bis-(2-di-n-propylaminoethoxy)-thioxanthen-9-one;
2,6-bis-(3-dimethylaminopropoxy)-thioxanthen-9-one;
2,6-bis-(3-diethylaminopropoxy)-thioxanthen-9-one;
2,6-bis-(3-di-n-propylaminopropoxy)-thioxanthen-9-one;
2,6-bis-(2-azetidin-1-yl-ethoxy)-thioxanthen-9-one;
2,6-bis-(2-pyrrolidin-1-yl-ethoxy)-thioxanthen-9-one;
2,6-bis-(2-piperidin-1-yl-ethoxy)-thioxanthen-9-one;
2,6-bis-(3-azetidin-1-yl-propoxy)-thioxanthen-9-one;
2,6-bis-(3-pyrrolidin-1-yl-propoxy)-thioxanthen-9-one;
2,6-bis-(3-piperidin-1-yl-propoxy)-thioxanthen-9-one;
2,6-bis-(2-trimethylammoniumethoxy)-thioxanthen-9-one;
2,6-bis-(3-trimethylammoniumpropoxy)-thioxanthen-9-one;
3,6-bis-(2-aminoethoxy)-thioxanthen-9-one;
3,6-bis-(3-aminopropoxy)-thioxanthen-9-one;
3,6-bis-(2-methylaminoethoxy)-thioxanthen-9-one;
3,6-bis-(2-ethylaminoethoxy)-thioxanthen-9-one;
3,6-bis-(2-n-propylaminoethoxy)-thioxanthen-9-one;
3,6-bis-(3-methylaminopropoxy)-thioxanthen-9-one;
3,6-bis-(3-ethylaminopropoxy)-thioxanthen-9-one;
3,6-bis-(3-n-propylaminopropoxy)-thioxanthen-9-one;
3,6-bis-(2-dimethylaminoethoxy)-thioxanthen-9-one;
3,6-bis-(2-diethylaminoethoxy)-thioxanthen-9-one;
3,6-bis-(2-di-n-propylaminoethoxy)-thioxanthen-9-one;
3,6-bis-(3-dimethylaminopropoxy)-thioxanthen-9-one;
3,6-bis-(3-diethylaminopropoxy)-thioxanthen-9-one;
3,6-bis-(3-di-n-propylaminopropoxy)-thioxanthen-9-one;
3,6-bis-(2-azetidin-1-yl-ethoxy)-thioxanthen-9-one;
3,6-bis-(2-pyrrolidin-1-yl-ethoxy)-thioxanthen-9-one;
3,6-bis-(2-piperidin-1-yl-ethoxy)-thioxanthen-9-one;
3,6-bis-(3-azetidin-1-yl-propoxy)-thioxanthen-9-one;
3,6-bis-(3-pyrrolidin-1-yl-propoxy)-thioxanthen-9-one;
3,6-bis-(3-piperidin-1-yl-propoxy)-thioxanthen-9-one;
3,6-bis-(2-trimethylammoniumethoxy)-thioxanthen-9-one;
3,6-bis-(3-trimethylammoniumpropoxy)-thioxanthen-9-one;
2,7-bis-(2-aminoethoxy)-10H-acridine-9-one;
2,7-bis-(3-aminopropoxy)-10H-acridine-9-one;
2,7-bis-(2-methylaminoethoxy)-10H-acridine-9-one;
2,7-bis-(2-ethylaminoethoxy)-10H-acridine-9-one;
2,7-bis-(2-n-propylaminoethoxy)-10H-acridine-9-one;
2,7-bis-(3-methylaminopropoxy)-10H-acridine-9-one;
2,7-bis-(3-ethylaminopropoxy)-10H-acridine-9-one;
2,7-bis-(3-n-propylaminopropoxy)-10H-acridine-9-one;
2,7-bis-(2-dimethylaminoethoxy)-10H-acridine-9-one;
2,7-bis-(2-diethylaminoethoxy)-10H-acridine-9-one;
2,7-bis-(2-di-n-propylaminoethoxy)-10H-acridine-9-one;
2,7-bis-(3-dimethylaminopropoxy)-10H-acridine-9-one;
2,7-bis-(3-diethylaminopropoxy)-10H-acridine-9-one;
2,7-bis-(3-di-n-propylaminopropoxy)-10H-acridine-9-one;
2,7-bis-(2-azetidin-1-yl-ethoxy)-10H-acridine-9-one;
2,7-bis-(2-pyrrolidin-1-yl-ethoxy)-10H-acridine-9-one;
2,7-bis-(2-piperidin-1-yl-ethoxy)-10H-acridine-9-one;

2,7-bis-(3-azetidin-1-yl-propoxy)-10H-acridine-9-one;
2,7-bis-(3-pyrrolidin-1-yl-propoxy)-10H-acridine-9-one;
2,7-bis-(3-piperidin-1-yl-propoxy)-10H-acridine-9-one;
2,7-bis-(2-trimethylammoniumethoxy)-10H-acridine-9-one;
2,7-bis-(3-trimethylammoniumpropoxy)-10H-acridine-9-one;
2,6-bis-(2-methylaminoethoxy)-10H-acridine-9-one;
2,6-bis-(2-ethylaminoethoxy)-10H-acridine-9-one;
2,6-bis-(2-n-propylaminoethoxy)-10H-acridine-9-one;
2,6-bis-(3-methylaminopropoxy)-10H-acridine-9-one;
2,6-bis-(3-ethylaminopropoxy)-10H-acridine-9-one;
2,6-bis-(3-n-propylaminopropoxy)-10H-acridine-9-one;
2,6-bis-(2-dimethylaminoethoxy)-10H-acridine-9-one;
2,6-bis-(2-diethylaminoethoxy)-10H-acridine-9-one;
2,6-bis-(2-di-n-propylaminoethoxy)-10H-acridine-9-one;
2,6-bis-(3-dimethylaminopropoxy)-10H-acridine-9-one;
2,6-bis-(3-diethylaminopropoxy)-10H-acridine-9-one;
2,6-bis-(3-di-n-propylaminopropoxy)-10H-acridine-9-one;
2,6-bis-(2-azetidin-1-yl-ethoxy)-10H-acridine-9-one;
2,6-bis-(2-pyrrolidin-1-yl-ethoxy)-10H-acridine-9-one;
2,6-bis-(2-piperidin-1-yl-ethoxy)-10H-acridine-9-one;
2,6-bis-(3-azetidin-1-yl-propoxy)-10H-acridine-9-one;
2,6-bis-(3-pyrrolidin-1-yl-propoxy)-10H-acridine-9-one;
2,6-bis-(3-piperidin-1-yl-propoxy)-10H-acridine-9-one;
2,6-bis-(2-trimethylammoniumethoxy)-10H-acridine-9-one;
2,6-bis-(3-trimethylammoniumpropoxy)-10H-acridine-9-one;
3,6-bis-(2-aminoethoxy)-10H-acridine-9-one;
3,6-bis-(3-aminopropoxy)-10H-acridine-9-one;
3,6-bis-(2-methylaminoethoxy)-10H-acridine-9-one;
3,6-bis-(2-ethylaminoethoxy)-10H-acridine-9-one;
3,6-bis-(2-n-propylaminoethoxy)-10H-acridine-9-one;
3,6-bis-(3-methylaminopropoxy)-10H-acridine-9-one;
3,6-bis-(3-ethylaminopropoxy)-10H-acridine-9-one;
3,6-bis-(3-n-propylaminopropoxy)-10H-acridine-9-one;
3,6-bis-(2-dimethylaminoethoxy)-10H-acridine-9-one;
3,6-bis-(2-diethylaminoethoxy)-10H-acridine-9-one;
3,6-bis-(2-di-n-propylaminoethoxy)-10H-acridine-9-one;
3,6-bis-(3-dimethylaminopropoxy)-10H-acridine-9-one;
3,6-bis-(3-diethylaminopropoxy)-10H-acridine-9-one;
3,6-bis-(3-di-n-propylaminopropoxy)-10H-acridine-9-one;
3,6-bis-(2-azetidin-1-yl-ethoxy)-10H-acridine-9-one;
3,6-bis-(2-pyrrolidin-1-yl-ethoxy)-10H-acridine-9-one;
3,6-bis-(2-piperidin-1-yl-ethoxy)-10H-acridine-9-one;
3,6-bis-(3-azetidin-1-yl-propoxy)-10H-acridine-9-one;
3,6-bis-(3-pyrrolidin-1-yl-propoxy)-10H-acridine-9-one;
3,6-bis-(3-piperidin-1-yl-propoxy)-10H-acridine-9-one;
3,6-bis-(2-trimethylammoniumethoxy)-10H-acridine-9-one;
3,6-bis-(3-trimethylammoniumpropoxy)-10H-acridine-9-one;
2,7-bis-(2-aminoethoxy)-10-methyl-10H-acridine-9-one;
2,7-bis-(3-aminopropoxy)-10-methyl-10H-acridine-9-one;
2,7-bis-(2-methylaminoethoxy)-10-methyl-10H-acridine-9-one;
2,7-bis-(2-ethylaminoethoxy)-10-methyl-10H-acridine-9-one;
2,7-bis-(2-n-propylaminoethoxy)-10-methyl-10H-acridine-9-one;
2,7-bis-(3-methylaminopropoxy)-10-methyl-10H-acridine-9-one;
2,7-bis-(3-ethylaminopropoxy)-10-methyl-10H-acridine-9-one;
2,7-bis-(3-n-propylaminopropoxy)-10-methyl-10H-acridine-9-one;
2,7-bis-(2-dimethylaminoethoxy)-10-methyl-10H-acridine-9-one;
2,7-bis-(2-diethylaminoethoxy)-10-methyl-10H-acridine-9-one;
2,7-bis-(2-di-n-propylaminoethoxy)-10-methyl-10H-acridine-9-one;
2,7-bis-(3-dimethylaminopropoxy)-10-methyl-10H-acridine-9-one;
2,7-bis-(3-diethylaminopropoxy)-10-methyl-10H-acridine-9-one;
2,7-bis-(3-di-n-propylaminopropoxy)-10-methyl-10H-acridine-9-one;
2,7-bis-(2-azetidin-1-yl-ethoxy)-10-methyl-10H-acridine-9-one;
2,7-bis-(2-pyrrolidin-1-yl-ethoxy)-10-methyl-10H-acridine-9-one;
2,7-bis-(2-piperidin-1-yl-ethoxy)-10-methyl-10H-acridine-9-one;
2,7-bis-(3-azetidin-1-yl-propoxy)-10-methyl-10H-acridine-9-one;
2,7-bis-(3-pyrrolidin-1-yl-propoxy)-10-methyl-10H-acridine-9-one;
2,7-bis-(3-piperidin-1-yl-propoxy)-10-methyl-10H-acridine-9-one;
2,7-bis-(2-trimethylammoniumethoxy)-10-methyl-10H-acridine-9-one;
2,7-bis-(3-trimethylammoniumpropoxy)-10-methyl-10H-acridine-9-one;
2,6-bis-(2-methylaminoethoxy)-10-methyl-10H-acridine-9-one;
2,6-bis-(2-ethylaminoethoxy)-10-methyl-10H-acridine-9-one;
2,6-bis-(2-n-propylaminoethoxy)-10-methyl-10H-acridine-9-one;
2,6-bis-(3-methylaminopropoxy)-10-methyl-10H-acridine-9-one;
2,6-bis-(3-ethylaminopropoxy)-10-methyl-10H-acridine-9-one;
2,6-bis-(3-n-propylaminopropoxy)-10-methyl-10H-acridine-9-one;
2,6-bis-(2-dimethylaminoethoxy)-10-methyl-10H-acridine-9-one;
2,6-bis-(2-diethylaminoethoxy)-10-methyl-10H-acridine-9-one;
2,6-bis-(2-di-n-propylaminoethoxy)-10-methyl-10H-acridine-9-one;
2,6-bis-(3-dimethylaminopropoxy)-10-methyl-10H-acridine-9-one;
2,6-bis-(3-diethylaminopropoxy)-10-methyl-10H-acridine-9-one;
2,6-bis-(3-di-n-propylaminopropoxy)-10-methyl-10H-acridine-9-one;
2,6-bis-(2-azetidin-1-yl-ethoxy)-10-methyl-10H-acridine-9-one;
2,6-bis-(2-pyrrolidin-1-yl-ethoxy)-10-methyl-10H-acridine-9-one;
2,6-bis-(2-piperidin-1-yl-ethoxy)-10-methyl-10H-acridine-9-one;
2,6-bis-(3-azetidin-1-yl-propoxy)-10-methyl-10H-acridine-9-one;
2,6-bis-(3-pyrrolidin-1-yl-propoxy)-10-methyl-10H-acridine-9-one;
2,6-bis-(3-piperidin-1-yl-propoxy)-10-methyl-10H-acridine-9-one;
2,6-bis-(2-trimethylammoniumethoxy)-10-methyl-10H-acridine-9-one;

2,6-bis-(3-trimethylammoniumpropoxy)-10-methyl-10H-acridine-9-one;
3,6-bis-(2-aminoethoxy)-10-methyl-10H-acridine-9-one;
3,6-bis-(3-aminopropoxy)-10-methyl-10H-acridine-9-one;
3,6-bis-(2-methylaminoethoxy)-10-methyl-10H-acridine-9-one;
3,6-bis-(2-ethylaminoethoxy)-10-methyl-10H-acridine-9-one;
3,6-bis-(2-n-propylaminoethoxy)-10-methyl-10H-acridine-9-one;
3,6-bis-(3-methylaminopropoxy)-10-methyl-10H-acridine-9-one;
3,6-bis-(3-ethylaminopropoxy)-10-methyl-10H-acridine-9-one;
3,6-bis-(3-n-propylaminopropoxy)-10-methyl-10H-acridine-9-one;
3,6-bis-(2-dimethylaminoethoxy)-10-methyl-10H-acridine-9-one;
3,6-bis-(2-diethylaminoethoxy)-10-methyl-10H-acridine-9-one;
3,6-bis-(2-di-n-propylaminoethoxy)-10-methyl-10H-acridine-9-one;
3,6-bis-(3-dimethylaminopropoxy)-10-methyl-10H-acridine-9-one;
3,6-bis-(3-diethylaminopropoxy)-10-methyl-10H-acridine-9-one;
3,6-bis-(3-di-n-propylaminopropoxy)-10-methyl-10H-acridine-9-one;
3,6-bis-(2-azetidin-1-yl-ethoxy)-10-methyl-10H-acridine-9-one;
3,6-bis-(2-pyrrolidin-1-yl-ethoxy)-10-methyl-10H-acridine-9-one;
3,6-bis-(2-piperidin-1-yl-ethoxy)-10-methyl-10H-acridine-9-one;
3,6-bis-(3-azetidin-1-yl-propoxy)-10-methyl-10H-acridine-9-one;
3,6-bis-(3-pyrrolidin-1-yl-propoxy)-10-methyl-10H-acridine-9-one;
3,6-bis-(3-piperidin-1-yl-propoxy)-10-methyl-10H-acridine-9-one;
3,6-bis-(2-trimethylammoniumethoxy)-10-methyl-10H-acridine-9-one;
3,6-bis-(3-trimethylammoniumpropoxy)-10-methyl-10H-acridine-9-one;
3,8-bis-(2-aminoethoxy)-5H-phenanthridin-6-one;
3,8-bis-(3-aminopropoxy)-5H-phenanthridin-6-one;
3,8-bis-(2-methylaminoethoxy)-5H-phenanthridin-6-one;
3,8-bis-(2-ethylaminoethoxy)-5H-phenanthridin-6-one;
3,8-bis-(2-n-propylaminoethoxy)-5H-phenanthridin-6-one;
3,8-bis-(3-methylaminopropoxy)-5H-phenanthridin-6-one;
3,8-bis-(3-ethylaminopropoxy)-5H-phenanthridin-6-one;
3,8-bis-(3-n-propylaminopropoxy)-5H-phenanthridin-6-one;
3,8-bis-(2-dimethylaminoethoxy)-5H-phenanthridin-6-one;
3,8-bis-(2-diethylaminoethoxy)-5H-phenanthridin-6-one;
3,8-bis-(2-di-n-propylaminoethoxy)-5H-phenanthridin-6-one;
3,8-bis-(3-dimethylaminopropoxy)-5H-phenanthridin-6-one;
3,8-bis-(3-diethylaminopropoxy)-5H-phenanthridin-6-one;
3,8-bis-(3-di-n-propylaminopropoxy)-5H-phenanthridin-6-one;
3,8-bis-(2-azetidin-1-yl-ethoxy)-5H-phenanthridin-6-one;
3,8-bis-(2-pyrrolidin-1-yl-ethoxy)-5H-phenanthridin-6-one;
3,8-bis-(2-piperidin-1-yl-ethoxy)-5H-phenanthridin-6-one;
3,8-bis-(3-azetidin-1-yl-propoxy)-5H-phenanthridin-6-one;
3,8-bis-(3-pyrrolidin-1-yl-propoxy)-5H-phenanthridin-6-one;
3,8-bis-(3-piperidin-1-yl-propoxy)-5H-phenanthridin-6-one;
3,8-bis-(2-trimethylammoniumethoxy)-5H-phenanthridin-6-one;
3,8-bis-(3-trimethylammoniumpropoxy)-5H-phenanthridin-6-one;
3,8-bis-(2-aminoethoxy)-5-methyl-5H-phenanthridin-6-one;
3,8-bis-(3-aminopropoxy)-5-methyl-5H-phenanthridin-6-one;
3,8-bis-(2-methylaminoethoxy)-5-methyl-5H-phenanthridin-6-one;
3,8-bis-(2-ethylaminoethoxy)-5-methyl-5H-phenanthridin-6-one;
3,8-bis-(2-n-propylaminoethoxy)-5-methyl-5H-phenanthridin-6-one;
3,8-bis-(3-methylaminopropoxy)-5-methyl-5H-phenanthridin-6-one;
3,8-bis-(3-ethylaminopropoxy)-5-methyl-5H-phenanthridin-6-one;
3,8-bis-(3-n-propylaminopropoxy)-5-methyl-5H-phenanthridin-6-one;
3,8-bis-(2-dimethylaminoethoxy)-5-methyl-5H-phenanthridin-6-one;
3,8-bis-(2-diethylaminoethoxy)-5-methyl-5H-phenanthridin-6-one;
3,8-bis-(2-di-n-propylaminoethoxy)-5-methyl-5H-phenanthridin-6-one;
3,8-bis-(3-dimethylaminopropoxy)-5-methyl-5H-phenanthridin-6-one;
3,8-bis-(3-diethylaminopropoxy)-5-methyl-5H-phenanthridin-6-one;
3,8-bis-(3-di-n-propylaminopropoxy)-5-methyl-5H-phenanthridin-6-one;
3,8-bis-(2-azetidin-1-yl-ethoxy)-5-methyl-5H-phenanthridin-6-one;
3,8-bis-(2-pyrrolidin-1-yl-ethoxy)-5-methyl-5H-phenanthridin-6-one;
3,8-bis-(2-piperidin-1-yl-ethoxy)-5-methyl-5H-phenanthridin-6-one;
3,8-bis-(3-azetidin-1-yl-propoxy)-5-methyl-5H-phenanthridin-6-one;
3,8-bis-(3-pyrrolidin-1-yl-propoxy)-5-methyl-5H-phenanthridin-6-one;
3,8-bis-(3-piperidin-1-yl-propoxy)-5-methyl-5H-phenanthridin-6-one;
3,8-bis-(2-trimethylammoniumethoxy)-5-methyl-5H-phenanthridin-6-one;
3,8-bis-(3-trimethylammoniumpropoxy)-5-methyl-5H-phenanthridin-6-one;
3,8-bis-(2-aminoethoxy)-benzo[c]chromen-6-one;
3,8-bis-(3-aminopropoxy)-benzo[c]chromen-6-one;
3,8-bis-(2-methylaminoethoxy)-benzo[c]chromen-6-one;
3,8-bis-(2-ethylaminoethoxy)-benzo[c]chromen-6-one;
3,8-bis-(2-n-propylaminoethoxy)-benzo[c]chromen-6-one;
3,8-bis-(3-methylaminopropoxy)-benzo[c]chromen-6-one;
3,8-bis-(3-ethylaminopropoxy)-benzo[c]chromen-6-one;
3,8-bis-(3-n-propylaminopropoxy)-benzo[c]chromen-6-one;
3,8-bis-(2-dimethylaminoethoxy)-benzo[c]chromen-6-one;
3,8-bis-(2-diethylaminoethoxy)-benzo[c]chromen-6-one;
3,8-bis-(2-di-n-propylaminoethoxy)-benzo[c]chromen-6-one;
3,8-bis-(3-dimethylaminopropoxy)-benzo[c]chromen-6-one;

3,8-bis-(3-diethylaminopropoxy)-benzo[c]chromen-6-one;
3,8-bis-(3-di-n-propylaminopropoxy)-benzo[c]chromen-6-one;
3,8-bis-(2-azetidin-1-yl-ethoxy)-benzo[c]chromen-6-one;
3,8-bis-(2-pyrrolidin-1-yl-ethoxy)-benzo[c]chromen-6-one;
3,8-bis-(2-piperidin-1-yl-ethoxy)-benzo[c]chromen-6-one;
3,8-bis-(3-azetidin-1-yl-propoxy)-benzo[c]chromen-6-one;
3,8-bis-(3-pyrrolidin-1-yl-propoxy)-benzo[c]chromen-6-one;
3,8-bis-(3-piperidin-1-yl-propoxy)-benzo[c]chromen-6-one;
3,8-bis-(2-trimethylammoniumethoxy)-benzo[c]chromen-6-one;
3,8-bis-(3-trimethylammoniumpropoxy)-benzo[c]chromen-6-one;
2,7-bis-(2-aminoethoxy)-10H-phenanthren-9-one;
2,7-bis-(3-aminopropoxy)-10H-phenanthren-9-one;
2,7-bis-(2-methylaminoethoxy)-10H-phenanthren-9-one;
2,7-bis-(2-ethylaminoethoxy)-10H-phenanthren-9-one;
2,7-bis-(2-n-propylaminoethoxy)-10H-phenanthren-9-one;
2,7-bis-(3-methylaminopropoxy)-10H-phenanthren-9-one;
2,7-bis-(3-ethylaminopropoxy)-10H-phenanthren-9-one;
2,7-bis-(3-n-propylaminopropoxy)-10H-phenanthren-9-one;
2,7-bis-(2-dimethylaminoethoxy)-10H-phenanthren-9-one;
2,7-bis-(2-diethylaminoethoxy)-10H-phenanthren-9-one;
2,7-bis-(2-di-n-propylaminoethoxy)-10H-phenanthren-9-one;
2,7-bis-(3-dimethylaminopropoxy)-10H-phenanthren-9-one;
2,7-bis-(3-diethylaminopropoxy)-10H-phenanthren-9-one;
2,7-bis-(3-di-n-propylaminopropoxy)-10H-phenanthren-9-one;
2,7-bis-(2-azetidin-1-yl-ethoxy)-10H-phenanthren-9-one;
2,7-bis-(2-pyrrolidin-1-yl-ethoxy)-10H-phenanthren-9-one;
2,7-bis-(2-piperidin-1-yl-ethoxy)-10H-phenanthren-9-one;
2,7-bis-(3-azetidin-1-yl-propoxy)-10H-phenanthren-9-one;
2,7-bis-(3-pyrrolidin-1-yl-propoxy)-10H-phenanthren-9-one;
2,7-bis-(3-piperidin-1-yl-propoxy)-10H-phenanthren-9-one;
2,7-bis-(2-trimethylammoniumethoxy)-10H-phenanthren-9-one; and
2,7-bis-(3-trimethylammoniumpropoxy)-10H-phenanthren-9-one;
and pharmaceutically acceptable salts, esters, amides, and prodrugs thereof. References that may be useful in preparing the compounds are Sill, A. D., et al., *J. Med. Chem.*, 1973, 16, 3, 240-245; Andrews, E. R., et al., *J. Med. Chem.*, 1974, 17, 8, 882-886; Albrecht, W. L., et al., *J. Med. Chem.*, 1974, 17, 8, 886-890; Grisar, J. M., et al., *J. Med. Chem.*, 1974, 17, 8, 890-893; Carr, A. A., et al., *J. Med. Chem.*, 1975, 19, 9, 1142-1148; and Albrecht, W. L., et al., *J. Med. Chem.*, 1977, 20, 3, 364-371.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of conditions and disorders related to memory and/or cognition including, for example, attention deficit disorder, attention deficit hyperactivity disorder (ADHD), Alzheimer's disease (AD), mild cognitive impairment, senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Alpha-7 nAChRs also have been implicated in aspects of neurodevelopment, for example neurogenesis of the brain. (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 nAChRs can be useful in preventing or treating conditions or disorders associated with impaired neurodevelopment, for example schizophrenia. (Sawa A., Mol. Med. 9:3-9, 2003).

Schizophrenia is a complex disease that is characterized by abnormalities in perception, cognition, and emotions. Significant evidence implicates the involvement of α7 nAChRs in this disease, including a measured deficit of these receptors in post-mortem patients (Sawa A., Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al, J. Clin. Invest. 110: 527-536, 2002). For example, improved conditions related to inflammation, ischemia, cardiac ischemia, and wound healing, for example in diabetic persons, have been associated with α7 nAChR activity (Jacobi, J., et al., Am. J. Pathol. 161:97-104, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98:2803-2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving inflammation and pain.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reprod. 68: 1348-1353 2003). Consequently, selective α7 agents demonstrate utility for treating fertility disorders.

Compounds of the invention are particularly useful for treating and preventing a condition or disorder affecting memory, cognition, neurodegeneration, neurodevelopment, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

As used in the descriptions of the schemes and the examples, certain abbreviations are intended to have the following meanings: Ac for acetyl; Bu for n-butyl; Bn for benzyl; cat. for catalyst; dba for dibenzylidene acetone; DMF for dimethyl formamide; $Et_2O$ for diethyl ether; EtOH for ethanol; $Et_3N$ for triethylamine; EtOAc for ethyl acetate; HPLC for high pressure liquid chromatography; $^iPr$ for isopropyl; $^iPrOH$ for isopropyl alcohol, $^iPrNEt_2$ for isopropyl diethyl amine, $^iPrOAc$ for isopropyl acetate; LAH for lithium aluminum hydride; Me for methyl; MeOH for methanol; MeCN for acetonitrile, NBS for N-bromosuccinimide; NMP for N-methylpyrrolidine; OAc for acetoxy; ONF for nonaflate or $-OSO_2CF_2CF_2CF_2CF_3$; Pd/C for palladium on carbon; Ph for phenyl; Rh/C for rhodium on carbon; $^tBu$ for tert-butyl; $^tBuO$ for tert-butoxide; TFA for trifluoroacetic acid; and THF for tetrahydrofuran.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the BOC protecting group may be removed by treatment with an acid such as trifluoroacetic acid or hydrochloric acid. The Cbz and Bn protecting groups may be removed by catalytic hydrogenation. The acetyl and trifluoroacetyl protecting groups may be removed by a hydroxide ion.

The methods described below can entail use of various enantiomers. Where the stereochemistry is shown in the Schemes, it is intended for illustrative purposes only.

Scheme 1

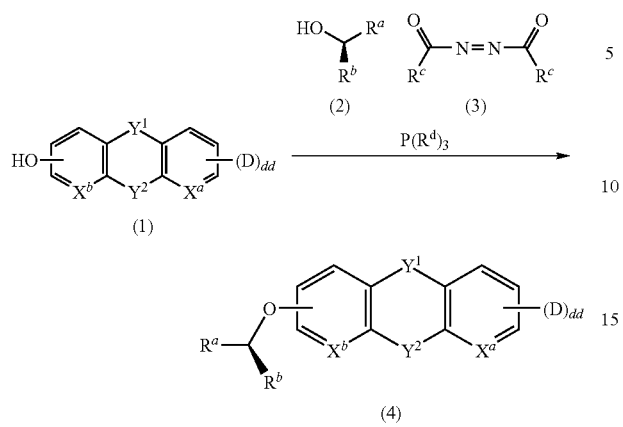

Compounds of formula (4), wherein $X^a$, $X^b$, $Y^1$, and $Y^2$ are as defined for a compound of formula (I) or (II), dd is 0 or 1, D is as defined for group A or B and $R^a$ and $R^b$ are hydrogen, alkyl, heterocycloalkyl, or form a cyclic group of formula as shown for group (a), (b), or (c) for compounds of formula (I) or (II), can be prepared as shown in Scheme 1. A hydroxylated tricyclic core is treated under standard Mitsunobu reaction conditions with a desired alcohol (2) using a dialkyl azodicarboxylate reagent (3), wherein $R^c$ is alkoxy or alkylamino, and a reagent of the formula $P(R^d)_3$, wherein $R^d$ is phenyl or butyl, as described in the art to provide compounds of formula (4). Suitable conditions for the reaction are further described in Hughes, D. L., *Org. React.*, 1992, 42, 335; Tusonda, T., et al., *Tetrahedron Lett.*, 1993, 34, 1639; and Tunoori, A. R., et al., *Tetrahedron Lett.*, 1998, 39, 8751.

Scheme 2

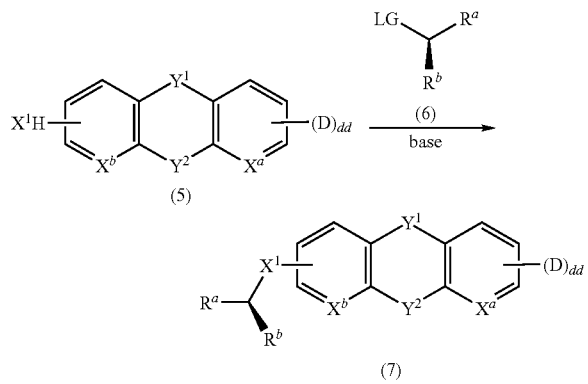

Compounds of formula (7), wherein $X^a$, $X^b$, $Y^1$, and $Y^2$ are as defined for a compound of formula (I) or (II), dd is 0 or 1, D is as defined for group A or B and $R^a$ and $R^b$ are hydrogen, alkyl, heterocycloalkyl, or form a cyclic group of formula as shown for group (a), (b), or (c) for compounds of formula (I) or (II), can be prepared as shown in Scheme 2. A substituted tricyclic core of formula (5), wherein $X^1$ is O, S, or —NH—, is reacted with an alkylating reagent of formula (6), wherein LG represents a halide, methanesulfonate, toluenesulfonate, or triflate group, in the presence of a base, to provide compounds of formula (7).

Scheme 3

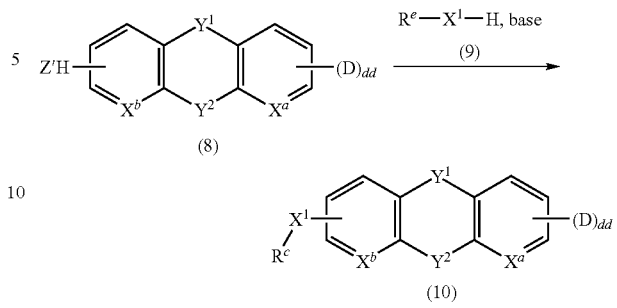

Compounds of formula (10), wherein $X^a$, $X^b$, $Y^1$, and $Y^2$ are as defined for a compound of formula (I) or (II), dd is 0 or 1, D is as defined for group A or B and —$X^1$—$R^e$ is a group of formula (a), (b), (c), (d), (e), (f), or (g) for compounds of formula (I) or (II), can be prepared as shown in Scheme 3. A substituted tricyclic core of formula (6), wherein Z' is a halide, such as bromine, chlorine, fluorine, and iodine, triflate, or nitro, is reacted with a reagent of formula (9), wherein $X^1$ is O, S, or —NH—, in the presence of a base, to provide compounds of formula (10). Suitable conditions for the reaction are further described in U.S. Pat. No. 6,379,590.

Scheme 4

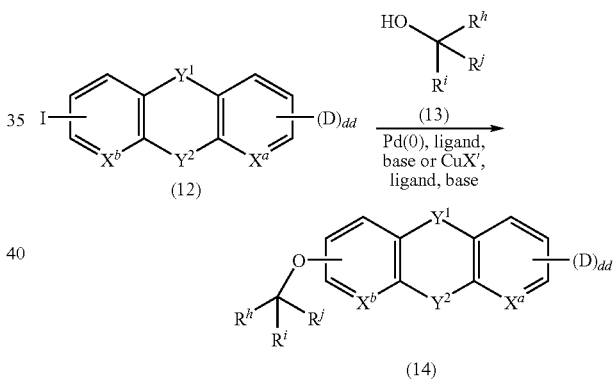

Compounds of formula (14), wherein $X^a$, $X^b$, $Y^1$, and $Y^2$ are as defined for compounds of formula (I) or (II), dd is 0 or 1, D is as defined for a group A or B of formula (I) or (II), and $R^h$, $R^i$, and $R^j$ form a cyclic or acyclic group as defined for a group of formula (a), (b), or (c) in compounds of formula (I) or (II), can be prepared as shown in Scheme 4. An iodinated tricyclic compound of formula (12), wherein dd is 0 or 1, $X^a$, $X^b$, $Y^1$, $Y^2$, and D are as previously defined for compounds of formula (14), treated with a substituted alcohol of formula (13), wherein $R^h$, $R^i$, and $R^j$ are as described for compounds of formula (14), in the presence of a palladium catalyst and a ligand, for example a phosphine ligand, in the presence of a base. Alternatively, the reaction can be carried out by treating the compound of formula (12) with the alcohol reagent of formula (13) in the presence of a copper catalyst, CuX', for example a copper halide, including copper bromide, copper chloride, copper fluoride, and copper iodide, with a ligand in the presence of base. Suitable conditions for the reaction are further described in Muci, A. R., et al., *Topics Current Chem.*, 2002, 219, 131, and Ley, S. V., et al., *Angew. Chem. Int. Ed.*, 2003, 42, 5400.

Scheme 5

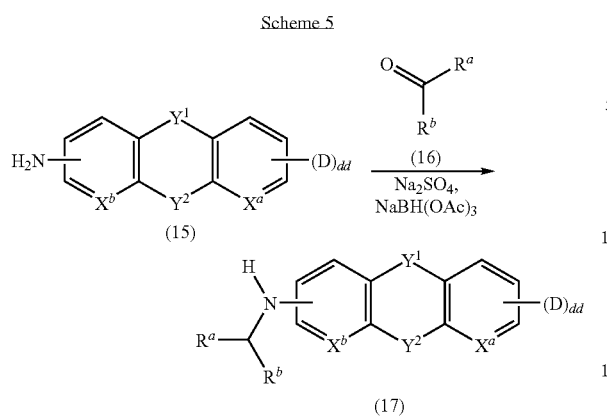

Compounds of the formula (17), wherein $X^a$, $X^b$, $Y^1$, and $Y^2$ are as defined for compounds of formula (I) or (II), dd is 0 or 1, D is as defined for A or B in a compound of formula (I) or (II), and $R^a$ and $R^b$ form the cyclic or acyclic moiety of group (a), (b), or (c) for a compound of formula (I) or (II), prepared as shown in Scheme 5. An amine substituted tricyclic compound of formula (15), wherein dd is 0 or 1, $X^a$, $X^b$, $Y^1$, $Y^2$, and D are as described for compounds of formula (17) can be treated with a ketone of formula (16), wherein $R^a$ and $R^b$ are as defined for compounds of formula (I) or (II), in $Na_2SO_4$ and sodium triacetoxy borohydride, $NaBH(OAc)_3$. Suitable conditions for the reaction are further described in Coe, J., et al., *Tetrahedron Lett.*, 1996, 37, 6045.

Scheme 6

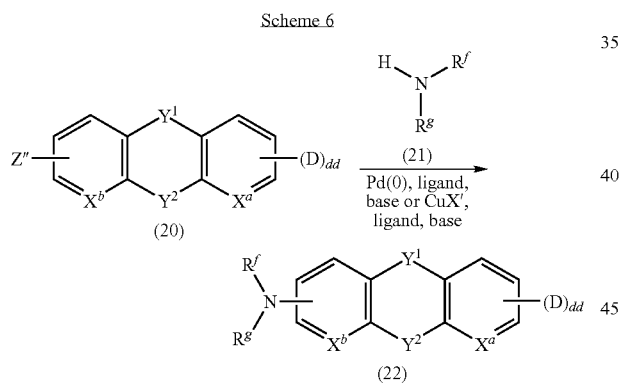

Compounds of formula (22), wherein $X^a$, $X^b$, $Y^1$, and $Y^2$ are as defined for compounds of formula (I) or (II), dd is 0 or 1, D is as defined for a group A or B as defined for compounds of formula (I) or (II), and $R^f$ and $R^g$ form a cyclic moiety of group (d), (e), or (g) as defined for compounds of formula (I) or (II), can be prepared as shown in Scheme 6. A substituted tricyclic starting material of formula (20), wherein Z" is chloride, bromide, iodide, trifluoroacetate, or ONf, i.e. nonaflate or $—OSO_2CF_2CF_2CF_2CF_3$ as described in *J. Org. Chem.*, 2003, 68(25), 9563-9573, can be reacted with an amine reagent of formula (21), wherein $R^f$ and $R^g$ are as defined for a compound of formula (20), to in the presence of a palladium (0) catalyst, and a ligand, for example a phosphine ligand, in the presence of base to provide a compound of formula (22). Alternatively, the compound of formula (20) can be reacted with a copper catalyst, CuX', for example a copper halide, including copper bromide, copper chloride, copper fluoride, and copper iodide, in the presence of base to provide a compound of formula (22). Suitable conditions for the reaction are further described in Muci, A. R., et al., *Topics Current Chem.*, 2002, 219, 131, and Ley, S. V., et al., *Angew. Chem. Int. Ed.*, 2003, 42, 5400.

Scheme 7

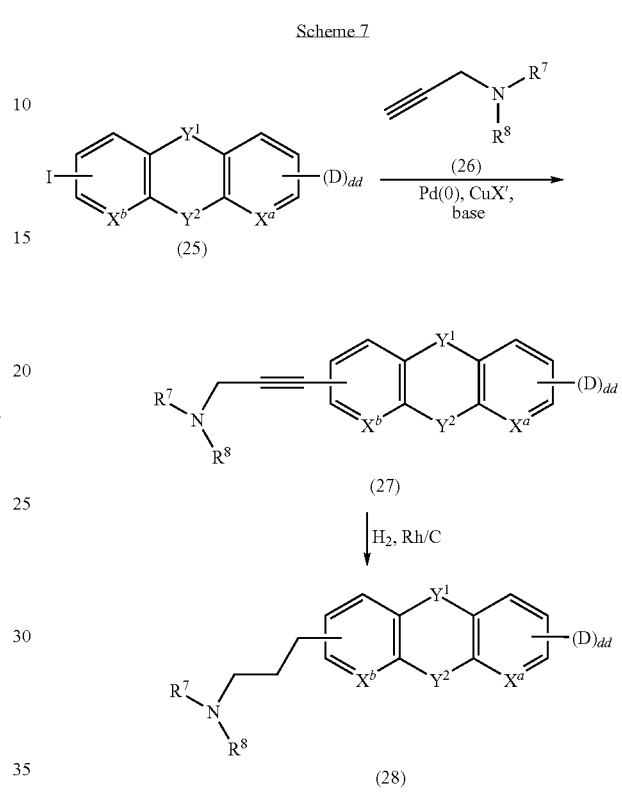

Compounds of formulas (27) and (28), wherein $X^a$, $X^b$, $Y^1$, and $Y^2$ are as defined for compounds of formula (I) or (II), dd is 0 or 1, D is as defined for a group A or B as defined for compounds of formula (I) or (II), and $R^7$ and $R^8$ are as defined for compounds of formula (I) or (II), can be prepared according to Scheme 7. Iodinated tricyclic compounds of formula (25), wherein dd, $X^a$, $X^b$, $Y^1$, $Y^2$, and D are as defined for compounds of formula (28) can be treated with a propargyl amine reagent of formula (26), wherein $R^6$ and $R^7$ are as defined for compounds of formula (I) or (II), in the presence of a palladium (0) catalyst, and a copper halide, CuX', including for example copper bromide, copper chloride, copper fluoride, and copper iodide, in the presence of a base to provide compounds of formula (27). Compounds of formula (27) can be reduced by hydrogenation using a rhodium catalyst on carbon to provide compounds of formula (28).

Scheme 8

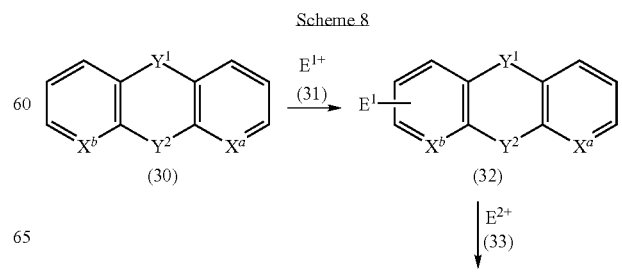

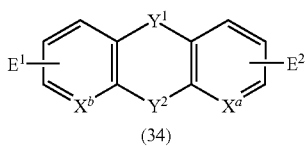

(34)

Compounds of formula (34), wherein $X^a$, $X^b$, $Y^1$, and $Y^2$ are as defined for compounds of formula (I) or (II), $E^1$ and $E^2$ are as defined for $R^x$, or a group A or B, as defined for compounds of formula (I) or (II), can be prepared according to Scheme 8. Unsubstituted tricyclic compounds of formula (30), wherein $X^a$, $X^b$, $Y^1$ and $Y^2$ are as defined for compounds of formula (34), can be treated with an electrophile of formula (31), for example, iodide, bromide, chloride, nitro, or acetyl, to provide compounds of formula (32). Compounds of formula (32) can be further be treated with a second electrophile of formula (33), which is as defined for compounds of formula (31) and can be either the same or different, to provide compounds of formula (34).

Scheme 9

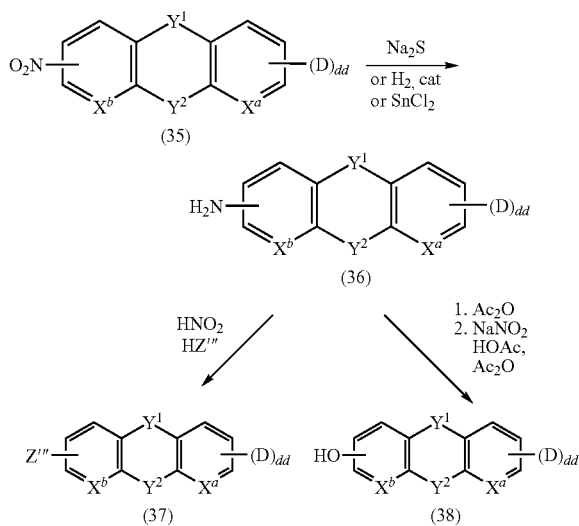

Compounds of formulas (37) and (38), wherein $X^a$, $X^b$, $Y^1$, and $Y^2$ are as defined for compounds of formula (I) or (II), dd is 0 or 1, D as defined for $R^x$, or a group A or B, as defined for compounds of formula (I) or (II), and $Z'''$ is bromide, chloride, fluoride, iodide, and hydroxy, can be prepared according to Scheme 9. Nitro-substituted tricyclic compounds of formula (35), wherein dd, $X^a$, $X^b$, $Y^1$, $Y^2$, and D are as defined for compounds of formulas (37) and (38) can be reduced by treatment sodium sulfide, catalytic hydrogenation, or treatment with tin chloride, to provide amine-substituted compounds of formula (36). Compounds of formula (36) can be reacted with $HNO_2$ and an acid of a suitable halide, or water, to provide compounds of formula (37). Alternatively, compounds of formula (36) can be reacted with $Ac_2O$ followed by $NaNO_2$, acetic acid, and $Ac_2O$ to provide hydroxylated compounds of formula (38). Suitable conditions for the reactions are further described in Perry, P. J., et al., *J. Med. Chem.*, 1999, 42, 2679; Burke, M., et al., *Synth. Commun*, 1976, 6, 371; and Glatzhofer, D. T., et al., *Org. Lett.*, 2002, 4, 2349.

Scheme 10

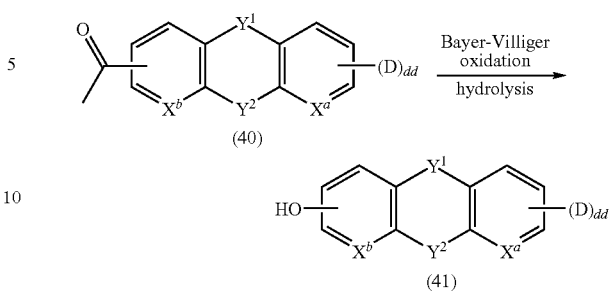

Compounds of formula (41), wherein $X^a$, $X^b$, $Y^1$ and $Y^2$ are as defined for compounds of formula (I) or (II), dd is 0 or 1, and D as defined for $R^x$, or a group A or B, as defined for compounds of formula (I) or (II), can be prepared according to Scheme 10. Tricyclic methyl ketone compounds of formula (40), wherein dd is 0 or 1, $X^a$, $X^b$, $Y^1$, and $Y^2$ are as defined for compounds of formulas (I) or (II), and D as defined for $R^x$, or a group A or B, as defined for compounds of formula (I) or (II), can be oxidized under standard Bayer-Villiger oxidation conditions, followed by hydrolysis, to provide compounds of formula (41). Suitable conditions for the reactions are further described in Burke, M., et al., *Synth. Commun*, 1976, 6, 371.

Scheme 11

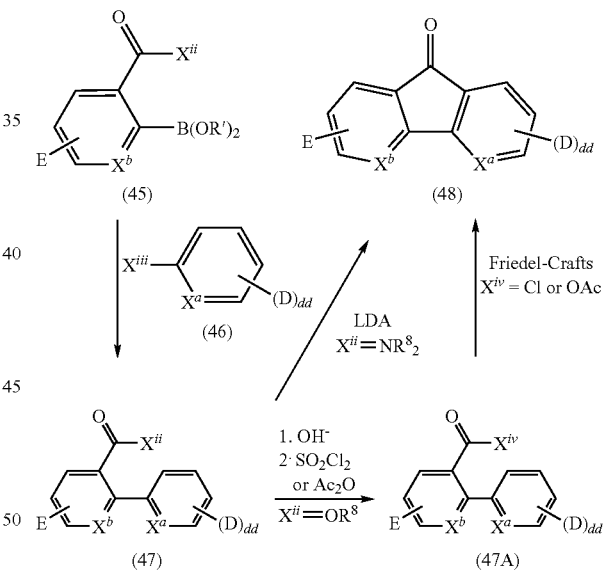

Compounds of formula (48), wherein dd is 0 or 1, $Y^1$ is —C(=O), $Y^2$ is a bond, $X^a$, $X^b$ are as defined for compounds of formula (I) or (II), and D and E are as defined for a group A or B for compounds of formula (I) or (II), can be prepared according to Scheme 11. Boronic acids of aryl amides of formula (45) (prepared as described in Ciske, F. L.; Jones, W. D. Synthesis 1998, 1195; Sharp, M. J.; Cheng, W.; Snieckus, V. *Tetrahedron Lett.* 1987, 28, 5093; and Sharp, M. J.; Snieckus, V. *Tetrahedron Lett.* 1985, 26, 5997), wherein E is as defined for a group A or B for compounds of formula (I) or (II), are coupled with aryl halides of formula (46), wherein $X^{iii}$ is a halide, including chloride, bromide, and iodide, or trifluoromethanesulfonyl, dd is 0 or 1, $X^a$ is C(H) or N, and D is as defined for a group A or B for compounds of formula (I)

or (II), under standard Suzuki coupling reactions, for example a palladium catalyst and a ligand in the presence of base, to provide a compound of formula (47), wherein $X^{ii}$ is $OR^8$ or $NR^8_2$, wherein $R^8$ is hydrogen or alkyl. A compound of formula (47), wherein $X^{ii}$ is $OR^8$ can be transformed into a compound of formula (47A), wherein $X^{iv}$ is chloride, by treatment with hydroxide followed in a second step by thionyl chloride, or into compounds of formula 47(A), wherein $X^{iv}$ is acetoxy, by treatment with hydroxide followed in a second step by acetic anhydride. Compounds of formula (47A) can be treated under Friedel-Crafts conditions when $X^{iv}$ is chloride or acetoxy to provide a compound of formula (48). Compounds of formula (47) can be treated with lithium diisopropylamide (LDA) when $X^{ii}$ is $NR^8_2$ to provide a compound of formula (48). Suitable conditions for the reactions are further described in Ciske, F. L., et al., *Synthesis*, 1998, 1195; Fu, J., et al., *J. Org. Chem.*, 1991, 56, 1683; Kym, P. R., et al., *J. Med. Chem.*, 1996, 39, 4897.

Compounds of formula (54), wherein dd is 0 or 1, $Y^1$ is —$CH_2$—, $Y^2$ is a bond, $X^a$, $X^b$ are as defined in formula (I) or (II), and D and E are as defined for group A or B in a compound of formula (I) or (II) can be prepared as shown in Scheme 13. The ketone group of (48) can be reduced by using a metal hydride or via hydrogenation to provide the hydroxy group of (52), which can be further reduced by the same methods to provide the methylene group of (54). Compounds of formula (54) can be converted to compounds of formula (52) by standard oxidation conditions and further converted to compounds of formula (48) by standard oxidation conditions as well. Suitable conditions for the reactions are further described in Ting, P. C., et al., *Bioorg. Med. Chem. Lett.*, 2002, 12, 2643, and Burke, M., et al., *Synth. Commun*, 1976, 6, 371.

Scheme 12

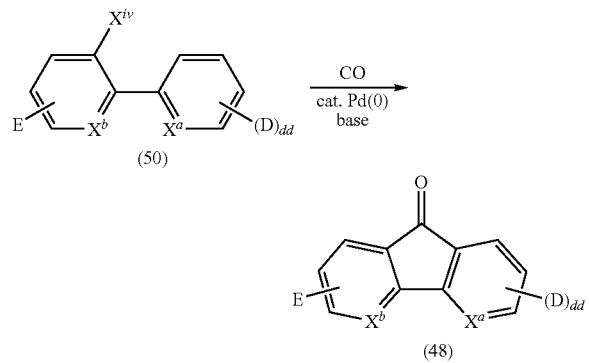

Scheme 14

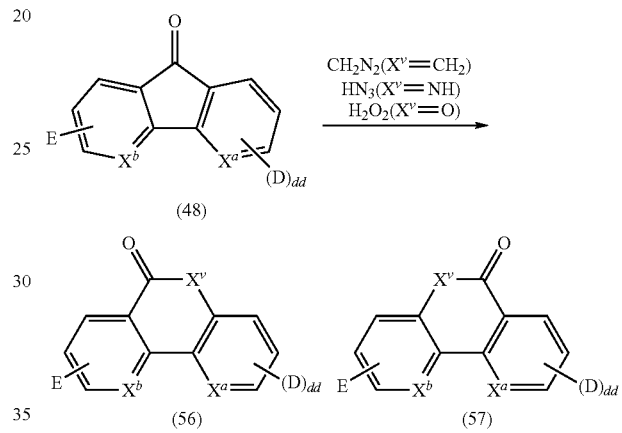

Compounds of formulas (48), wherein dd is 0 or 1, $Y^1$ is —C(=O), $Y^2$ is a bond, $X^a$, $X^b$ are as defined in formula (I) or (II), and D and E are as defined for a group A or B for compounds of formula (I) or (II), also can be prepared according to Scheme 12. A compound of formula (50) (prepared as described in Campo, M. A.; Larock, R. C. *Org. Lett.* 2000, 2, 3675), wherein $X^{iv}$ is bromide or iodide and dd, $X^a$, $X^b$, D and E are as defined for compounds of formula (48), can be treated with carbon monoxide in the presence of a palladium (0) catalyst and base to provide compounds of formula (48). Suitable conditions for the reaction are further described in Campo, M. A., et al., *J. Org. Chem.*, 2002, 67, 5616.

Compounds of formulas (56) and (57), wherein dd is 0 or 1, $Y^1$ is —$X^v$—C(=O)—, $X^v$ is as shown in Scheme 14 above, $Y^2$ is a bond, $X^a$, $X^b$ are as defined in formula (I) or (II), and D and E are as defined for group A or B in a compound of formula (I) or (II) can be prepared as shown in Scheme 14. Compounds of formula (48) can be reacted with $CH_2N_2$, $HN_3$, and $H_2O_2$ to provide the respective compounds of formulas (56) and (57). Suitable conditions for the reactions are further described in U.S. Pat. Nos. 4,169,897; 3,838,131; 3,838,134; 3,932,643; and 4,059,702.

Scheme 13

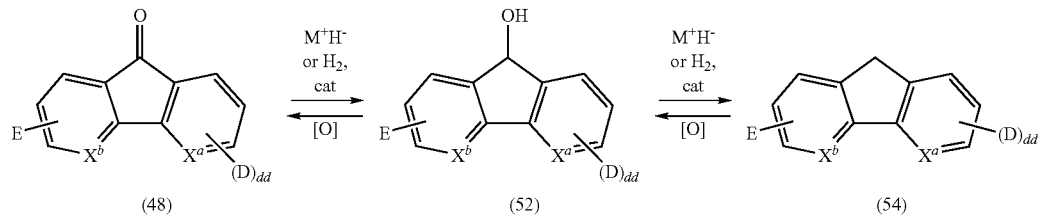

Scheme 15

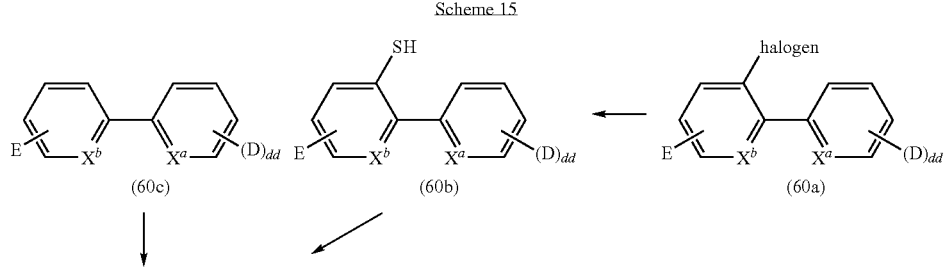

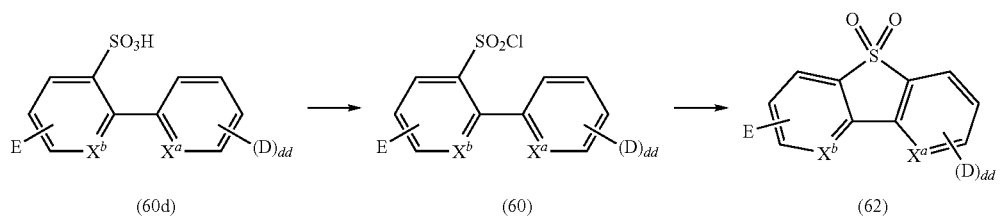

Compounds of formula (62), wherein dd is 0 or 1, $Y^1$ is —S(O)$_2$—, $Y^2$ is a bond, and D and E are as defined for group A or B for compounds of formulas (I) or (II), $X^a$ and $X^b$ are defined as in formula (I) or (II), can be prepared according to Scheme 15. Biphenyl sulfonylchloride compounds of formula (60) are treated with aluminum chloride to provide compounds of formula (62). Suitable conditions for the reaction are further described in Davies, W., et al., *J. Chem. Soc. Abst.*, 1995, 1565. Compounds of formula (60) can be prepared from sulfonic acids of formula (60d) by treatment with a chlorinating agent such as, but are not limited to, phosphorous pentachloride and thionyl chloride. Sulfonic acids of formula (60d) can be obtained by oxidation of thiols of formula (60b) using an oxidizing agent such as, but are not limited to, nitric acid and barium permanganate. Alternatively, sulfonic acids of formula (60d) can be prepared by sulfonation of compounds of formula (60c). Sulfonation can be accomplished with a sulfonating agent such as, but are not limited to, fuming sulfuric acid and concentrated sulfuric acid. Transformation of compounds of formula (60a) to thiols of formula (60b) are well known in the art. One such transformation involves (a) treatment of (60a) with magnesium using conditions known by one skilled in the art to prepare the corresponding Grignard reagents, and (b) treatment of the Grignard reagent with sulfur, followed by acid workup to provide thiols of formula (60b). Alternatively, thiols of formula (60b) can be obtained by treatment of compounds of formula (60a) with sodium sulfhydride (NaSH).

Scheme 16

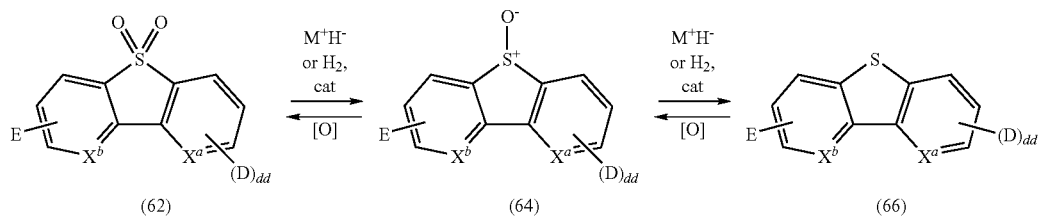

Compounds of formula (66), wherein dd is 0 or 1, $Y^1$ is —S—, $Y^2$ is a bond, D and E are as defined for group A or B in a compound of formula (I) or (II), and $X^a$ and $X^b$ are as defined for compounds of formula (I) or (II), can be prepared as shown in Scheme 16. The sulfonyl group of (62) can be reduced by using a metal halide or via hydrogenation to provide compounds of formula (64), which can be further reduced by the same methods to provide compounds of formula (66). Compounds of formula (66) can be converted to compounds of formula (64) by standard oxidation conditions and further converted to compounds of formula (62) by standard oxidation conditions as well.

tions for the reaction are further described in Familoni, O. B.; Ionica, I.; Bower, J. F.; Snieckus, V. *Synlett* 1997, 1081; Muci et al. *Topics Current Chem.* 2002, 219, 131; and Ley, S. V. et al. *Angew. Chem. Int. Ed.* 2003, 42, 5400. Compounds of formula (70) wherein $Y^2$ is a bond can be prepared from palladium coupling of compounds of formula (69) with compounds of formula (66) wherein $X^{vi}$ is $B(OR^{91})_2$ wherein $R^{91}$ is hydrogen or alkyl, in the presence of a metal catalyst (such as palladium diacetate, tetrakis(triphenylphosphine)palladium (0), tris(dibenzylideneacetone)dipalladium (0) ($Pd_2(dba)_3$), dichloro(di-tert-butylphosphinous acid) palladium (II) dimmer, and [1,1'-bis(diphenylphosphino)ferrocene]

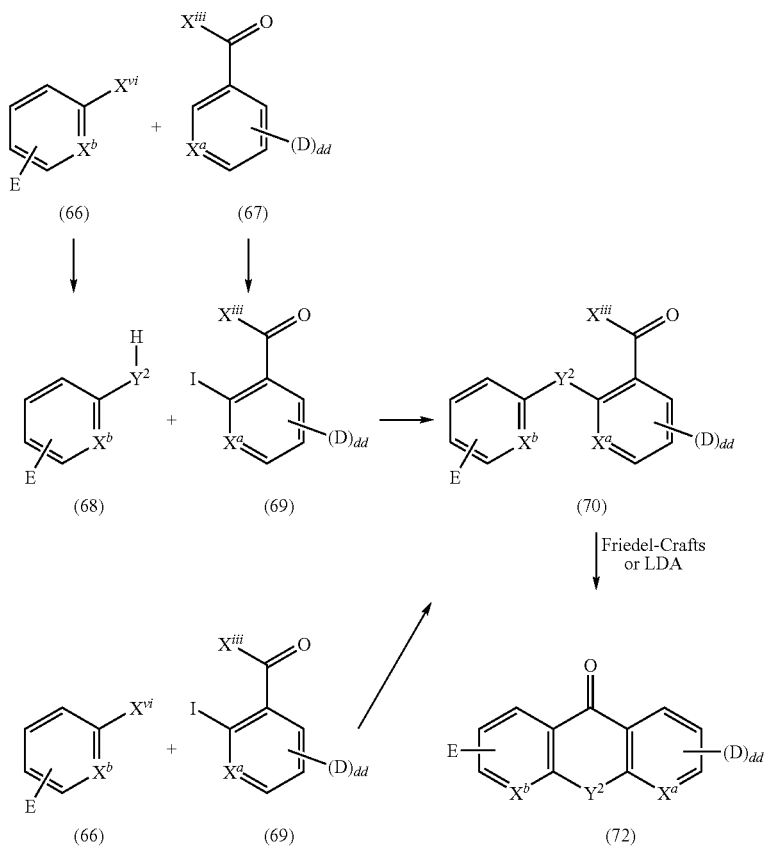

Scheme 17

Compounds of formula (72), wherein dd is 0 or 1, $Y^1$ is —C(=O), $X^a$, $X^b$ and $Y^2$ are as defined for compounds of formulas (I) or (II), and D and E are as defined for group A or B for compounds of formula (I) or (II), can be prepared as shown in Scheme 17. Compounds of formula (70), wherein dd is 0 or 1, $X^{iii}$ is chloride, acetoxy, or $NR_2$, wherein R' is hydrogen or alkyl, and $X^a$, $X^b$, $Y^2$, D, and E are as defined for compounds of formula (72) can be treated under Friedel-Crafts conditions when $X^{iii}$ is chloride or acetoxy, or with lithium diisopropylamide (LDA) when $X^{iii}$ is a $NR'_2$, to provide a compound of formula (72). Suitable conditions for the reactions are further described in Familioni, O. B., et al., *Synlett.*, 1997, 1081; Gobbi, S., et al., *J. Med. Chem.*, 2002, 45, 4931; and Olah, G. A., et al., *Synlett.*, 1999, 7, 1067.

Compounds of formula (70) wherein $Y^2$ is O, S and —N($R^{12}$)— can be prepared by treatment of compounds of formula (68) with compounds of formula (69) using coupling conditions as depicted in Schemes 4 and 6. Suitable condidichloropalladium(II) ($PdCl_2(dppf)$) and the like), a base (such as 0.2 M $K_3PO_4$, $CsCO_3$, CsF, KF, and $Na_2CO_3$ and the like), and optionally with a Pd ligand (such as (dicyclohexylphosphinyl)biphenyl, trifurylphosphine, tris(tert-butyl) phosphine, and triphenylphosphine and the like) added. Alternatively, Compounds of formula (70) wherein $Y^2$ is a bond can be prepared from palladium coupling of compounds of formula (69) with compounds of formula (66) wherein $X^{vi}$ is $Sn(alkyl)_3$ in the presence of a palladium source (such as tris(dibenzylidineacetone)dipalladium (0) or palladium diacetate and the like), and a ligand (such as tri(2-furyl)phosphine or triphenyl arsine).

Compounds of formula (68) wherein $Y^2$ is O or —N($R^{12}$)— can be prepared from compounds of formula (66) wherein $X^{vi}$ is acetyl, halo or nitro using reaction conditions as described in Schemes 9 and 10. Compounds of formula (68) wherein $Y^2$ is S can be obtained from compounds of formula (66) wherein $X^{vi}$ is halogen using conditions for the conversion of compounds of formula (60a) to compounds of formula (60b) as described in Scheme 15.

Iodination of compounds of formula (67) provide compounds of formula (69). Suitable conditions iodination of compounds of formula (67) wherein $X^{iii}$ is $NR_2$ are described in de Silva, S. O.; Reed, J. N.; Billedeau, R. J.; Wang, X.; Norris, D. J.; Snieckus, V. *Tetrahedron* 1992, 48, 4863.

Scheme 18

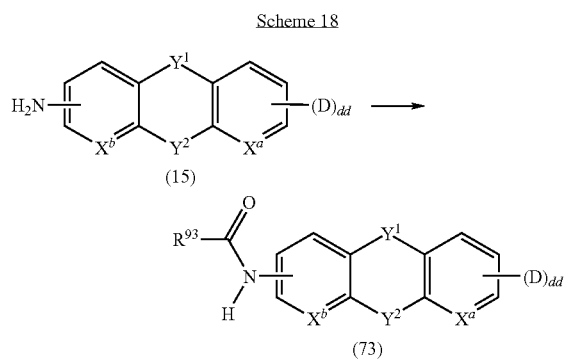

Compounds of formula (73) wherein $R^{93}$ is alkoxy, can be prepared from compounds of formula (15) wherein dd is 0 or 1, $X^a$, $X^b$, $Y^1$ and $Y^2$ are as defined in compounds of formula (I) or (II) and D is as defined for A or B in a compound of formula (I) or (II) by treatment with an acid having formula $R^{93}$COOH, in the presence of a coupling reagent (such as O-(7-azabenzotriazol-1-yl)-N,N,N',N'-tetramethyluronium hexafluorophosphate (HATU) and the like), and optionally in the presence of a base such as, but are not limited to, pyridine, diisopropylethyl amine and N-methyl morpholine. Alternatively, compounds of formula (15) can also be treated with acyl halides of formula $R^{93}$COCl, purchased or prepared by methodologies well known in the art, in the presence of a base such as, but are not limited to, pyridine, diisopropylethyl amine and N-methyl morpholine, to provide compounds of formula (73).

Compounds of formula (73) wherein $R^{93}$ is alkyl, can be prepared from compounds of formula (15) wherein $Y^1$ and $Y^2$ are as defined in compounds of formula (I) or (II) and D is as defined for A or B in a compound of formula (I) or (II) by treatment with an acid chloroformate having formula $R^{93}$OC(O)Cl, in the presence of a base.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like.

Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I).

The compounds of the invention and processes for making compounds for the method of the invention will be better understood by reference to the following Examples, which are intended as an illustration of and not a limitation upon the scope of the invention.

EXAMPLES

Example 1

2,7-Bis[(2R)-1-methylpyrrolidin-2-ylmethoxy]-fluoren-9-one di-p-toluenesulfonate Example 1A 2,7-Bis[(2R)-1-Boc-pyrrolidin-2-ylmethoxy]-fluoren-9-one To a solution of 2,7-dihydroxyfluoren-9-one (0.21 g, 1.0 mmol; see *Synth. Commun.* 1976, 6, 371) and (2R)-(+)-1-Boc-2-pyrrolidinemethanol (0.81 g, 4.0 mmol; Aldrich) in dry THF (10 mL) was added polymer-bound triphenylphosphine (1.3 g, 4.0 mmol; Aldrich) followed by di-tert-butylazodicarboxylate (920 mg, 4.00 mmol; Aldrich). The mixture was stirred overnight (16 h) at room temperature, then filtered through diatomaceous earth, rinsing with ethyl acetate. After concentrating the solution, the residue was purified by flash chromatography (35 g silica gel, 10-30% ethyl acetate-hexane) to afford the title compound (310 mg, 0.54 mmol; 54%). MS (DCI/NH$_3$): m/z 596 (M+18)$^+$.

Example 1B 2,7-Bis[(2R)-pyrrolidin-2-ylmethoxy]-fluoren-9-one

The product of Example 1A (310 mg, 0.54 mmol) in CH$_2$Cl$_2$ (9 mL) was treated with trifluoroacetic acid (3 mL; EM Science) as described in Example 11B, and was purified by flash chromatography (35 g silica gel, eluting with 5-10% of 10% NH$_4$OH/MeOH in CH$_2$Cl$_2$) to afford the title compound (180 mg, 0.48 mmol, 89% yield). MS (DCI/NH$_3$): m/z 379 (M+H)$^+$.

Example 1C 2,7-Bis[(2R)-1-methylpyrrolidin-2-ylmethoxy]-fluoren-9-one

The product of Example 1B (180 mg, 0.48 mmol) was dissolved in dry DMF (5 mL), cooled to 0° C. in an ice bath and treated with 60% sodium hydride (60 mg, 1.4 mmol; Aldrich), followed by iodomethane (0.06 mL, 0.94 mmol, Baker). The mixture was allowed to warm to ambient temperature and stirred for 16 hours, then poured onto ice and extracted with ethyl acetate. The combined organic phases were washed with brine (25 mL), dried over MgSO$_4$, concentrated under reduced pressure, and purified by flash chromatography (35 g silica gel, 1:5:94 NH$_4$OH-MeOH—CH$_2$Cl$_2$) to afford the title compound (50 mg, 0.12 mmol, 26% yield).

Example 1D 2,7-Bis[(2R)-1-methylpyrrolidin-2-ylmethoxy]-fluoren-9-one di-p-toluenesulfonate The product of Example 1C (50 mg, 0.12 mmol) was dissolved in ethyl acetate (5 mL) and ethanol (0.2 mL), then p-toluenesulfonic acid monohydrate (46 mg, 0.24 mmol; Aldrich) was added. After stirring the mixture for 16 hours, the resulting solid was collected by filtration to afford the title compound (68 mg, 0.09 mmol; 74%): $^1$H NMR (300 MHz, methanol-d4): δ 7.68 (4H, d, J=8 Hz), 7.54 (2H, d, J=8 Hz), 7.27-7.14 (8H, m), 4.46 (2H, dd, J=11, 3 Hz), 4.27 (2H, dd, J=11, 7 Hz), 3.88 (2H, m), 3.73 (2H, m), 3.35-3.19 (4H, m), 3.07 (6H, s), 2.48-1.97 (12H, m). MS (DCI/NH$_3$): m/z 407 (M+1)$^+$. Anal. Calcd. for C$_{25}$H$_{30}$N$_2$O$_3$.2C$_7$H$_8$O$_3$S.H$_2$O: C, 60.92; H, 6.29; N, 3.64. Found: C, 61.02; H, 6.25; N, 3.57.

Example 2

2,7-Bis[(2R)-azetidin-2-ylmethoxy]-fluoren-9-one di-p-toluenesulfonate

Example 2A (2R)-1-Boc-2-(methanesulfonyloxymethyl)azetidine

A mixture of (2R)-1-Boc-2-(hydroxymethyl)azetidine (1.5 g, 8.0 mmol; see *Tetrahedron Asym.* 1998, 9, 2791) and triethylamine (3.5 g, 35 mmol; Spectrum) in dry THF (20 mL) was cooled to 0° C., and methanesulfonyl chloride (0.75 mL, 9.7 mmol; Aldrich) was added slowly with stirring. The reaction mixture was allowed to warm to room temperature and stir for 1 hour, then the solid was removed by filtration and the organic phase was concentrated. The residue was dissolved in dichloromethane (40 mL), washed with water (20 mL), and then concentrated to afford the title compound (800 mg. 3.0 mmol; 38% yield). MS (DCI/NH$_3$): 266 (M+1)$^+$, 283 (M+18)$^+$.

Example 2B 2,7-Bis[(2R)-1-Boc-azetidin-2-ylmethoxy]-fluoren-9-one

A mixture of the product of Example 2A (795 mg, 3 mmol), 2,7-dihydroxyfluoren-9-one (212 mg, 1.00 mmol; see *Synth. Commun.* 1976, 6, 371) and powdered potassium hydroxide (135 mg, 2.4 mmol; Fisher) in DMF (10 mL) was heated to 80° C. with stirring for 16 hours. After cooling to room temperature, the reaction mixture was concentrated. Dichloromethane (10 mL) was added, and the solution was washed with water and brine, concentrated and purified by flash chromatography (80 g silica gel, 0-30% isopropanol-hexanes) to afford the title compound (310 mg, 0.56 mmol; 56% yield). MS (DCI/NH$_3$): 568 (M+18)$^+$.

Example 2C 2,7-Bis[(2R)-azetidin-2-ylmethoxy]-fluoren-9-one di-p-toluenesulfonate To a solution of the product of Example 2B (310 mg, 0.56 mmol) in ethyl acetate (10 mL) was added p-toluenesulfonic acid monohydrate (213 mg, 1.12 mmol; Aldrich). The mixture was heated to 60° C. with stirring for 16 hours, and the resulting solid was collected by centrifugation to afford the title compound (313 mg, 0.451 mmol; 81% yield). $^1$H NMR (300 MHz, methanol-d4): δ 7.70 (4H, d, J=8 Hz), 7.54 (2H, d, J=8 Hz), 7.27 (2H, d, J=2 Hz), 7.22 (4H, d, J=8 Hz), 7.17 (2H, dd, J=8, 2 Hz), 4.86 (2H, m), 4.36 (4H, d, J=4 Hz), 4.18-3.98 (4H, m), 2.73-2.60 (4H, m), 2.35 (6H, s). MS (DCI/NH$_3$): m/z 351 (M+1)$^+$. Anal. Calcd. for $C_{21}H_{22}N_2O_3 \cdot 2C_7H_8O_3S$: C, 60.50; H, 5.51; N, 4.03. Found: C, 60.18; H, 5.32; N, 3.91.

Example 3

2,7-Bis[(2R)-1-methylazetidin-2-ylmethoxy]-fluoren-9-one di-p-toluenesulfonate

Example 3A 2,7-Bis[(2R)-1-methylazetidin-2-ylmethoxy]-fluoren-9-one

A mixture of the product of Example 2C (280 mg, 0.403 mmol), formaldehyde (3 mL, 36% aq.; EM Science) and sodium triacetoxyborohydride (400 mg, 1.89 mmol; Aldrich) in water (5 mL) was stirred at room temperature for 16 hours. The mixture was concentrated under vacuum and purified by flash chromatography (80 g silica gel, 1:10:89 NH$_4$OH:MeOH:CH$_2$Cl$_2$) to afford the title compound (150 mg, 0.397 mmol; 98% yield). $^1$H NMR (300 MHz, methanol-d4): δ 7.43 (2H, d, J=8 Hz), 7.14 (2H, d, J=3 Hz), 7.05 (2H, dd, J=8, 3 Hz), 4.10-4.02 (4H, m), 3.54 (2H, m), 3.42 (2H, m), 2.97 (2H, dd, J=17, 9 Hz), 2.43 (6H, s), 2.18-2.04 (4H, m). MS (DCI/NH$_3$): m/z 379 (M+1)$^+$.

Example 3B 2,7-Bis[(2R)-1-methylazetidin-2-ylmethoxy]-fluoren-9-one di-p-toluenesulfonate The product of Example 3A (150 mg, 0.397 mmol) was dissolved in ethyl acetate (5 mL) and ethanol (0.2 mL), and then p-toluenesulfonic acid monohydrate (151 mg, 0.794 mmol; Aldrich) was added. After stirring the mixture for 16 hours, the resulting solid was collected by centrifugation to afford the title compound (202 mg, 0.262 mmol; 66% yield). $^1$H NMR (300 MHz, methanol-d4): δ 7.70 (4H, d, J=8 Hz), 7.54 (2H, d, J=8 Hz), 7.27 (2H, d, J=2 Hz), 7.22 (4H, d, J=8 Hz), 7.18 (2H, dd, J=8, 2 Hz), 4.77 (2H, m), 4.47-4.31 (4H, m), 4.24 (2H, m), 4.01 (2H, dd, J=20, 9 Hz), 3.01 (6H, s), 2.69-2.55 (4H, m), 2.35 (6H, s). MS (DCI/NH$_3$): m/z 379 (M+1)$^+$. Anal. Calcd. for $C_{23}H_{26}N_2O_3 \cdot 2.3C_7H_8O_3S$: C, 60.63; H, 5.78; N, 3.62. Found: C, 60.50; H, 5.59; N, 3.47.

Example 4

2,7-Bis[(3S)-pyrrolidin-3-yloxy]-fluoren-9-one di-p-toluenesulfonate

Example 4A 2,7-Bis[(3S)-1-Boc-pyrrolidin-3-yloxy]-fluoren-9-one

A mixture of 2,7-diiodofluoren-9-one (1.2 g, 2.78 mmol; see J. Chem. Res. (S) 1999, 590), (3S)-1-Boc-3-hydroxypyrrolidine (2.0 g, 10.7 mmol; Omega), copper (I) iodide (53 mg, 0.28 mmol; Aldrich), 1,10-phenanthroline (100 mg, 0.56 mol; Aldrich) and powdered cesium carbonate (3.6 g, 11.0 mmol; Aldrich) in toluene (4 mL) was heated to 110° C. with vigorous stirring for 30 h. After cooling to room temperature, the reaction mixture was filtered through diatomaceous earth, rinsing with ethyl acetate and dichloromethane, and the residue purified by flash chromatography (80 g silica gel, 10-80% ethyl acetate-hexanes) to afford the title compound (466 mg, 0.847 mmol, 30% yield). MS (DCI/NH$_3$): m/z 550 (M)$^+$, 568 (M+18)$^+$.

Example 4B 2,7-Bis[(3S)-pyrrolidin-3-yloxy]-fluoren-9-one di-p-toluenesulfonate

To a solution of the product of Example 4A (437 mg, 0.795 mmol) in ethyl acetate (10 mL) was added p-toluenesulfonic acid monohydrate (310 mg, 1.63 mmol; Aldrich). The mixture was heated at reflux overnight (16 h), and the resulting orange solid was collected by filtration to afford the title compound (517 mg, 0.744 mmol, 94% yield). $^1$H NMR (300 MHz, methanol-d4): δ 7.70 (4H, d, J=8 Hz), 7.52 (2H, d, J=8 Hz), 7.22 (4H, d, J=8 Hz), 7.21 (2H, d, J=2 Hz), 7.12 (2H, dd, J=8, 2 Hz), 5.25 (2H, m), 3.61-3.46 (8H, m), 2.36 (6H, s), 2.37-2.30 (4H, m). MS (DCI/NH$_3$): m/z 351 (M+1)$^+$. Anal. Calcd. for $C_{21}H_{22}N_2O_3 \cdot 2C_7H_8O_3S$: C, 60.50; H, 5.51; N, 4.03. Found: C, 60.64; H, 5.46; N, 3.94.

Example 5

2,7-Bis[(3S)-1-methylpyrrolidin-3-yloxy]-fluoren-9-one di-p-toluenesulfonate

Example 5A 2,7-Bis[(3S)-1-methylpyrrolidin-3-yloxy]-fluoren-9-one

A solution of the product of Example 4B (400 mg, 0.576 mmol) in aqueous formaldehyde (2 mL, 37%; Fisher) was cooled to 0° C. in an ice bath and treated with excess sodium triacetoxyborohydride (366 mg, 1.73 mmol; Aldrich), added in one portion. The reaction mixture was allowed to warm to ambient temperature overnight, then the pH was adjusted with acid to pH<3 and washed with ether. The aqueous phase was raised to pH>10 with 1 N NaOH and extracted with ether (3×). The organic extract was purified by flash chromatography [80 g silica gel, eluting with 2-20% of 10% NH$_4$OH/MeOH in CH$_2$Cl$_2$] to afford the title compound (230 mg, 100% yield). MS (DCI/NH$_3$): m/z 379 (M+1)$^+$.

Example 5B 2,7-Bis[(S)-1-methylpyrrolidin-3-yloxy]fluoren-9-one di-p-toluenesulfonate The product of Example 5A (230 mg, 0.576 mmol) was converted to the title compound (325 mg, 0.45 mmol, 78% yield) according to the procedure described in Example 4B. $^1$H NMR (300 MHz, methanol-d4): δ 7.70 (4H, d, J=8 Hz), 7.53 (2H, d, J=8 Hz), 7.25-7.17 (6H, m), 7.10 (2H, dd, J=8, 2 Hz), 5.26 (2H, m), 4.12-3.74 (4H, m), 3.47-3.19 (4H, m), 3.02 (6H, br s), 2.76-2.62 (1H, m), 2.45-2.18 (9H, m). MS (DCI/NH$_3$): m/z 379 (M+1)$^+$. Anal. Calcd. for $C_{23}H_{26}N_2O_3 \cdot 2C_7H_8O_3S \cdot 0.7H_2O$: C, 60.42; H, 5.95; N, 3.81. Found: C, 60.03; H, 5.88; N, 3.82.

Example 6

2,7-Bis-[(3R)-1-azabicyclo[2.2.2]octan-3-yloxy]-fluoren-9-one di-p-toluenesulfonate

Example 6A

2,7-Bis-[(3R)-1-azabicyclo[2.2.2]octan-3-yloxy]-fluoren-9-one

A mixture of 2,7-diiodofluoren-9-one (170 mg, 0.40 mmol; see *J. Chem. Research* (S), 1999, 590.), (3R)-(–)-quinuclidin-3-ol (318 mg, 2.5 mmol; Acros), copper (I) iodide (38 mg, 0.20 mmol; Aldrich), 1,10-phenanthroline (78 mg, 0.43 mmol; Aldrich) and cesium carbonate (326 mg, 1.0 mmol; Aldrich) in dry toluene (10 mL) was heated to 110° C. and stirred under nitrogen for 60 hours. After cooling to room temperature, the reaction mixture was concentrated and purified by flash chromatography (80 g silica gel, 1:10:89 $NH_4OH$-MeOH—$CH_2Cl_2$) to afford the title compound (71 mg, 0.16 mmol; 41% yield). $^1$H NMR (300 MHz, methanol-d4) δ 7.43 (2H, d, J=8 Hz), 7.10 (2H, d, J=2 Hz), 7.02 (2H, dd, J=8, 2 Hz), 4.56 (2H, m), 3.01-2.72 (12H, m), 2.17 (2H, m), 2.01 (2H, m), 1.81 (2H, m), 1.70 (2H, m), 1.51 (2H, m). MS (DCI/$NH_3$): m/z 431 (M+1)$^+$.

A mixture of 2-[(3R)-1-azabicyclo[2.2.2]octan-3-yloxy]-7-iodofluoren-9-one and 2-[(3R)-1-azabicyclo[2.2.2]octan-3-yloxy]-fluoren-9-one (140 mg, approximately 1:1) was also collected as byproduct and used without further purification. MS (DCI/$NH_3$): m/z 306 (M+1)$^+$, 432 (M+1)$^+$.

Example 6B

2,7-Bis-[(3R)-1-azabicyclo[2.2.2]octan-3-yloxy]-fluoren-9-one di-p-toluenesulfonate The product of Example 6A (71 mg, 0.16 mmol) was converted to the title compound (118 mg, 0.152 mmol; 92% yield) according to the procedure described in Example 1D. $^1$H NMR (300 MHz, methanol-d4): δ 7.70 (4H, d, J=8 Hz), 7.52 (2H, d, J=8 Hz), 7.25-7.18 (6H, m), 7.12 (2H, dd, J=8, 2 Hz), 4.94 (2H, m), 3.82 (2H, dd, J=14, 7 Hz), 3.46-3.32 (10H, m), 2.52 (2H, m), 2.36 (6H, s), 2.30 (2H, m), 2.18-1.83 (6H, m). MS (DCI/$NH_3$): m/z 431 (M+1)$^+$. Anal. Calcd. for $C_{27}H_{30}N_2O_3$·2.3$C_7H_8O_3S$: C, 62.63; H, 5.90; N, 3.39. Found: C, 62.56; H, 5.90; N, 3.31.

Example 7

2,7-Bis[(3S)-1-azabicyclo[2.2.2]octan-3-yloxy]-fluoren-9-one fumarate

Example 7A

2,7-Bis[(3S)-1-azabicyclo[2.2.2]octan-3-yloxy]-fluoren-9-one

To a 0° C. mixture of 2,7-dihydroxyfluoren-9-one (113 mg, 0.533 mmol; see Synth. Commun. 1976, 6, 371), (3R)-quinuclidin-3-ol (280 mg, 2.20 mmol; Acros), and polymer-bound triphenylphosphine (933 mg, 3 mmol/g; Aldrich) in THF (5 mL) was added diethylazodicarboxylate (340 µL, 2.16 mmol; Aldrich). After 1 h, the reaction mixture was allowed to warm to room temperature and was stirred over the weekend. The mixture was filtered through diatomaceous earth, the filter pad rinsed with ethyl acetate, and the organic extracts purified by flash chromatography (35 g silica gel, eluting with 2-10% of 10% $NH_4OH$/MeOH in $CH_2Cl_2$). Acetonitrile was then added to the residue, and the resulting precipitate collected by filtration to yield the title compound (53 mg, 0.12 mmol, 23% yield). MS (DCI/$NH_3$): m/z 431 (M+1)$^+$.

Example 7B

2,7-Bis[(3S)-1-azabicyclo[2.2.2]octan-3-yloxy]-fluoren-9-one fumarate

A solution of the product of Example 7A (53 mg, 0.123 mmol) in ethyl acetate-(containing a few drops of ethanol) was treated with a solution of fumaric acid (28 mg, 0.241 mmol; Aldrich) in ethanol. After stirring for 1 h, the precipitate was collected by filtration, affording the title compound (67 mg, 0.11 mmol, 86% yield). $^1$H NMR (300 MHz, methanol-d4): δ 7.51 (2H, d, J=8 Hz), 7.18 (2H, d, J=2 Hz), 7.11 (2H, dd, J=8, 2 Hz), 6.68 (1.4H, s), 3.74 (2H, dd, J=15, 8 Hz), 3.36-3.18 (10H, m), 2.46 (2H, m), 2.25 (2H, m), 2.14-1.76 (6H, m). MS (DCI/$NH_3$): m/z 431 (M+1)$^+$. Anal. Calcd. for $C_{27}H_{30}N_2O_3$·1.4$C_4H_4O_4$·2.1$H_2O$: C, 62.07; H, 6.36; N, 4.44. Found: C, 61.83; H, 6.09; N, 4.16.

Example 8

2-[(3R)-1-azabicyclo[2.2.2]octan-3-yloxy]-fluoren-9-one p-toluenesulfonate

Example 8A

2-[(3R)-1-azabicyclo[2.2.2]octan-3-yloxy]-fluoren-9-one

A solution of the byproduct mixture from Example 6A (140 mg) in methanol was treated with 10% palladium on carbon (50 mg) under 1 atm hydrogen (balloon) for 16 hours. The catalyst was filtered off and the resulting solution was concentrated to afford the title compound (112 mg, 0.365 mmol). MS (DCI/$NH_3$): m/z 306 (M+1)$^+$.

Example 8B

2-[(3R)-1-azabicyclo[2.2.2]octan-3-yloxy]-fluoren-9-one p-toluenesulfonate

The product of Example 8A (112 mg, 0.365 mmol) was converted to the title compound (187 mg, 0.36 mmol; 100% yield) according to the procedure described in Example 1D. $^1$H NMR (300 MHz, methanol-d4): δ 7.70 (2H, d, J=8 Hz), 7.60-7.48 (4H, m), 7.28 (1H, dd, J=7, 1 Hz), 7.26-7.19 (3H, m), 7.15 (1H, dd, J=8, 2 Hz), 4.96 (1H, m), 3.83 (1H, m), 3.48-3.32 (5H, m), 2.54 (1H, m), 2.36 (3H, s), 2.30 (1H, m), 2.18-1.83 (3H, m). MS (DCI/$NH_3$): m/z 306 (M+1)$^+$. Anal. Calcd. for $C_{20}H_{19}NO_2$·1.2$C_7H_8O_3S$: C, 66.62; H, 5.63; N, 2.74. Found: C, 66.65; H, 5.57; N, 2.81.

Example 9

2-[(3S)-1-azabicyclo[2.2.2]octan-3-yloxy]-fluoren-9-one fumarate

Example 9A

2-[(3S)-1-azabicyclo[2.2.2]octan-3-yloxy]-fluoren-9-one

To a 0° C. mixture of 2-hydroxyfluoren-9-one (196 mg, 1.00 mmol; Aldrich), (3R)-quinuclidin-3-ol (151 mg, 1.20 mmol; Acros), and polymer-bound triphenylphosphine (500 mg, 3 mmol/g; Aldrich) in THF (5 mL) was added diethylazodicarboxylate (200 μL, 1.27 mmol; Aldrich). After 1 h, the reaction mixture was allowed to warm to room temperature and was stirred overnight (16 h). The mixture was filtered through diatomaceous earth, the filter pad rinsed with dichloromethane, and the organic extracts purified twice by flash chromatography (80 g silica gel, eluting with 1-5% of 10% $NH_4OH/MeOH$ in $CH_2Cl_2$) to afford the title compound (104 mg, 0.340 mmol, 34% yield). MS (DCI/$NH_3$): m/z 306 $(M+1)^+$.

Example 9B

2-[(3S)-1-azabicyclo[2.2.2]octan-3-yloxy]-fluoren-9-one fumarate

The product of Example 9A (102 mg, 0.334 mmol) was converted to the title compound (66 mg, 0.16 mmol, 47% yield) according to the procedure described in Example 7B: $^1$H NMR (300 MHz, methanol-d4): δ 7.61-7.56 (3H, m), 7.51 (1H, ddd, J=7, 7, 1 Hz), 7.27 (1H, ddd, J=7, 7, 1 Hz), 7.22 (1H, d, J=2 Hz), 7.14 (1H, dd, J=8, 2 Hz), 6.68 (2H, s), 4.93 (1H, m), 3.79 (1H, ddd, J=10, 8, 2 Hz), 3.42-3.23 (5H, m), 2.51 (1H, m), 2.29 (1H, m), 2.16-1.81 (3H, m). MS (DCI/$NH_3$): m/z 306 $(M+1)^+$. Anal. Calcd. for $C_{20}H_{19}NO_2 \cdot C_4H_4O_4$: C, 68.40; H, 5.50; N, 3.32. Found: C, 68.01; H, 5.47; N, 3.28.

Example 10

2,7-Bis(4-methyl-[1,4]diazepan-1-yl)-fluoren-9-one dihydrochloride

Example 10A 2,7-Bis(4-methyl-[1,4]diazepan-1-yl)-fluoren-9-one

A catalyst solution was prepared by mixing tris(dibenzylideneacetone)dipalladium ($Pd_2(dba)_3$; 36 mg, 0.039 mmol; Alfa) and racemic 2,2'-bis(diphenylphosphino)-1,1'-binaphthyl (BINAP; 62 mg, 0.10 mmol; Strem) in toluene (1 mL) and heating the mixture to 80° C. for 15 min. The solution was cooled, and then added to a mixture of N-methylhomopiperazine (310 μL, 2.50 mmol; Aldrich) and 2,7-dibromofluoren-9-one (338 mg, 1.00 mmol; Aldrich) in toluene (5 mL). Sodium tert-butoxide (200 mg, 2.08 mmol; Aldrich) was then added, and the reaction mixture was purged with nitrogen and heated to 80-85° C. for 4 h. After cooling to room temperature, the mixture was filtered through diatomaceous earth and purified by chromatography (80 g silica gel, eluting with 2-12% of 10% $NH_4OH/MeOH$ in $CH_2Cl_2$) to afford the title compound (273 mg, 0.674 mmol, 67% yield): MS (DCI/$NH_3$): m/z 405 $(M+1)^+$.

Example 10B 2,7-Bis(4-methyl-[1,4]diazepan-1-yl)-fluoren-9-one dihydrochloride

To a solution of the product of Example 10A (273 mg, 0.674 mmol) in ethyl acetate containing a few drops ethanol was added a solution of HCl in dioxane (4 M, 335 μL, 1.34 mmol; Aldrich). After stirring the mixture for 2 h, the solid was collected by filtration and recrystallized from hot EtOH/EtOAc to afford the title compound (193 mg, 0.382 mmol, 57% yield). $^1$H NMR (300 MHz, $D_2O$) δ 7.15 (2H, d, J=8 Hz), 6.79-6.75 (4H, m), 3.77 (4H, t, J=4 Hz), 3.52 (4H, t, J=6 Hz), 3.44 (4H, m), 2.97 (6H, s), 2.27 (4H, m). MS (CI/$NH_3$): m/z 405 $(M+1)^+$. Anal. Calcd. for $C_{25}H_{32}N_4O \cdot 2HCl \cdot 1.5H_2O$: C, 59.52; H, 7.39; N, 11.11. Found: C, 59.26; H, 7.44; N, 10.87.

Example 11

2,7-Bis[3,7-diazabicyclo[3.3.0]octan-3-yl]-fluoren-9-one dihydrochloride

Example 11A 2,7-Bis[N-Boc-3,7-diazabicyclo[3.3.0]octan-3-yl]-fluoren-9-one

A catalyst solution was prepared by mixing tris(dibenzylideneacetone)dipalladium ($Pd_2(dba)_3$; 35 mg, 0.038 mmol; Alfa) and racemic 2,2'-bis(diphenylphosphino)-1,1'-binaphthyl (BINAP; 61 mg, 0.098 mmol; Strem) in toluene (1 mL) and heating the mixture to 80° C. for 15 min. The solution was cooled, and then added to a mixture of 3-Boc-3,7-diazabicyclo[3.3.0]octane (483 mg, 2.28 mmol; see WO 0181347) and 2,7-dibromofluoren-9-one (336 mg, 0.994 mmol; Aldrich) in toluene (5 mL). Sodium tert-butoxide (276 mg, 2.87 mmo; Aldrich) was then added, and the reaction mixture was purged with nitrogen and heated to 80-85° C. overnight (16 h). After cooling to room temperature, the mixture was filtered through diatomaceous earth and purified by chromatography (80 g silica gel, 10-100% EtOAc-hexanes) to afford the title compound (322 mg, 0.537 mmol, 54% yield). MS (DCI/$NH_3$): m/z 601 $(M+1)^+$.

Example 11B 2,7-Bis[3,7-diazabicyclo[3.3.0]octan-3-yl]-fluoren-9-one

A solution of the product of Example 11A (322 mg, 0.537 mmol) in dichloromethane (5 mL) was cooled to 0° C. and treated with trifluoroacetic acid (3 mL). After stirring for 30 min, the reaction mixture was warmed to room temperature and the stirring continued for an additional 30 min. The solution was diluted with dichloromethane, washed with 1 N NaOH (aq), and concentrated to afford the title compound as an oil (225 mg, 0.537 mmol, 100% yield): MS (DCI/$NH_3$): m/z 401 $(M+1)^+$.

Example 11C 2,7-Bis[3,7-diazabicyclo[3.3.0]octan-3-yl]fluoren-9-one dihydrochloride To a stirred solution of the product of Example 11 B (56 mg, 0.14 mmol) in ethyl acetate containing ethanol and methanol was added a solution of HCl in dioxane (4 M; 70 μL, 0.28 mmol; Aldrich). After stirring for 1 h, the purple solid was collected by filtration, affording the title compound (55 mg, 0.12 mmol, 81% yield). $^1$H NMR (300 MHz, $D_2O$): δ 7.24 (2H, d, J=8 Hz), 6.90 (2H, d, J=2 Hz), 6.80 (2H, dd, J=8, 2 Hz), 3.68 (4H, m), 3.47-3.26 (16H, m). MS (DCI/$NH_3$): m/z 401 (M+1)+. Anal. Calcd. for $C_{25}H_{28}N_4O \cdot 2HCl \cdot 0.7H_2O$: C, 61.78; H, 6.51; N, 11.53. Found: C, 61.50; H, 6.32; N, 11.21.

Example 12

2,7-Bis[7-methyl-3,7-diazabicyclo[3.3.0]octan-3-yl] fluoren-9-one dihydrochloride

Example 12A

2,7-Bis[7-methyl-3,7-diazabicyclo[3.3.0]octan-3-yl] fluoren-9-one

To a 0° C. suspension of the product of Example 11B (166 mg, 0.415 mmol) in aq. formaldehyde (37%, 3 mL; Fisher) containing a few drops of methanol was added sodium triacetoxyborohydride (298 mg, 1.41 mmol; Aldrich) in one portion. After 30 min, the reaction mixture was allowed to warm to room temperature and stirring was continued overnight (16 h). The mixture was then diluted with dichloromethane, washed with 1 N NaOH, and the aqueous layer was extracted twice with $CH_2Cl_2$. The combined organic phases were dried over potassium carbonate, filtered, and concentrated. The residue was purified by chromatography (35 g silica gel, eluting with 2-16% of 10% $NH_4OH/MeOH$ in $CH_2Cl_2$) to afford the title compound (136 mg, 0.318 mmol, 76% yield). MS (DCI/$NH_3$): m/z 429 (M+1)+.

Example 12B

2,7-Bis[7-methyl-3,7-diazabicyclo[3.3.0]octan-3-yl]-fluoren-9-one dihydrochloride The product of Example 12A (84 mg, 0.20 mmol) was converted to the title compound (85 mg, 0.17 mmol, 85% yield) according to the procedure described in Example 11C. $^1$H NMR (300 MHz, methanol-d4): δ 7.32 (2H, d, J=8 Hz), 7.01 (2H, s), 6.85 (2H, d, J=8 Hz), 3.97 (2H, m), 3.67-3.54 (6H, m), 3.45-3.15 (10H, m), 2.95 (8H, m). MS (DCI/$NH_3$): m/z 429 (M+1)+. Anal. Calcd. for $C_{27}H_{32}N_4O \cdot 2HCl \cdot 0.6H_2O$: C, 63.30; H, 6.93; N, 10.94. Found: C, 63.09; H, 7.05; N, 10.87.

Example 13

2-[3,7-diazabicyclo[3.3.0]octan-3-yl]-fluoren-9-one p-toluenesulfonate

Example 13A

2-[3-Boc-3,7-diazabicyclo[3.3.0]octan-3-yl]-fluoren-9-one

A mixture of 3-Boc-3,7-diazabicyclo[3.3.0]octane (160 mg, 0.77 mmol; see WO 0181347), 2-bromo-9-fluorenone (200 mg, 0.77 mmol; Aldrich), tris(dibenzylideneacetone) dipalladium (0) ($Pd_2 dba_3$; 21 mg, 0.023 mmol; Strem), racemic-2,2'-bis(diphenylphosphino)-1,1'-binaphthyl (BINAP; 24 mg, 0.039 mmol; Strem) and $Cs_2CO_3$ (500 mg, 1.54 mmol; Aldrich) in 20 mL toluene was warmed to 85° C. and stirred for 16 h. The reaction mixture was cooled to ambient temperature, filtered, concentrated under reduced pressure and purified via column chromatography (silica gel, 50% hexanes/EtOAc) to give the title compound (260 mg, 0.67 mmol, 86% yield). MS (DCI/$NH_3$) m/z 391 (M+H)+.

Example 13B

2-[3,7-diazabicyclo[3.3.0]octan-3-yl]-fluoren-9-one

The product of Example 13A (0.26 g, 0.66 mmol) in $CH_2Cl_2$ (7 mL) was treated with trifluoroacetic acid (5 mL; EM Science) as described in Example 11B to give the title compound (230 mg, 100% yield), which was carried on without purification.

Example 13C

2-[3,7-diazabicyclo[3.3.0]octan-3-yl]-fluoren-9-one p-toluenesulfonate

To the product of Example 13B (50.mg, 0.17 mmol) in 10% $CH_3OH/EtOAc$ (2 mL) was added p-toluenesulfonic acid (33 mg, 0.17 mmol; Aldrich) in 10% $CH_3OH/EtOAc$ (1 mL). A precipitate formed which was isolated via filtration to give the title compound (68 mg, 0.13 mmol, 77% yield). $^1$H NMR (methanol-$d_4$, 300 MHz): δ 7.70 (2H, m), 7.50 (1H, dt, J=7, 1 Hz), 7.43-7.48 (3H, m), 7.22 (2H, m), 7.17 (1H, dt, J=9, 4 Hz), 7.00 (1H, d, J=3 Hz), 6.83 (1H, dd, J=8, 2 Hz), 3.60 (2H, m), 3.52 (2H, m), 3.41 (2H, m), 3.20-3.27 (4H, m), 2.36 (3H, s). MS (DCI/$NH_3$): m/z 291 (M+H)+. Anal. Calcd. for $C_{19}H_{18}N_2O \cdot 1.25C_7H_8O_3S \cdot 0.8H_2O$: C, 64.09; H, 5.74; N, 5.39. Found: C, 63.71; H, 5.47; N, 5.80.

Example 14

2-[7-Methyl-3,7-diazabicyclo[3.3.0]octan-3-yl]-fluoren-9-one l-tartrate

Example 14A

2-[7-Methyl-3,7-diazabicyclo[3.3.0]octan-3-yl]-fluoren-9-one

The product of Example 13B (130 mg, 0.46 mmol) was treated with aqueous formaldehyde (5 mL, 37%; EM Science) and NaBH(OAc)$_3$ (163 mg, 0.77 mmol; Aldrich). After stirring for 3 h, the reaction was quenched with saturated NaHCO$_3$ (5 mL) and diluted with $CH_2Cl_2$ (5 mL). The layers were separated and the aqueous phase was extracted with $CH_2Cl_2$ (3×5 mL). The combined organics were dried over Na$_2$SO$_4$, filtered, and concentrated under reduced pressure and purified via column chromatography (silica gel, 1:9:90 NH$_4$OH/CH$_3$OH/CH$_2$Cl$_2$) to give the title compound (>100%, impure). MS (DCI/$NH_3$) m/z 305 (M+H)+.

Example 14B

2-[7-Methyl-3,7-diazabicyclo[3.3.0]octan-3-yl]-fluoren-9-one l-tartrate

To the product of Example 14A (0.46 mmol) in 10% $CH_3OH/EtOAc$ (2 mL) was added l-tartaric acid (83 mg, 0.55 mmol; Aldrich) in 10% $CH_3OH/EtOAc$ (1 mL). The resulting precipitate was isolated via filtration to afford the title compound (208 mg, 0.45 mmol, 98% yield). $^1$H NMR (methanol-$d_4$, 300 MHz): δ7.49 (1H, dt, J=7, 1 Hz), 7.43-7.47 (3H, m), 7.16 (1H, m), 7.03 (1H, d, J=2 Hz), 6.86 (1H, dd, J=9, 3 Hz), 4.37 (4H, s), 3.52 (2H, m), 3.60 (2H, m), 3.20-3.32 (6H, m), 2.36 (3H, s); MS (DCI/$NH_3$) m/z 305 (M+H)+; Anal. Calcd. for $C_{20}H_{20}N_2O \cdot C_4H_6O_6 \cdot 0.25H_2O$: C, 62.80; H, 5.82; N, 6.10; Found: C, 62.44; H, 5.75; N, 5.90.

Example 15

2,7-Bis(3-diethylamino-propyn-1-yl)-fluoren-9-one dihydrochloride

Example 15A 2,7-Bis(3-diethylamino-propyn-1-yl)-fluoren-9-one

A mixture of 2,7-dibromofluoren-9-one (1.00 g, 2.97 mmol; Aldrich), 3-diethylamino-1-propyne (1.6 mL, 11.6 mmol; Lancaster), triethylamine (2 mL, 14.4 mmol; Acros), dichlorobis(triphenylphosphino)palladium (II) ($Cl_2Pd(PPh_3)_2$; 90 mg, 0.13 mmol; Aldrich), and copper (I) iodide (130 mg, 0.68 mmol; Aldrich) in DMF (30 mL) was heated to 65° C. for 60 h. The reaction mixture was diluted with EtOAc, washed with water and brine, and dried over $Na_2SO_4$. The residue was purified twice by chromatography (80 g silica gel, eluting with 2-7% of 10% $NH_4OH$/MeOH in $CH_2Cl_2$, followed by 80 g silica gel, 1-6% MeOH—$CH_2Cl_2$) to afford the title compound (1.12 g, 2.81 mmol, 95% yield). MS ($DCI/NH_3$) m/z 399 $(M+H)^+$.

Example 15B 2,7-Bis(3-diethylamino-propyn-1-yl)-fluoren-9-one dihydrochloride The product from Example 15A (260 mg, 0.65 mmol) was converted to the title compound (280 mg, 0.58 mmol, 89%) according to the procedure described in Example 10B. $^1$H NMR (300 MHz, $D_2O$): δ 7.70 (2H, dd, J=8, 1 Hz), 7.66 (2H, s), 7.58 (2H, d, J=8 Hz), 4.35 (4H, s), 3.43 (8H, q, J=7 Hz), 1.41 (12H, t, J=7 Hz). MS ($DCI/NH_3$): m/z 399 $(M+1)^+$. Anal. Calcd. for $C_{27}H_{30}N_2O\cdot2HCl\cdot0.6H_2O$: C, 67.24; H, 6.94; N, 5.81. Found: C, 66.93; H, 7.24; N, 5.82.

Example 16

3,7-Bis(2-diethylaminoethoxy)dibenzothiophene dihydrochloride

Example 16A 3,7-Bis(2-diethylaminoethoxy)dibenzothiophene

To a 0° C. mixture of 3,7-bis(2-diethylaminoethoxy)dibenzothiophene-5,5-dioxide (5.30 g, 1.2 mmol; see *J. Med. Chem.*, 1978, 21, 1084) in dry THF (10 mL) was added portion-wise lithium aluminum hydride (90 mg, 2.4 mmol, Aldrich). The reaction mixture was allowed to warm to ambient temperature and then heated at reflux for 2 hours. After cooling to room temperature, the reaction mixture was quenched by sequential addition of $H_2O$-THF (1:9, 1 mL), aq. NaOH (2.5 N, 0.1 mL), and $H_2O$ (0.3 mL). The mixture was stirred for 30 minutes, filtered, and the residue was purified by flash chromatography (35 g silica gel, eluting with 4-8% of 10% $NH_4OH$/MeOH in $CH_2Cl_2$) to afford the title compound (250 mg, 51% yield).

Example 16B 3,7-Bis(2-diethylaminoethoxy)dibenzothiophene dihydrochloride

To a stirred solution of the product of Example 16A (250 mg, 0.60 mmol) in ethyl acetate (5 mL) and ethanol (0.2 mL), was added a solution of HCl in dioxane (4M; 0.33 mL, 1.32 mmol; Aldrich). After stirring the mixture for 6 hours, the resulting solid was collected by filtration to afford the title compound (284 mg, 0.50 mmol; 93%). $^1$H NMR (300 MHz, methanol-d4): δ 8.05 (2H, d, J=9 Hz), 7.54 (2H, d, J=2 Hz), 7.16 (2H, dd, J=9, 2 Hz), 4.46 (4H, t, J=5 Hz), 3.68 (4H, t, J=5 Hz), 3.44-3.35 (8H, q, J=7 Hz), 1.40 (12H, t, J=7 Hz). MS ($DCI/NH_3$): m/z 415 $(M+1)^+$. Anal. Calcd. for $C_{24}H_{34}N_2O_2S\cdot2HCl\cdot0.2C_4H_8O_2$: C, 58.97; H, 7.50; N, 5.55. Found: C, 58.94; H, 7.43; N, 5.52.

Example 17

3,7-Bis(2-diethylaminoethoxy)dibenzothiophene-5-oxide di-p-toluenesulfonate

Example 17A 3,7-Bis(2-diethylaminoethoxy)dibenzothiophene-5-oxide

To a cooled solution (0° C.) of the product of Example 16A (347 mg, 0.83 mmol) in dry THF (2 mL), was added a solution of $CF_3CO_3H$ in THF (4 M; 0.21 mL, 0.83 mmol). The reaction was stirred 30 minutes at 0° C., then for 30 minutes at room temperature, and concentrated under vacuum. The residue was purified by flash chromatography (35 g silica gel, 1:5:94 $NH_4OH$-MeOH—$CH_2Cl_2$) to afford the title compound (360 mg, 100%).

Example 17B 3,7-Bis(2-diethylaminoethoxy)dibenzothiophene-5-oxide di-p-toluenesulfonate The product of Example 17A (200 mg, 0.46 mmol) was converted to the title compound (218 mg, 0.28 mmol; 61%) according to the procedure of Example 1D. $^1$H NMR (300 MHz, methanol-d4): δ 7.89 (2H, d, J=8 Hz), 7.67 (6H, m), 7.33 (4H, dd, J=8, 2 Hz), 7.21 (4H, d, J=8 Hz), 4.45 (4H, t, J=5 Hz), 3.68 (4H, t, J=5 Hz), 3.43-3.32 (8H, m), 2.33 (6H, s), 1.39 (12H, t, J=5 Hz). MS ($DCI/NH_3$): m/z 431 $(M+1)^+$. Anal. Calcd. for $C_{24}H_{34}N_2O_3S\cdot2C_7H_8O_3S$: C, 58.66; H, 6.50; N, 3.61. Found: C, 58.66; H, 6.53; N, 3.49.

Example 18

3,7-Bis[(3S)-1-azabicyclo[2.2.2]octan-3-yloxy]-dibenzothiophene p-toluenesulfonate

Example 18A 3,7-Bis[(3S)-1-azabicyclo[2.2.2]octan-3-yloxy]-dibenzothiophene

To a 0° C. mixture of 3,7-dihydroxybenzothiophene-5,5-dioxide (300 mg, 1.2 mmol; see *J. Med. Chem.* 1978, 21, 1084), (3R)-quinuclidin-3-ol (770 mg, 6.0 mmol; Acros), and polymer-bound triphenylphosphine (2.0 g, 3 mmol/g; Aldrich) in THF (12 mL) was added di-tert-butylazodicarboxylate (1.2 mL, 6.0 mmol; Aldrich). The mixture was stirred overnight (16 h) at room temperature, filtered through diatomaceous earth, then rinsed with ethyl acetate. The residue was purified by flash chromatography (35 g silica gel, eluting with 5-10% of 10% $NH_4OH$/MeOH in $CH_2Cl_2$) to afford the title compound (150 mg, 27% yield).

Example 18B 3,7-Bis[(3S)-1-azabicyclo[2.2.2]octan-3-yloxy]-dibenzothiophene p-toluenesulfonate The product of Example 18A (150 mg, 0.32 mmol) was dissolved in ethyl acetate (5 mL) and ethanol (0.2 mL), then p-toluenesulfonic acid monohydrate (122 mg, 0.64 mmol; Aldrich) was added. After stirring the mixture for 16 hours, the resulting solid was collected by filtration to afford the title compound (245 mg, 0.30 mmol; 94%). $^1$H NMR (300 MHz, methanol-d4): δ 7.89 (2H, d, J=8 Hz), 7.70 (4H, d, J=8 Hz), 7.47 (2H, d, J=2 Hz), 7.34 (1H, d, J=2 Hz), 7.32 (2H, dd, J=8, 2 Hz), 7.22 (4H, d, J=8 Hz), 5.04 (2H, m), 3.87 (2H, m), 3.5-3.28 (12H, m), 2.55 (2H, m), 2.40-2.21 (7H, m), 2.21-1.83 (5H, m). MS (DCI/NH$_3$): m/z 467 (M+1)$^+$. Anal. Calcd. for C$_{25}$H$_{30}$N$_2$O$_3$.2C$_7$H$_8$O$_3$S.0.5H$_2$O: C, 58.59; H, 5.78; N, 3.42. Found: C, 58.58; H, 5.84; N, 3.39.

Example 19

2-[(1S,5S)-3,6-Diazabicyclo[3.2.0]heptan-3-yl]-dibenzothiophene-5,5-dioxide p-toluenesulfonate

Example 19A

Benzyl N-(2,2-dimethoxyethyl)carbamate

Benzyl chloroformate (231.3 g, 1.3 mol) was added gradually to a mixture of aminoacetaldehyde dimethyl acetal (152.0 g, 1.3 mol) in toluene (750 mL) and aqueous NaOH (72.8 g, 1.82 mol; in 375 mL of water) at 10-20° C. After the addition was complete, the mixture was stirred at ambient temperature for 4 h. The organic layer was separated, washed with brine (2×100 mL) and concentrated to provide the title compound. MS (DCI/NH$_3$): m/z 240 (M+1)$^+$, 257 (M+18)$^+$.

Example 19B

Benzyl N-allyl-N-(2,2-dimethoxyethyl)carbamate

The product of Example 19A (281.0 g, 1.18 mol) in dry toluene (1.0 L) was treated with powdered potassium hydroxide (291.2 g, 5.20 mol) and triethylbenzylammonium chloride (4.4 g, 0.02 mol). A solution of allyl bromide (188.7 g, 1.56 mol) in toluene (300 mL) was then added dropwise over 1 h at 20-30° C. The mixture was stirred overnight at room temperature and then water (300 mL) was added over 20 min at 20-30° C. The layers were separated and the aqueous phase was extracted with toluene (2×300 mL). The organic phases were combined, washed with brine (2×100 mL), dried (K$_2$CO$_3$), filtered and the filtrate concentrated to provide the title compound. MS (DCI/NH$_3$): m/z 280 (M+1)$^+$, 297 (M+18)$^+$.

Example 19C

Benzyl N-allyl-N-(2-oxoethyl)carbamate

The product of Example 19B (314.0 g, 1.125 mol) was treated with formic acid (88%, 350 mL) at room temperature and allowed to stir for 15 h. Most of the formic acid was removed by concentration under reduced pressure at 40-50° C. The residue was extracted with ethyl acetate (3×500 mL). The extracts were combined and washed with brine until the wash had a pH=6-7. The organic phase was concentrated to provide the title compound. MS (DCI/NH$_3$): m/z 234 (M+1)$^+$.

Example 19D

Benzyl N-allyl-N-[2-(hydroxyimino)ethyl]carbamate

The product of Example 19C (260 g, 1.115 mol) in acetonitrile (1.5 L) was treated with sodium acetate trihydrate (170.6 g, 4.41 mol) in distilled water (750 mL) and hydroxylamine hydrochloride (98.0 g, 4.41 mol) under nitrogen. The mixture was stirred at room temperature for about 20 h. The volatiles were removed under reduced pressure and the residue was extracted with ethyl acetate (2×750 mL). The combined organic phases were washed with brine until the wash had a pH=7. The organic phase was concentrated to provide the title compound. MS (DCI/NH$_3$): m/z 249 (M+1)$^+$, 266 (M+18)$^+$.

Example 19E

Benzyl cis-3-amino-4-(hydroxymethyl)-1-pyrrolidine carboxylate

A solution of the product of Example 19D (240 g, 0.97 mol) in xylenes (1.0 L) was heated at reflux under nitrogen for about 10 h. The resulting brown solution was cooled to 10-15° C. and acetic acid (1.0 L) was added under N$_2$. Zinc powder (100 g, 1.54 mol) was added gradually, and the gray mixture was stirred at room temperature for 3 h. The mixture was filtered and water (1.0 L) was added to the filtrate. The filtrate was stirred for 10 min and the organic layer was separated. The aqueous phase was washed with xylenes (4×400 mL) and then concentrated under reduced pressure to a volume of approximately 200 mL. The pH of the residue was adjusted with base to pH 9-10 by addition of saturated aqueous Na$_2$CO$_3$. The precipitated white solid was removed by filtration and the filtrate was extracted with chloroform (3×600 mL). The combined organic phases were washed with saturated Na$_2$CO$_3$ solution (2×50 mL) and dried over anhydrous Na$_2$CO$_3$. The mixture was filtered through a short column of diatomaceous earth and the filtrate was concentrated to provide the title compound. MS (DCI/NH$_3$): m/z 251 (M+1)$^+$.

Example 19F

Benzyl (4aS,7aS)-2,2-dimethylhexahydropyrrolo[3,4-d][1,3]oxazine-6(4H)-carboxylate (R)-mandelate The product of Example 19E (140 g, 0.56 mol) in dry acetone (150 mL) was treated with 2-methoxypropene (55 mL, 0.57 mol) at room temperature overnight. The reaction mixture was concentrated under reduced pressure and the residue was dissolved in dry acetone (750 mL). (R)-Mandelic acid (85 g, 0.56 mol) was added and the solution was stirred at room temperature for 48 h. The precipitate was isolated by filtration and dried under reduced pressure to provide the title compound as a solid. MS (DCI/NH$_3$): m/z 291 (M+1)$^+$.

Example 19G

Benzyl (3S,4S)-3-[(tert-butoxycarbonyl)amino]-4-(hydroxymethyl)-1-pyrrolidinecarboxylate The product of Example 19F (56 g, 127 mmol) in ethanol (50 mL) was treated with 5% aqueous sulfuric acid (100 mL)

at room temperature and allowed to stir for 16 h. The pH of the mixture was adjusted with base to pH ~10 with 20% aqueous sodium hydroxide (50 mL) and then the mixture was treated with di-tert-butyl dicarbonate (41.5 g, 190 mmol) in ethanol (50 mL) at 10-20° C. After stirring at room temperature for 4 h, the ethanol was removed under reduced pressure and the residue was extracted with ethyl acetate (3×500 mL). The combined organic phases were washed with brine (2×100 mL) and concentrated to provide the title compound. MS (DCI/NH$_3$): m/z 351 (M+1)$^+$, 368 (M+18)$^+$. The enantiomeric purity of the title compound was determined to be >99% ee by chiral HPLC (Chiracel AD column; ethanol/hexanes=20/80, 1.0 mL/minute, UV 220 nm; retention time 10.8 min).

Example 19H

Benzyl (3S,4S)-3-[(tert-butoxycarbonyl)amino]-4-{[(methylsulfonyl)oxy]methyl}-1-pyrrolidinecarboxylate The product of Example 19G (43.7 g, 125 mmol) and triethylamine (25.2 g, 250 mmol) in CH$_2$Cl$_2$ (600 mL) were treated with methanesulfonyl chloride (12.6 mL, 163 mmol) over 30 minutes at −10° C. The solution was allowed to warm to room temperature over 1 h and quenched with water (100 mL). The layers were separated and the aqueous phase was extracted with CH$_2$Cl$_2$ (2×400 mL). The combined organic phases were washed with brine (2×100 mL), dried over Na$_2$SO$_4$, filtered, and the filtrate concentrated to provide the title compound. MS (DCI/NH$_3$): m/z 429 (M+1)$^+$, 446 (M+18)$^+$.

Example 19I

Benzyl (3S,4S)-3-amino-4-{[(methylsulfonyl)oxy]methyl}-1-pyrrolidinecarboxylate trifluoroacetate The product of Example 19H (43.7 g, 125 mmol) in CH$_2$Cl$_2$ (150 mL) was treated with trifluoroacetic acid (50 mL) at room temperature and allowed to stir for 1 h. The mixture was concentrated under reduced pressure to give the title compound. MS (DCI/NH$_3$): m/z 329 (M+1)$^+$.

Example 19J

Benzyl (1S,5S)-3,6-diazabicyclo[3.2.0]heptane-3-carboxylate

The product of Example 19I was dissolved in ethanol (250 mL) and the pH was adjusted with base to pH ~12 with 25% aqueous NaOH. The mixture was warmed to 60° C. for 1.5 h, then allowed to cool to room temperature and used in the next step without further purification. An analytical sample was removed (~1 mL) and concentrated under reduced pressure. The residue was extracted with chloroform (2×5 mL). The extracts were combined, washed with brine (3×2 mL) and then passed through a short column of diatomaceous earth. The filtrate was concentrated to provide an analytical amount of the title compound. MS (DCI/NH$_3$): m/z 233 (M+H)$^+$, 250 (M+NH$_4$)$^+$.

Example 19K

6-Boc-3-carboxybenzyl-(1R,5S)-3,6-diazabicyclo[3.2.0]heptane

The solution of Example 19J was slowly added to di-tert-butyl dicarbonate (40.9 g, 188 mmol) in ethanol (50 mL) over 30 min at room temperature. The mixture was stirred at room temperature for additional 0.5-1 h, then concentrated under reduced pressure. The residue was extracted with ethyl acetate (3×500 mL). The ethyl acetate extracts were combined, washed with brine (3×50 mL), stirred with KHSO$_4$ (5%, 100 mL) for 10 min and the phases separated. The organic layer was washed with brine (3×50 mL) and passed through a short column of diatomaceous earth. The filtrate was concentrated to provide the title compound which was used in the next step without further purification. MS (DCI/NH$_3$): m/z 333 (M+1)$^+$.

Example 19L tert-Butyl (1R,5S)-3,6-diazabicyclo[3.2.0]heptane-6-carboxylate

The product of Example 19K (40.0 g, 0.120 mol) was dissolved in methanol (400 mL) and treated with Pd/C (10 wt %, 4.0 g) under hydrogen at room temperature for 10 h. The reaction mixture was filtered through a short column of diatomaceous earth and the filtrate was concentrated to provide the title compound. MS (DCI/NH$_3$): m/z 199 (M+1)$^+$.

Example 19M 2,8-Dibromo-dibenzothiophene 5,5-dioxide

To a solution of 2,8-dibromodibenzothiophene (2.50 g, 7.4 mmol; TCI-US) in acetic acid (20 mL; EM Science) was added 30% hydrogen peroxide (10 mL; JT Baker). The solution was heated at reflux overnight (16 h), then cooled to room temperature, 25 mL of water added and the resulting solid was collected by filtration, washed with excess water to afford the title compound (1.65 g, 4.4 mmol, 60% yield). MS (DCI/NH$_3$): m/z 392 (M+18)$^+$.

Example 19N

2-Bromo-8-[6-Boc-(1R,5S)-3,6-diazabicyclo[3.2.0]heptanyl]-dibenzothiophene-5,5-dioxide A catalyst solution was prepared by mixing tris(dibenzylideneacetone)dipalladium (Pd$_2$(dba)$_3$; 40 mg, 0.043 mmol; Alfa) and racemic 2,2'-bis(diphenylphosphino)-1,1'-binaphthyl (BINAP; 54 mg, 0.086 mmol; Strem) in toluene (10 mL) and heating the mixture to 80° C. for 15 min. The solution was cooled and then was added the products of Example 19M (800 mg, 2.15 mmol) and Example 19L (640 mg, 3.2 mmol;) in toluene (5 mL). Cesium carbonate (1.05 g, 3.2 mmol; Aldrich) was then added, and the reaction mixture was purged with nitrogen and heated to 80-85° C. for 16 h. After cooling to room temperature, the mixture was filtered through diatomaceous earth and purified by chromatography (80 g silica gel, 50:48:2 ethyl acetate-hexane diethylamine) to afford the title compound (100 mg, 0.20 mmol, 10% yield): MS (DCI/NH$_3$): m/z 492 (M+1)$^+$.

Example 19O

2-[6-Boc-(1R,5S)-3,6-diazabicyclo[3.2.0]heptan-3-yl]-dibenzothiophene-5,5-dioxide A solution of the product from Example 19N (100 mg) in ethanol was treated with 10% palladium on carbon (50 mg) under 1 atm hydrogen (balloon) for 16 hours. The catalyst was filtered off and the resulting solution was concentrated to afford the title compound (55 mg, 0.13 mmol). MS (DCI/NH$_3$): m/z 413 (M+1)$^+$.

Example 19P

2-[(1S,5S)-3,6-diazabicyclo[3.2.0]heptan-3-yl]-dibenzothiophene-5,5-dioxide A solution of the product of Example 19O (55 mg, 0.13 mmol) in dichloromethane (5 mL) was cooled to 0° C. and treated with trifluoroacetic acid (3 mL). After stirring for 30 min, the reaction mixture was warmed to room temperature and the stirring continued for an additional 30 min. The solution was diluted with dichloromethane, washed with 1 N NaOH (aq), concentrated, and purified by flash chromatography (20 g silica gel, 1:10:89 NH$_4$OH:MeOH:CH$_2$Cl$_2$) to afford the title compound (37 mg, 0.12 mmol, 89% yield). MS (DCI/NH$_3$): m/z 313 (M+H)$^+$.

Example 19Q

2-[(1S,5S)-3,6-diazabicyclo[3.2.0]heptan-3-yl]-dibenzothiophene-5,5-dioxide p-toluenesulfonate The product of Example 19P (37 mg, 0.12 mmol) was dissolved in ethyl acetate (5 mL) and ethanol (0.2 mL), then p-toluenesulfonic acid monohydrate (27 mg, 0.14 mmol; Aldrich) was added. After stirring the mixture for 16 hours, the resulting solid was collected by filtration to afford the title compound (36.4 mg, 0.09 mmol; 64%): $^1$H NMR (300 MHz, methanol-d4) δ 8.04 (1H, d, J=8 Hz), 7.78-7.58 (6H, m), 7.43 (1H, d, J=2 Hz), 7.20 (2H, d, J=8 Hz), 7.04 (1H, dd, J=8, 2 Hz), 5.10 (1H, t, J=2 Hz), 4.30 (2H, m) 4.08 (1H, d, J=8 Hz), 3.75 (1H, m), 3.59 (1H, m) 3.35-3.19 (2H, m), 2.34 (3H, s). MS (DCI/NH$_3$): m/z 313 (M+1)$^+$. Anal. Calcd. for C$_{17}$H$_{16}$N$_2$O$_2$S.C$_7$H$_8$O$_3$S: C, 59.48; H, 4.99; N, 5.78. Found: C, 59.19; H, 4.78; N, 5.65.

Example 20

2-Amino-7-[3,7-diazabicyclo[3.3.0]octan-3-yl]-fluoren-9-one dihydrochloride

Example 20A

2-[N-Boc-3,7-diazabicyclo[3.3.0]octan-3-yl]-7-bromofluoren-9-one

A mixture of 3-Boc-3,7-diazabicyclo[3.3.0]octane (2.12 g, 10.0 mmol; see WO 0181347), 2,7-dibromofluoren-9-one (6.76 g, 20.0 mmol; Aldrich), tris(dibenzylideneacetone)dipalladium (0) (Pd$_2$ dba$_3$; 185 mg, 0.202 mmol; Strem), racemic-2,2'-bis(diphenylphosphino)-1,1'-binaphthyl (BINAP; 310 mg, 0.498 mmol; Strem) and sodium tert-butoxide (1.4 g, 14.6 mmol; Aldrich) in 100 mL toluene was warmed to 85° C. and stirred for 9 h. The reaction mixture was cooled to ambient temperature and filtered through diatomaceous earth, rinsing with dichloromethane. After concentrating the solution under reduced pressure, the residue was purified by column chromatography (silica gel, 10-60% EtOAc/hexanes) to give the title compound (3.54 g, 7.55 mmol, 75% yield). MS (DCI/NH$_3$): m/z 469, 471 (M+1)$^+$.

Example 20B

2-[N-Boc-3,7-diazabicyclo[3.3.0]octan-3-yl]-7-(diphenylmethyleneamino)-fluoren-9-one The product of Example 20A (494 mg, 1.05 mmol), benzophenone imine (220 μL, 1.31 mmol; Aldrich), tris(dibenzylideneacetone)dipalladium (0) (Pd$_2$ dba$_3$; 19 mg, 0.021 mmol; Strem), racemic-2,2'-bis(diphenylphosphino)-1,1'-binaphthyl (BINAP; 39 mg, 0.063 mmol; Strem) and sodium tert-butoxide (140 mg, 1.46 mmol; Aldrich) in 5 mL toluene were warmed to 80° C. and stirred for 18 h. The reaction mixture was cooled to ambient temperature and filtered through diatomaceous earth, rinsing with dichloromethane. After concentrating the solution under reduced pressure, the residue was purified by column chromatography (silica gel, 10-60% EtOAc/hexanes) to give the title compound (572 mg, 0.958 mmol, 96% yield). MS (DCI/NH$_3$): m/z 570 (M+1)$^+$.

Example 20C

2-Amino-7-[N-Boc-3,7-diazabicyclo[3.3.0]octan-3-yl]-fluoren-9-one

To a solution of the product of Example 20B (572 mg, 0.958 mmol) in THF (5 mL) was added 5 drops aqueous 2 N HCl. The reaction mixture was stirred for 4 h, then diluted with dichloromethane, washed with aqueous 1 N NaOH, and concentrated under reduced pressure. The residue was purified by column chromatography (silica gel, 10-100% EtOAc/hexanes) to afford the title compound (353 mg, 0.872 mmol, 91% yield). MS (DCI/NH$_3$): m/z 406 (M+1)$^+$.

Example 20D

2-Amino-7-[3,7-diazabicyclo[3.3.0]octan-3-yl]-fluoren-9-one dihydrochloride A solution of the product of Example 20C (126 mg, 0.311 mmol) in dichloromethane (2 mL) was cooled to 0° C. and treated with trifluoroacetic acid (2 mL). After stirring for 30 min, the reaction mixture was warmed to room temperature and the stirring continued for an additional 1 h. The solution was diluted with dichloromethane, washed with dilute Na$_2$CO$_3$ (aq), and concentrated to afford the free base of the title compound (97 mg, 0.32 mmol, 100% yield). This material was dissolved in ethanol containing a few drops of methanol and treated with a solution of HCl in dioxane (4 M, 150 μL, 0.60 mmol; Aldrich). After stirring for 1 h, the solution was concentrated and the residue triturated with EtOH-EtOAc to afford the title compound: $^1$H NMR (300 MHz, methanol-d4) δ 7.62 (1H, dd, J=7, 1 Hz), 7.55 (1H, d, J=8 Hz), 7.46 (2H, m), 7.04 (1H, d, J=2 Hz), 6.88 (1H, dd, J=8, 2 Hz), 3.68-3.43 (6H, m), 3.30-3.21 (4H, m). MS (DCI/NH$_3$): m/z 306 (M+1)$^+$. Anal. Calcd. for C$_{19}$H$_{19}$N$_3$O.1.9HCl.0.1C$_4$H$_8$O$_2$: C, 60.77; H, 5.70; N, 10.96. Found: C, 61.09; H, 5.41; N, 10.66.

Example 21

2-[(3R)-1-Azabicyclo[2.2.2]octan-3-yloxy]-xanthen-9-one trifluoroacetate

Example 21A

(3R)-1-azabicyclo[2.2.2]octan-3-ol (R)-3-Quinuclidinol hydrochloride (20 g, 12.2 mmol; Aldrich) was treated with aq. NaOH (20%, 50 mL) at ambient temperature for 10 min, then extracted with $CHCl_3$/iPrOH (10:1, 3×200 mL). The extracts were combined, washed with brine (50 mL) and dried over $MgSO_4$. After removal of the drying agents by filtration, the filtrate was concentrated under reduced pressure to afford the title compound as white solid (15.5 g, 122 mmol, 99% yield). $^1$H NMR (300 MHz, methanol-d4) δ 3.88-3.82 (1H, m), 3.10 (1H, ddd, J=14, 8, 2 Hz), 2.95-2.50 (5H, m), 2.05-1.90 (1H, m), 1.85-1.76 (2H, m), 1.60-1.52 (1H, m), 1.50-1.36 (1H, m). MS (DCI/$NH_3$): m/z 128 (M+1)$^+$.

Example 21B

2-[(3R)-1-Azabicyclo[2.2.2]octan-3-yloxy]-xanthen-9-one

The product from Example 21A (256 mg, 2.02 mmol) was combined with 2-iodoxanthen-9-one (322 mg, 1.00 mmol; see *J. Chem. Research (S)*, 1999, 590), copper (I) iodide (20 mg, 0.11 mmol; Aldrich), 1,10-phenanthroline (36 mg, 0.20 mmol; Aldrich) and powdered cesium carbonate (500 mg, 1.53 mmol; Aldrich) in dry toluene (1 mL) was heated to 110° C. and stirred under nitrogen for 36 hours. After cooling to room temperature, the reaction mixture was filtered through diatomaceous earth, rinsing with dichloromethane, concentrated and purified by flash chromatography (80 g silica gel, 1:10:89 $NH_4OH$:MeOH:$CH_2Cl_2$). The resulting material (250 mg) was repurified by reverse-phase HPLC (40×100 mm Symmetry-$C_8$, 5-30% aq. TFA (0.1%)-MeCN) to afford the title compound (57 mg, 0.18 mmol, 18% yield). MS (DCI/$NH_3$): m/z 322 (M+1)$^+$.

Example 21C

2-[(3R)-1-Azabicyclo[2.2.2]octan-3-yloxy]-xanthen-9-one trifluoroacetate

The product from Example 21B (57 mg, 0.18 mmol) was dissolved in methanol (500 μL) and treated with trifluoroacetic acid (2 drops). The mixture was diluted with ether (5 mL) and stirred at room temperature for 1 h. The resulting precipitate was collected by centrifugation and washed with ether, affording the title compound (44 mg, 0.10 mmol, 56% yield): $^1$H NMR (300 MHz, methanol-d4) δ 8.29 (1H, dd, J=8, 2 Hz), 7.85 (1H, ddd, J=8, 7, 2 Hz), 7.72 (1H, d, J=7 Hz), 7.65 (1H, d, J=9 Hz), 7.62 (1H, d, J=8 Hz), 7.54 (1H, dd, J=9, 3 Hz), 7.47 (1H, ddd, J=8, 7, 1 Hz), 5.03 (1H, m), 3.89 (1H, ddd, J=8, 7, 2 Hz), 3.48-3.25 (5H, m), 2.59 (1H, m), 2.34 (1H, m), 2.21-2.00 (2H, m), 1.91 (1H, m). MS (DCI/$NH_3$): m/z 322 (M+1)$^+$. Anal. Calcd. for $C_{20}H_{19}NO_3 \cdot C_2HF_3O_2$: C, 60.69; H, 4.63; N, 3.22. Found: C, 60.36; H, 4.28; N, 3.10.

Example 22

2-(1-Azabicyclo[2.2.2]octan-3-yloxy)-9H-carbazole

To a 0° C. mixture of 2-hydroxy-9H-carbazole (369 mg, 2.02 mmol; Aldrich), quinuclidin-3-ol (260 mg, 2.05 mmol; Aldrich), and triphenylphosphine (646 mg, 2.47 mmol; Aldrich) in THF (10 mL) was added diethylazodicarboxylate (320 μL, 2.03 mmol; Lancaster). After 1 h, the reaction mixture was allowed to warm to room temperature and was stirred for 3 d. The mixture was diluted with dichloromethane, washed with saturated aq. $NaHCO_3$, dried over $MgSO_4$, and purified by flash chromatography (80 g silica gel, eluting with 1-16% of 10% $NH_4OH$/MeOH in $CH_2Cl_2$) to afford the title compound as an oil (350 mg, 1.20 mmol, 59% yield). Trituration of the oil with ethyl acetate produced a solid. $^1$H NMR (300 MHz, methanol-d4) δ 7.92 (1H, d, J=6 Hz), 7.90 (1H, d, J=8 Hz), 7.37 (1H, d, J=8 Hz), 7.26 (1H, ddd, J=7, 7, 1 Hz), 7.10 (1H, ddd, J=8, 8, 1 Hz), 6.92 (1H, d, J=2 Hz), 6.78 (1H, dd, J=8, 2 Hz), 4.59 (1H, m), 3.36 (1H, ddd, J=14, 8, 2 Hz), 3.04-2.75 (5H, m), 2.22 (1H, m), 2.11 (1H, m), 1.88-1.65 (2H, m), 1.51 (1H, m). MS (DCI/$NH_3$): m/z 293 (M+1)$^+$. Anal. Calcd. for $C_{19}H_{20}N_2O \cdot 0.1 C_4H_8O_2$: C, 77.36; H, 6.96; N, 9.30. Found: C, 77.04; H, 7.23; N, 9.45.

Example 23

2,7-Bis-(piperidin-4-yloxy)-fluoren-9-one bis(trifluoroacetate)

Example 23A 2,7-Bis-[1-Boc-piperidin-4-yloxy]-fluoren-9-one

A mixture of 2,7-diiodofluoren-9-one (1.2 g, 2.78 mmol; see J. Chem. Res. (S) 1999, 590), 1-Boc-4-hydroxypiperidine (2.2 g, 11.1 mmol; Aldrich), copper (I) iodide (53 mg, 0.28 mmol; Aldrich), 1,10-phenanthroline (100 mg, 0.56 mol; Aldrich) and powdered cesium carbonate (3.6 g, 11.0 mmol; Aldrich) in toluene (4 mL) was heated to 110° C. with vigorous stirring for 30 h. After cooling to room temperature, the reaction mixture was filtered through diatomaceous earth, rinsing with ethyl acetate and dichloromethane, and the residue purified by flash chromatography (80 g silica gel, 10-80% gradient of ethyl acetate in hexanes) to afford to afford the title compound (910 mg, 1.57 mmol; 56% yield): MS (CI/$NH_3$): m/z 579 (M+1)$^+$, 596 (M+18)$^+$.

A mixture of 2-[1-Boc-piperidin-4-yloxy]-fluoren-9-one and 2-[1-Boc-piperidin-4-yloxy]-7-iodofluoren-9-one (361 mg, approximately 1:1) was also collected as a byproduct and used without further purification: MS (DCI/$NH_3$): m/z 380 (M+1)$^+$, 397 (M+18)$^+$, 506 (M+1)$^+$, 523 (M+18)$^+$.

Example 23B 2,7-Bis-(piperidin-4-yloxy)-fluoren-9-one bis(trifluoroacetate)

The product of Example 23A (910 mg, 1.57 mmol) in $CH_2Cl_2$ (20 mL), was cooled to 0° C. and treated with trifluoroacetic acid (5 mL; EM Science). After 15 min the ice bath was removed and the reaction mixture stirred at room temperature overnight. Volatiles were removed under reduced pressure. The resulting dark orange oil was triturated with diethyl ether and dried to afford the title compound (930 mg, 1.52 mmol; 97% yield) $^1$H NMR (300 MHz, $CD_3OD$) δ ppm 1.97-2.11 (m, 4H), 2.12-2.25 (m, 4H), 3.17-3.29 (m, 4H), 3.35-3.47 (m, 4H), 4.71-4.80 (m, 2H), 7.13 (dd, J=8, 2 Hz, 2H), 7.22 (d, J=2 Hz, 2H), 7.49 (d, J=8 Hz, 2H); MS (DCI/$NH_3$) m/z 379 (M+H)$^+$; Anal. $C_{23}H_{26}N_2O_3 \cdot 2C_2HF_3O_2 \cdot 0.5 C_4H_8O_2$: C, H, N.

Example 24

2,7-Bis-(1-methyl-piperidin-4-yloxy)-fluoren-9-one dihydrochloride

Example 24A 2,7-Bis-(1-methyl-piperidin-4-yloxy)-fluoren-9-one and 2-(1-methylpiperidin-4-yloxy)-7-(piperidin-4-yloxy)-fluoren-9-one A mixture of the product of Example 23B (670 mg, 1.10 mmol), aq. formaldehyde (10 mL, 36% aq.; EM Science) and sodium triacetoxyborohydride (350 mg, 1.65 mmol; Aldrich) in water (5 mL) was stirred at room temperature for 16 h. The mixture was concentrated under vacuum and purified by flash chromatography (80 g silica gel, 1:10:89 NH$_4$OH-MeOH—CH$_2$Cl$_2$) to afford a mixture of the two title compounds:

2,7-Bis-(1-methylpiperidin-4-yloxy)-fluoren-9-one (110 mg, 0.27 mmol); MS (DCI/NH$_3$): m/z 407 (M+1)$^+$.

2-(1-Methylpiperidin-4-yloxy)-7-(piperidin-4-yloxy)-fluoren-9-one (81 mg, 0.21 mmol): MS (DCI/NH$_3$): m/z 393 (M+1)$^+$.

Example 24B 2,7-Bis-(1-methylpiperidin-4-yloxy)-fluoren-9-one dihydrochloride

To a solution of 2,7-bis-(1-methylpiperidin-4-yloxy)-fluoren-9-one (110 mg, 0.27 mmol; Example 24A) in ethyl acetate (10 mL) containing a few drops of ethanol was added a solution of HCl in dioxane (4 M, 335 μL, 1.34 mmol; Aldrich). After stirring the mixture for 2 h, the solid was collected by filtration and recrystallized from hot EtOH-EtOAc to afford the title compound (74 mg, 0.155 mmol, 57% yield): $^1$H NMR (300 MHz, CD$_3$OD) δ ppm 1.93-2.36 (m, 8H), 2.92 (s, 6H), 3.10-3.29 (m, 4H), 3.32-3.51 (m, 4H), 4.57-4.78 (m, 2H), 7.10-7.29 (m, 4H), 7.50 (d, J=8 Hz, 2H); MS (DCI/NH$_3$) m/z 407 (M+H)$^+$; Anal. C$_{25}$H$_{30}$N$_2$O$_3$.2HCl 0.1H$_2$O: C, H, N.

Example 25

2,7-Bis-(8-methyl-8-aza-bicyclo[3.2.1]oct-3-yloxy)-fluoren-9-one di-p-toluenesulfonate Example 25A Methanesulfonic acid 8-methyl-8-aza-bicyclo[3.2.1]oct-3-yl ester A mixture of 8-methyl-8-aza-bicyclo[3.2.1]oct-3-ol (1.12 g, 8.0 mmol; Aldrich) and triethylamine (3.5 g, 34.6 mmol; Spectrum) in dry THF (20 mL) was cooled to 0° C. with stirring, and methanesulfonyl chloride (0.75 mL, 9.7 mmol; Aldrich) was added slowly. The reaction mixture was allowed to warm to room temperature and stirred for 1 h. After filtering to remove the solid byproduct, the THF phase was concentrated, and the residue was dissolved in CH$_2$Cl$_2$ (40 mL), washed with water (20 mL), and concentrated to afford the title compound (0.8 g. 3.6 mmol; 45% yield): $^1$H NMR (300 MHz, CD$_3$OD) δ ppm 4.85-4.91 (1H, m), 3.14-3.20 (2H, m), 3.05 (3H, s), 2.29 (3H, s), 2.19-2.25 (1H, m), 2.14-2.19 (1H, m), 1.93-2.12 (6H, m); MS (DCI/NH$_3$): m/z 220 (M+H)$^+$.

Example 25B 2,7-Bis-(8-methyl-8-aza-bicyclo[3.2.1]oct-3-yloxy)-fluoren-9-one

A mixture of the product of Example 25A (800 mg, 3.6 mmol), 2,7-dihydroxy-fluoren-9-one (200 mg, 0.95 mmol) and powdered potassium hydroxide (120 mg, 2.1 mmol; Fisher) in DMF (10 mL) was heated to 80° C. with stirring for 16 h. After cooling to room temperature, the reaction mixture was concentrated, and the residue was dissolved in CH$_2$Cl$_2$ (10 mL) and washed with water and brine. The organic phase was concentrated and purified by flash chromatography (80 g silica gel, 0-30% gradient of MeOH in CH$_2$Cl$_2$) to afford the title compound (75 mg, 0.16 mmol; 17% yield): $^1$H NMR (300 MHz, CD$_3$OD) δ ppm 7.41 (2H, dd, J=8, 6 Hz), 7.08 (2H, dd, J=18, 2 Hz), 6.99 (2H, ddd, J=15, 8, 2 Hz), 4.55-4.70 (2H, m), 3.15-3.30 (4H, m), 2.33 (6H, d, J=4 Hz), 1.72-2.24 (16H, m); MS (DCI/NH$_3$): 459 (M+1)$^+$.

Example 25C 2,7-Bis-(8-methyl-8-azabicyclo[3.2.1]oct-3-yloxy)-fluoren-9-one di-p-toluenesulfonate To a solution of the product of Example 25B (75 mg, 0.16 mmol) in EtOAc (10 mL) was added p-toluenesulfonic acid monohydrate (61 mg, 0.32 mmol; Aldrich). The mixture was stirred for 16 h, and the resulting solid was collected by centrifugation to afford the title compound (76 mg, 0.09 mmol; 56% yield): $^1$H NMR (300 MHz, CD$_3$OD) δ ppm 7.70 (4H, d, J=8 Hz), 7.49 (2H, t, J=8.1 Hz), 7.23 (4H, d, J=8 Hz), 7.18 (2H, dd, J=15, 2 Hz), 7.09 (2H, ddd, J=13, 8, 2 Hz), 4.71-4.80 (2H, m), 3.96-4.03 (2H, m), 3.92 (2H, dd, J=4, 2 Hz), 2.82 (6H, s), 1.92-2.54 (22H, m); MS (DCI/NH$_3$): m/z 459 (M+1)$^+$. Anal. Calcd. for C$_{29}$H$_{34}$N$_2$O$_3$2.3C$_7$H$_8$O$_3$S: C, 63.38; H, 6.18; N, 3.28. Found: C, 63.21; H, 6.01; N, 3.23.

Example 26

2,7-Bis-[(S)-1-methylpyrrolidin-2-ylmethoxy]-fluoren-9-one difumarate

Example 26A 2,7-Bis-[(S)-1-methylpyrrolidin-2-ylmethoxy]-fluoren-9-one

To a solution of 2,7-dihydroxyfluorenone (150 mg, 0.708 mmol; see *Synth. Commun.* 1976, 6, 371) and (S)-2-hydroxymethyl-1-methylpyrrolidine (420 μL, 3.54 mmol; Aldrich) in THF (5 mL) was added polymer-bound triphenylphosphine (1.2 g, 3 mmol/g; Aldrich) followed by di-tert-butylazodicarboxylate (800 mg, 3.48 mmol; Aldrich). The mixture was stirred overnight (16 h) at room temperature, then filtered through diatomaceous earth, rinsing with CH$_2$Cl$_2$. After concentrating the solution, the residue was stirred with 4 M HCl in dioxane (5 mL; Aldrich) for 1 h. The reaction mixture then was adjusted to pH>10 with 1 N NaOH, extracted twice with CH$_2$Cl$_2$ and dried over K$_2$CO$_3$. Purification by flash chromatography (35 g silica gel, 2-10% gradient of NH$_4$OH-MeOH (1:10) in CH$_2$Cl$_2$) followed by reverse-phase HPLC (Waters Symmetry C$_8$ 40×100 mm column, gradient 5-95% MeCN-0.1% aq. TFA) afforded the title compound (134 mg, 0.329 mmol; 47% yield): MS (DCI/NH$_3$) m/z 407 (M+H)$^+$.

Example 26B 2,7-Bis-[(S)-1-methylpyrrolidin-2-ylmethoxy]-fluoren-9-one difumarate To a solution of the product of Example 26A (134 mg, 0.329 mmol) in ethanol (10 mL) was added a solution of fumaric acid (78 mg, 0.67 mmol; Aldrich) in ethanol (3 mL). After stirring for 16 h, the resulting orange solid was collected by filtration, affording the title compound (113 mg, 0.177 mmol; 54% yield): $^1$H NMR (300 MHz, CD$_3$OD) δ ppm 7.46-7.58 (m, 2H), 7.24 (d, J=2 Hz, 2H), 7.12-7.19 (m, 2H), 6.68 (s, 4H), 4.42 (dd, 2H), 4.27 (dd, 2H), 3.73-3.84 (m, 2H), 3.58-3.71 (m, 2H), 3.12-3.25 (m, 2H), 3.01 (s, 6H), 1.74-2.45

(m, 6H); MS (DCI/NH$_3$) m/z 407 (M+H)$^+$; Anal. C$_{25}$H$_{30}$N$_2$O$_3$.2C$_4$H$_4$O$_4$.0.3H$_2$O: C, H, N.

Example 27

2,7-Bis-(4-methylpiperazin-1-yl)-fluoren-9-one di-p-toluenesulfonate

Example 27A 2,7-Bis-(4-methylpiperazin-1-yl)-fluoren-9-one and 2-bromo-7-(4-methylpipiperazin-1-yl)-fluoren-9-one A mixture of 2,7-dibromofluoren-9-one (333 mg, 0.985 mmol; Aldrich), N-methylpiperazine (520 µL, 4.69 mmol; Aldrich), tris(dibenzylideneacetone)dipalladium (Pd$_2$(dba)$_3$; 14 mg, 0.015 mmol; Alfa), racemic 2,2'-bis(diphenylphosphino)-1,1'-binaphthyl (BINAP; 19 mg, 0.030 mmol; Strem), and sodium tert-butoxide (130 mg, 1.35 mmol; Aldrich) was heated neat at 85° C. for 16 h. The reaction mixture was cooled and purified by flash chromatography (80 g silica gel, 1-20% gradient of MeOH in CH$_2$Cl$_2$) to afford the two title compounds:

2,7-Bis-(4-methylpiperazin-1-yl)-fluoren-9-one: (purple oil, 127 mg, 0.338 mmol; 34% yield): $^1$H NMR (300 MHz, CDCl$_3$) δ 7.24 (d, J=8 Hz, 2H), 7.20 (d, J=2 Hz, 2H), 6.91 (dd, J=8, 3 Hz, 2H), 3.20-3.30 (m, 8H), 2.52-2.65 (m, 8H), 2.37 (s, 6H); MS (DCI/NH$_3$) m/z 377 (M+H)$^+$.

2-Bromo-7-(4-methylpiperazin-1-yl)-fluoren-9-one: (red oil, 118 mg, 0.0334 mmol; 34% yield): MS (DCI/NH$_3$) m/z 357, 359 (M+H)$^+$.

Example 27B 2,7-Bis-(4-methylpiperazin-1-yl)-fluoren-9-one di-p-toluenesulfonate To a solution of 2,7-bis-(4-methylpiperazin-1-yl)-fluoren-9-one from Example 27A (120 mg, 0.319 mmol) in EtOH-EtOAc (2 mL) was added a solution of p-toluenesulfonic acid monohydrate (60 mg, 0.32 mmol; Aldrich) in EtOH (2 mL). The mixture was stirred overnight and the purple precipitate was collected by filtration to afford the title compound (102 mg, 0.14 mmol; 89% yield based on p-toluenesulfonic acid monohydrate): $^1$H NMR (300 MHz, CD$_3$OD) δ ppm 7.70 (d, J=8 Hz, 4H), 7.45 (d, J=8 Hz, 2H), 7.19-7.27 (m, 6H), 7.13 (dd, J=8, 2 Hz, 2H), 2.96 (s, 6H), 2.35 (s, 6H); MS (DCI/NH$_3$) m/z 377 (M+H)$^+$; Anal. C$_{23}$H$_{28}$N$_4$O.2C$_7$H$_8$O$_3$S.0.1H$_2$O: C, H, N.

Example 28

2,7-Bis-[(1S,5S)-3,6-diazabicyclo[3.2.0]hept-3-yl]-fluoren-9-one di-p-toluenesulfonate

Example 28A 2,7-Bis-[(1S,5S)—N-Boc-3,6-diazabicyclo[3.2.0]hept-3-yl]-fluoren-9-one The product of Example 19L (800 mg, 4.0 mmol) was coupled with 2,7-dibromo-fluoren-9-one (1.014 g, 3.0 mmol; Aldrich) under the catalysis of Pd$_2$(dba)$_3$ (40 mg, 0.044 mmol; Aldrich) and BINAP (80 mg, 0.128 mmol; Strem) with t-BuONa (400 mg, 4.0 mmol; Aldrich) according to the procedure of Example 10A. Purification by flash chromatography (silica gel, 80:20 CH$_2$Cl$_2$-EtOAc, R$_f$=0.50) afforded the title compound as a solid (1.09 g, 1.91 mmol; 63% yield): $^1$H NMR (300 MHz, CD$_3$OD) δ ppm 1.45 (18H. s), 2.76-3.30 (6H, m), 3.65 (2H, dd, J=8, 4 Hz), 3.68-3.75 (2H, m), 3.89-4.18 (4H, m), 4.59-4.95 (2H, m), 6.74 (2H, br s), 7.03 (2H, br s), 7.19 (2H, br s); MS (DCI/NH$_3$) m/z 573 (M+H)$^+$.

Example 28B 2,7-Bis-[(1S,5S)-3,6-diazabicyclo[3.2.0]hept-3-yl]-fluoren-9-one di-p-toluenesulfonate The product of Example 28A (500 mg, 0.87 mmol) was treated with TsOH.H$_2$O (400 mg, 2.10 mmol; Aldrich) in EtOAc (20 mL) at 80° C. for 2 h to afford the title compound as solid (630 mg, 0.87 mmol; 99% yield): $^1$H NMR (300 MHz, DMSO-D$_6$) δ ppm 2.28 (6H, s), 2.94 (2H, dd, J=11, 6 Hz), 3.05 (2H, dd, J=12, 5 Hz), 3.29-3.47 (2H, m), 3.55-3.65 (2H, m), 3.90 (2H, d, J=10 Hz), 3.98-4.22 (4H, m), 4.80-5.03 (2H, m) 6.95 (2H, dd, J=8, 2 Hz), 7.03 (2H, d, J=2 Hz), 7.11 (4H, d, J=8 Hz), 7.48 (4H, d, J=8 Hz), 8.67 (2H, br s), 8.83 (2H, br s); MS (DCI/NH$_3$): m/z 373 (M+H)$^+$. Anal. Calculated for C$_{23}$H$_{24}$N$_4$O.2.00C$_7$H$_8$SO$_3$.0.75H$_2$O: C, 60.85; H, 5.73; N, 7.67. Found: C, 61.20; H, 5.53; N, 7.25.

Example 29

2,7-Bis-[(1S,5S)-6-methyl-3,6-diazabicyclo[3.2.0]hept-3-yl]-fluoren-9-one di-p-toluenesulfonate

Example 29A 2,7-Bis-[(1S,5S)-6-methyl-3,6-diazabicyclo[3.2.0]hept-3-yl]-fluoren-9-one The product of Example 28B (300 mg, 0.42 mmol) was treated with aqueous formaldehyde (30%, 3 mL, 30 mmol; Aldrich) and NaBH(OAc)$_3$ (440 mg, 2.0 mmol; Aldrich) in MeCN (10 mL) at ambient temperature overnight. The reaction was quenched with saturated aqueous Na$_2$CO$_3$ (5 mL), extracted with CHCl$_3$ (2×50 mL) and the residue purified by flash chromatography (silica gel, CH$_2$Cl$_2$-MeOH—NH$_4$OH, 90:10:2, R$_f$, 0.10) to afford the title compound as solid (160 mg, 0.40 mmol; 95% yield): $^1$H NMR (300 MHz, CD$_3$OD) δ ppm 2.45 (6H, s), 2.97 (2H, dd, J=11, 4 Hz), 3.08-3.20 (2H, m), 3.20-3.27 (2H, m), 3.34-3.41 (2H, m), 3.46 (2H, t, J=8 Hz), 3.67-3.88 (4H, m), 4.11 (2H, dd, J=6, 5 Hz), 6.81 (2H, dd, J=8, 2 Hz), 6.98 (2H, d, J=2 Hz), 7.27 (2H, d, J=8 Hz); MS (DCI/NH$_3$) m/z 401 (M+H)$^+$.

Example 29B 2,7-Bis-[(1S,5S)-6-methyl-3,6-diazabicyclo[3.2.0]hept-3-yl]-fluoren-9-one di-p-toluenesulfonate The product of Example 29A (160 mg, 0.40 mmol) was treated with TsOH.H$_2$O (190 mg, 1.00 mmol; Aldrich) in i-PrOH (10 mL) at 70° C. for 1 h and cooled to ambient temperature to afford the title compound as solid (120 mg, 0.15 mmol; 37% yield): $^1$H NMR (300 MHz, CD$_3$OD) δ ppm 2.38 (6H, s), 2.97 (6H, s), 3.05 (2H, dd, J=11, 6 Hz), 3.15 (2H, dd, J=13, 5 Hz), 3.49-3.61 (2H, m), 3.88 (2H, d, J=11 Hz), 3.92-4.10 (2H, m), 4.20 (2H, d, J=13 Hz), 4.24-4.43 (2H, m), 4.94-5.11 (2H, m), 6.99 (2H, dd, J=8, 2 Hz), 7.08 (2H, d, J=2 Hz), 7.31 (2H, d, J=8 Hz), 7.34 (4H, d, J=8 Hz), 7.68 (4H, d, J=8 Hz); MS (DCI/NH$_3$): m/z 401 (M+H)$^+$. Anal. Calculated

Example 30

2,7-Bis-[(1R,5R)-6-methyl-3,6-diazabicyclo[3.2.0]hept-3-yl]-fluoren-9-one

Example 30A

(1R,5R)-6-Methyl-3,6-diazabicyclo[3.2.0]heptane-3-carboxylic acid benzyl ester To a solution of (1R,5R)-3,6-diazabicyclo[3.2.0]heptane-3-carboxylic acid benzyl ester (14.2 g, 61.2 mmol; prepared according to patent WO 2001081347) and aqueous formaldehyde (38%, 100 mL, 1.38 mol; Fisher) in water (100 mL) was added sodium triacetoxyborohydride (25.8 g, 122 mmol; Aldrich). The mixture was stirred at room temperature until the reaction was complete according to HPLC analysis. The mixture was extracted with chloroform (3×100 mL) and the organic phase was washed with brine (100 mL) and concentrated under reduced pressure to afford the title compound (13.6 g, 55.3 mmol; 90% yield): $^1$H NMR (300 MHz, $CD_3OD$) δ ppm 7.26-7.42 (5H, m), 5.15 (2H, s), 3.85 (1H, dd, J=7, 4 Hz), 3.69-3.79 (1H, m), 3.42-3.55 (1H, m), 3.13-3.25 (4H, m), 2.98-3.09 (1H, m), 2.32 (3H, s); MS (DCI/$NH_3$) m/z 247 (M+H)$^+$.

Example 30B

(1R,5R)-6-Methyl-3,6-diazabicyclo[3.2.0]heptane

A solution of the product of Example 30A (13.6 g, 55.3 mmol) in methanol (150 mL) was treated with 10% Pd/C (1 g; Aldrich) under hydrogen balloon atmosphere for 2 h. After removing the catalyst by filtration, concentration of the mixture under reduced pressure provided the title compound as an oil (5.7 g, 50.9 mmol; 92% yield): $^1$H NMR (300 MHz, $CD_3OD$) δ ppm 3.83 (1H, dd, J=6, 4 Hz), 3.22 (1H, d, J=8 Hz), 2.90-3.17 (4H, m), 2.67 (3H, dd, J=13, 7 Hz), 2.37-2.48 (1H, m), 2.35 (3H, s); MS (DCI/$NH_3$) m/z 113 (M+H)$^+$.

Example 30C

2,7-Bis-[(1R,5R)-6-methyl-3,6-diazabicyclo[3.2.0]hept-3-yl]-fluoren-9-one

A mixture of the product of Example 30B (250 mg, 2.2 mmol), 2,7-dibromofluoren-9-one (100 mg, 0.30 mmol; Aldrich), sodium tert-butoxide (200 mg, 2.08 mmol; Aldrich), $Pd_2(dba)_3$ (30 mg, 0.03 mmol; Alfa) and (dl)-BINAP (60 mg, 0.09 mmol; Strem) in dry toluene (5 mL) was stirred at 80° C. under nitrogen for 16 h. The reaction mixture was concentrated under vacuum and purified by flash chromatography (80 g silica gel, 1:10:89 $NH_4OH$-MeOH—$CH_2Cl_2$) to afford the title compound (40 mg, 0.10 mmol; 33% yield): $^1$H NMR (300 MHz, $CD_3OD$) δ 7.42 (2H, d, J=8 Hz), 7.17 (2H, d, J=2 Hz), 7.03 (2H, dd, J=8, 2 Hz), 4.87-4.97 (2H, m), 4.12-4.28 (4H, m), 3.86-4.05 (4H, m), 3.43-3.56 (2H, m), 3.11 (2H, dd, J=13, 5 Hz), 3.03 (2H, dd, J=11, 6 Hz), 2.94 (6H, s); MS (DCI/$NH_3$): m/z 401 (M+1)$^+$.

Example 31

2,7-Bis-[(S)-3-dimethylaminopyrrolidin-1-yl]-fluoren-9-one dihydrochloride

Example 31A

2,7-Bis-[(S)-3-dimethylaminopyrrolidin-1-yl]-fluoren-9-one

A catalyst solution was prepared by mixing tris(dibenzylideneacetone)dipalladium ($Pd_2(dba)_3$; 36 mg, 0.040 mmol; Alfa) and racemic 2,2'-bis(diphenylphosphino)-1,1'-binaphthyl (BINAP; 62 mg, 0.10 mmol; Strem) in toluene (1 mL) and heating the mixture at 80° C. for 15 min. The solution was cooled, and then added to a mixture of (S)-3-dimethylaminopyrrolidine (320 μL, 2.53 mmol; Aldrich) and 2,7-dibromofluoren-9-one (338 mg, 1.00 mmol; Aldrich) in toluene (5 mL). Sodium tert-butoxide (200 mg, 2.08 mmol; Aldrich) was then added, and the reaction mixture was flushed with nitrogen and heated to 80° C. for 4 h. After cooling to room temperature, the mixture was filtered through diatomaceous earth, rinsing with EtOAc, and purified by chromatography (80 g silica gel, gradient of 2-12% gradient of $NH_4OH$-MeOH (1:10) in $CH_2Cl_2$) to afford the title compound as a dark blue solid (153 mg, 0.378 mmol; 38% yield): $^1$H NMR (300 MHz, $CDCl_3$) δ ppm 7.14 (d, J=8 Hz, 2H), 6.82 (d, J=2 Hz, 2H), 6.48 (dd, J=8, 2 Hz, 2H), 3.42-3.57 (m, 4H), 3.36 (dt, J=10, 7 Hz, 2H), 3.20 (t, J=9 Hz, 2H), 2.77-2.91 (m, 2H), 2.32 (s, 12H), 2.17-2.28 (m, 2H), 1.93 (dq, J=12, 9, 9 Hz, 2H); MS (DCI/$NH_3$) m/z 405 (M+H)$^+$.

Example 31B

2,7-Bis-[(S)-3-dimethylaminopyrrolidin-1-yl]-fluoren-9-one dihydrochloride

A suspension of the title compound from Example 31A (153 mg, 0.378 mmol) in EtOH (1 mL) was treated with a solution of HCl-dioxane (190 μL, 0.76 mmol; 4 M; Aldrich), then diluted with EtOAc and stirred for 4 h. The resulting solid was collected by filtration and recrystallized from hot MeOH-EtOH-EtOAc to afford the title compound (103 mg, 0.21 mmol; 56% yield): $^1$H NMR (300 MHz, $D_2O$) δ ppm 7.30 (d, J=8 Hz, 2H), 6.89 (d, J=2 Hz, 2H), 6.73 (dd, J=8, 2 Hz, 2H), 4.00-4.09 (m, 2H), 3.55-3.82 (m, 6H), 3.34-3.46 (m, 2H), 2.99 (s, 12H), 2.51-2.67 (m, 2H), 2.21-2.36 (m, 2H); MS (DCI/$NH_3$) m/z 405 (M+H)$^+$; Anal. $C_{25}H_{32}N_4O.2HCl.0.7H_2O$: C, H, N.

Example 32

{3-[7-(3-Diethylaminoprop-1-ynyl)-5,5-dioxo-5H-5λ$^6$-dibenzothiophen-3-yl]-prop-2-ynyl}-diethylamine dihydrochloride

Example 32A

{3-[7-(3-Diethylamino-prop-1-ynyl)-5,5-dioxo-5H-5λ$^6$-dibenzothiophen-3-yl]-prop-2-ynyl}-diethylamine A mixture of 3,7-dibromodibenzothiophene 5,5-dioxide (0.33 g, 0.88 mmol; see *J. Med. Chem.* 1978, 21, 1084), 3-diethylamino-1-propyne (0.5 mL, 3.4 mmol; Lancaster), triethylamine (0.6 mL, 4.2 mmol; Acros), dichlorobis(triphenylphosphino)palladium (II) ($Cl_2Pd(PPh_3)_2$; 25 mg, 0.035 mmol; Aldrich), and copper (I) iodide (38 mg, 0.20 mmol; Aldrich) in DMF (10 mL) was heated to 65° C. for 60 h. The reaction mixture was diluted with EtOAc, washed with water and brine, and dried over $Na_2SO_4$. The residue was purified by chromatography (16 g silica gel, 2-7% gradient MeOH in $CH_2Cl_2$ to afford the title compound (0.31 g, 0.71 mmol, 82% yield): MS ($DCI/NH_3$) m/z 435 $(M+H)^+$.

Example 32B

{3-[7-(3-Diethylaminoprop-1-ynyl)-5,5-dioxo-5H-5λ⁶-dibenzothiophen-3-yl]-prop-2-ynyl}-diethylamine dihydrochloride The product from Example 32A (310 mg, 0.71 mmol) was converted to the title compound (205 mg, 0.41 mmol, 59%) according to the procedure described in Example 10B: $^1$H NMR (300 MHz, $CD_3OD$) δ ppm 1.41 (t, J=7 Hz, 8H), 3.42 (q, J=7 Hz, 12H), 4.44 (s, 4H), 7.92 (dd, J=8, 2 Hz, 2H), 8.08 (d, J=1 Hz, 2H), 8.13 (d, J=8 Hz, 2H); MS ($DCI/NH_3$) m/z 435 $(M+H)^+$; Anal. $C_{26}H_{30}N_2O_2S \cdot 2HCl$: C, H, N.

Example 33

2,7-Bis-[3,7-diazabicyclo[3.3.0]octan-3-yl]-dibenzothiophene-5,5-dioxide bis(trifluoroacetate)

Example 33A 2,7-Bis-[N-Boc-3,7-diazabicyclo[3.3.0]octan-3-yl]-dibenzothiophene-5,5-dioxide A catalyst solution was prepared by mixing tris(dibenzylideneacetone)dipalladium ($Pd_2(dba)_3$; 58 mg, 0.064 mmol; Alfa) and racemic 2,2'-bis(diphenylphosphino)-1,1'-binaphthyl (BINAP; 80 mg, 0.13 mmol; Strem) in toluene (4 mL) and heating the mixture to 80° C. for 15 min. The solution was cooled, and then added to a mixture of 3-Boc-3,7-diazabicyclo[3.3.0]octane (510 mg, 2.28 mmol; see WO 0181347) and 3,7-dibromo-dibenzothiophene-5,5-dioxide (0.60 g, 1.60 mmol; see *J. Med. Chem.* 1978, 21, 1084), in toluene (5 mL). $Cs_2CO_3$ (1.04 g, 3.2 mmol; Aldrich) was then added, and the reaction mixture was flushed with nitrogen and heated to 80-85° C. overnight (16 h). After cooling to room temperature, the mixture was filtered through diatomaceous earth and purified by chromatography (80 g silica gel, 10-100% gradient of EtOAc in hexanes) to afford the title compound (280 mg, 0.44 mmol, 27% yield): MS ($DCI/NH_3$): m/z 636 $(M)^+$, 654 $(M+18)^+$.

Example 33B 2,7-Bis-[3,7-diazabicyclo[3.3.0]octan-3-yl]-dibenzothiophene-5,5-dioxide bis(trifluoroacetate)

The product of Example 33A (280 mg, 0.44 mmol) in $CH_2Cl_2$ (20 mL) was cooled to 0° C. and treated with trifluoroacetic acid (5 mL; EM Science). After 15 min the ice bath was removed and the reaction mixture stirred at room temperature overnight. Volatiles were removed under reduced pressure. The residue was purified by preparative HPLC [Waters XTerra $RP_{18}$ 30×100 mm column, gradient 5-95% MeCN-aq. TFA (0.1%)] to afford the title compound (81.7 mg, 0.36 mmol, 40% yield): $^1$H NMR (300 MHz, $CD_3OD$) δ ppm 3.22-3.30 (m, 6H), 3.43-3.66 (m, 14H), 6.97 (dd, J=8, 2 Hz, 2H), 7.05 (d, J=2 Hz, 2H), 7.66 (d, J=8 Hz, 2H); MS ($DCI/NH_3$) m/z 437 $(M+H)^+$; Anal. $C_{24}H_{28}N_4O_2S \cdot 2C_2HF_3O_2 \cdot 0.75H_2O$: C, H, N.

Example 34

2-[(S)—Pyrrolidin-3-yloxy]-fluoren-9-one p-toluenesulfonate

A solution of 2-[(S)—N-Boc-pyrrolidin-3-yloxy]-fluoren-9-one (315 mg, 0.863 mmol; Example 4A) and p-toluenesulfonic acid monohydrate (165 mg, 0.868 mmol; Aldrich) in EtOAc (15 mL) was heated to reflux. A precipitate began to form after about 30 min of heating. After 18 h, the mixture was cooled to room temperature and the yellow crystals were collected by filtration to afford the title compound (334 mg, 0.763 mmol; 88% yield): $^1$H NMR (300 MHz, $CD_3OD$) δ ppm 7.67-7.73 (m, J=8 Hz, 2H), 7.55-7.63 (m, 3H), 7.52 (dt, J=7, 1 Hz, 1H), 7.27 (dt, J=7, 1 Hz, 1H), 7.20-7.24 (m, J=5, 3 Hz, 3H), 7.14 (dd, J=8, 3 Hz, 1H), 5.24-5.30 (m, 1H), 3.44-3.63 (m, 4H), 2.29-2.39 (m, 5H); MS ($DCI/NH_3$) m/z 266 $(M+H)^+$; Anal. $C_{17}H_{15}NO_2 \cdot C_7H_8O_3S$: C, H, N.

Example 35

2-[(S)-1-Methylpyrrolidin-3-yloxy]-fluoren-9-one p-toluenesulfonate

Example 35A

2-[(S)-1-Methylpyrrolidin-3-yloxy]-fluoren-9-one

A solution of the product of Example 34C (196 mg, 0.447 mmol) in aqueous formaldehyde (37%, 2 mL; Fisher) was chilled to 0° C. and treated with $NaBH(OAc)_3$. The ice bath was removed and the reaction mixture was stirred overnight. After quenching with 1 N HCl and washing with $Et_2O$, the aqueous phase was brought to about pH 10 by addition of 1 N NaOH, and then extracted with $Et_2O$ (3×10 mL). The organic extracts were combined and concentrated under vacuum, and the residue was purified by flash chromatography (35 g silica gel, 2-20% gradient of $NH_4OH$-MeOH (1:10) in $CH_2Cl_2$) to afford the title compound (136 mg, 100% yield): $^1$H NMR (300 MHz, $CD_3OD$) δ ppm 7.52-7.57 (m, 3H), 7.49 (td, J=7, 1 Hz, 1H), 7.24 (td, J=7, 1 Hz, 1H), 7.12 (d, J=3 Hz, 1H), 7.04 (dd, J=8, 3 Hz, 1H), 4.93-5.02 (m, 1H), 2.80-2.95 (m, 3 H), 2.40 (s, 3H), 2.33-2.54 (m, 2H), 1.92-2.04 (m, 1H); MS ($DCI/NH_3$) m/z 280 $(M+H)^+$.

Example 35B

2-[(S)-1-Methylpyrrolidin-3-yloxy]-fluoren-9-one p-toluenesulfonate

A solution of the product from Example 35A (125 mg, 0.45 mmol) in EtOH-EtOAc (2 mL, 1:10) was treated with p-toluenesulfonic acid monohydrate (91 mg, 0.48 mmol; Aldrich). The mixture was stirred 2 h and the yellow crystals were collected by filtration to afford the title compound (179 mg, 0.386 mmol; 86% yield): $^1$H NMR (300 MHz, $CD_3OD$) δ ppm 7.67-7.73 (m, 2H), 7.56-7.64 (m, 3H), 7.52 (td, J=7, 1 Hz, 1H), 7.28 (td, J=7, 1 Hz, 1H), 7.19-7.25 (m, 3H), 7.13 (dd, J=8, 3 Hz, 1H), 5.28 (t, J=5 Hz, 1H), 3.03 (s, 3H), 2.36 (s, 3H);

MS (DCI/NH$_3$) m/z 280 (M+H)$^+$; Anal. C$_{18}$H$_{17}$NO$_2$.C$_7$H$_8$O$_3$S.0.7H$_2$O: C, H, N.

Example 36

2-(Piperidin-4-yloxy)-fluoren-9-one trifluoroacetate

Example 36A 2-(Piperidin-4-yloxy)-fluoren-9-one

A solution of the byproduct mixture from Example 23A (361 mg) in methanol (25 mL) was treated with 10% Pd/C (50 mg) under a hydrogen balloon for 16 h. The catalyst was filtered off and the resulting solution was concentrated to afford the title compound (120 mg, 0.43 mmol): MS (DCI/NH$_3$): m/z 280 (M+1)$^+$.

Example 36B 2-(Piperidin-4-yloxy)-fluoren-9-one trifluoroacetate

The product of Example 36A (120 mg, 0.43 mmol) was purified by preparative HPLC [Waters XTerra RP$_{18}$ 30×100 mm column, gradient 5-95% MeCN-aq. TFA (0.1%)] to afford the title compound after evaporation of solvent (21 mg, 0.053 mmol, 12% yield): $^1$H NMR (300 MHz, CD$_3$OD) δ ppm 1.97-2.12 (m, 2H), 2.13-2.26 (m, 2H), 3.17-3.30 (m, 2H), 3.36-3.48 (m, 2H), 4.73-4.83 (m, 1H), 7.16 (dd, J=8, 3 Hz, 1H), 7.22-7.33 (m, 2H), 7.46-7.65 (m, 4H); MS (DCI/NH$_3$) m/z 280 (M+H)$^+$; Anal. C$_{26}$H$_{30}$N$_2$O$_2$S.C$_2$HF$_3$O$_2$.0.5H$_2$O: C, H, N.

Example 37

2-(1-Azabicyclo[2.2.2]oct-3-ylamino)-fluoren-9-one di-p-toluenesulfonate

Example 37A 2-(1-Azabicyclo[2.2.2]oct-3-ylamino)-fluoren-9-one

A suspension of 2-aminofluorene-9-one (400 mg, 2.05 mmol; Aldrich) and anhydrous sodium sulfate (3.0 g, 21 mmol; EM Science) in acetic acid (10 mL) was stirred for 15 min and then treated with sodium triacetoxyborohydride (1.3 g, 6.13 mmol; Aldrich). After stirring overnight, the reaction mixture was basified with saturated aqueous Na$_2$CO$_3$ and extracted with EtOAc (3×). The combined organic phases were concentrated under vacuum and purified by flash chromatography (80 g silica gel, 1-16% gradient of NH$_4$OH-MeOH (1:10) in CH$_2$Cl$_2$) to afford the title compound (492 mg, 1.62 mmol; 79% yield): $^1$H NMR (300 MHz, CD$_3$OD) δ ppm 7.35-7.47 (m, 3H), 7.33 (d, J=8 Hz, 1H), 7.11 (td, J=7, 2 Hz, 1H), 6.86 (d, J=2 Hz, 1H), 6.70 (dd, J=8, 2 Hz, 1H), 3.57-3.67 (m, 1H), 3.32-3.40 (m, 1H), 2.74-3.00 (m, 4H), 2.60 (ddd, J=14, 5, 1 Hz, 1H), 1.67-2.06 (m, 4H), 1.41-1.55 (m, 1H); MS (DCI/NH$_3$) m/z 305 (M+H)$^+$.

Example 37B 2-(1-Azabicyclo[2.2.2]oct-3-ylamino)-fluoren-9-one di-p-toluenesulfonate A dark red solution of the product of Example 37A (492 mg, 1.62 mmol) in EtOH-EtOAc (5 mL, 1:10) was treated with p-toluenesulfonic acid monohydrate (308 mg, 1.62 mmol; Aldrich). The mixture was stirred 2 h and the resulting crystals were collected by filtration to afford the title compound (277 mg, 0.42 mmol; 26% yield): $^1$H NMR (300 MHz, CD$_3$OD) δ ppm 7.67-7.73 (m, 4H), 7.38-7.51 (m, 4H), 7.20-7.25 (m, 4H), 7.16 (ddd, J=7, 6, 3 Hz, 1H), 6.91 (d, J=2 Hz, 1H), 6.78 (dd, J=8, 2 Hz, 1H), 4.00-4.08 (m, 1H), 3.78-3.88 (m, 1H), 3.32-3.42 (m, 4H), 3.07 (ddd, J=13, 5, 2 Hz, 1H), 2.36 (s, 6H), 2.31-2.35 (m, 1H), 2.18-2.30 (m, 1H), 2.10 (dt, J=8, 3 Hz, 2H), 1.82-1.96 (m, 1H); MS (DCI/NH$_3$) m/z 305 (M+H)$^+$; Anal. C$_{20}$H$_{20}$N$_2$O.2C$_7$H$_8$O$_3$S.0.2H$_2$O: C, H, N.

Example 38

2-[(1R,5R)-6-Methyl-3,6-diazabicyclo[3.2.0]hept-3-yl]-fluoren-9-one hydrobromide The product of Example 57B (100 mg, 0.27 mmol) was dissolved in methanol (5 mL) and treated with 10% Pd/C (50 mg; Aldrich) under a hydrogen balloon atmosphere for 30 min. After removing the catalyst by filtration, the solution was concentrated under vacuum. EtOAc (4 mL) was added and the mixture was stirred at room temperature for 16 h. The resulting solid was collected by centrifugation and dried to afford the title compound (43 mg, 0.1 mmol; 37% yield): MS (DCI/NH$_3$): m/z 291 (M+1)$^+$.

Example 39

2-[(1S,5S)-3,6-Diazabicyclo[3.2.0]hept-3-yl]-fluoren-9-one p-toluenesulfonate

Example 39A 3-(9-Oxo-9H-fluoren-2-yl)-(1S,5S)-3,6-diazabicyclo[3.2.0]heptane-6-carboxylic acid tert-butyl ester A mixture of the product of Example 19L (300 mg, 1.5 mmol), 2-bromofluoren-9-one (190 mg, 0.73 mmol; Aldrich), sodium tert-butoxide (200 mg, 2.08 mmol; Aldrich), tris(dibenzylideneacetone)dipalladium (Pd$_2$(dba)$_3$; 30 mg, 0.03 mmol; Alfa) and racemic 2,2'-bis(diphenylphosphino)-1,1'-binaphthyl (BINAP; 60 mg, 0.09 mmol; Strem) in dry toluene (10 mL) was stirred at 90° C. under nitrogen for 16 h, then this mixture was concentrated under vacuum and purified by flash chromatography (80 g silica gel, 40:60 gradient of EtOAc in hexanes) to afford the title compound (270 mg, 0.72 mmol; 98% yield): $^1$H NMR (300 MHz, CD$_3$OD) δ ppm 7.40-7.57 (4H, m), 6.85-7.27 (3H, m), 4.79-4.90 (1H, m), 3.91-4.17 (2H, m), 3.75-3.87 (1H, m), 3.53-3.69 (1H, m), 2.83-3.27 (3H, m), 1.46 (9H, s); MS (DCI/NH$_3$): m/z 377 (M+1)$^+$.

Example 39B

2-[(1S,5S)-3,6-Diazabicyclo[3.2.0]hept-3-yl]-fluoren-9-one

The product of Example 39A (270 mg, 0.72 mmol) was dissolved in CH$_2$Cl$_2$ (5 mL) and treated with trifluoroacetic acid (1 mL) at room temperature for 30 min. The mixture was concentrated under vacuum and purified by flash chromatography (40 g silica gel, 1:10:89 NH$_4$OH-MeOH—CH$_2$Cl$_2$) to afford the title compound (130 mg, 0.47 mmol; 30% yield): $^1$H NMR (300 MHz, CD$_3$OD) δ ppm 7.39-7.52 (4H, m), 7.12-7.19 (1H, m), 7.09 (1H, d, J=2 Hz), 6.93 (1H, dd, J=8, 2

Hz), 4.56 (1H, dd, J=7, 5 Hz), 3.76-3.94 (3H, m), 3.33-3.44 (2H, m), 2.99-3.15 (2H, m); MS (DCI/NH$_3$): m/z 277 (M+1)$^+$.

Example 39C

2-[(1S,5S)-3,6-Diazabicyclo[3.2.0]hept-3-yl]-fluoren-9-one p-toluenesulfonate

A mixture of the product of Example 39B (60 mg, 0.22 mmol) and p-toluenesulfonic acid monohydrate (48 mg, 0.25 mmol) was stirred in EtOAc-EtOH (4 mL, 10:1) at room temperature for 16 h. The resulted solid was collected and dried under vacuum to afford the title compound (63 mg, 0.13 mmol; 58% yield): $^1$H NMR (300 MHz, CD$_3$OD) δ ppm 7.70 (2H, d, J=8 Hz), 7.44-7.57 (4H, m), 7.17-7.26 (4H, m), 7.05 (1H, dd, J=8, 3 Hz), 5.03 (1H, dd, J=7, 5 Hz), 4.26 (1H, dd, J=11, 9 Hz), 4.16 (1H, d, J=13 Hz), 3.94 (1H, d, J=11 Hz), 3.76 (1H, dd, J=11, 5 Hz), 3.44-3.55 (1H, m), 3.15 (1H, dd, J=13, 5 Hz), 3.06 (1H, dd, J=11, 6 Hz), 2.36 (3H, s): MS (DCI/NH$_3$): m/z 277 (M+1)$^+$. Anal. Calcd. for C$_{18}$H$_{16}$N$_2$O.1.3C$_7$H$_8$O$_3$S: C, 65.07; H, 5.32; N, 5.60. Found: C, 64.88; H, 5.20; N, 5.68.

Example 40

2-[(1S,5S)-6-Methyl-3,6-diazabicyclo[3.2.0]hept-3-yl]-fluoren-9-one p-toluenesulfonate

Example 40A

2-[(1S,5S)-6-Methyl-3,6-diazabicyclo[3.2.0]hept-3-yl]-fluoren-9-one

A solution of the product of Example 39B (70 mg, 0.25 mmol) in water (2 mL), was treated with formaldehyde (38% aq., 3 mL) and NaBH(OAc)$_3$ (250 mg, 1.18 mmol; Aldrich). After stirring at room temperature for 60 h, the reaction mixture was concentrated under vacuum and purified by flash chromatography (40 g silica gel, 1:10:89 NH$_4$OH-MeOH—CH$_2$Cl$_2$) to afford the title compound (57 mg, 0.20 mmol; 91% yield): $^1$H NMR (300 MHz, CD$_3$OD) δ ppm 7.37-7.51 (4H, m), 7.10-7.19 (1H, m), 7.02 (1H, d, J=2 Hz), 6.85 (1H, dd, J=8, 2 Hz), 4.02 (1H, dd, J=6, 5 Hz), 3.72-3.82 (2H, m), 3.15-3.40 (4H, m), 3.03 (1H, dd, J=11, 4 Hz), 2.39 (3H, s); MS (DCI/NH$_3$): m/z 291 (M+1)$^+$.

Example 40B

2-[(1S,5S)-6-Methyl-3,6-diazabicyclo[3.2.0]hept-3-yl]-fluoren-9-one p-toluenesulfonate

A mixture of product of Example 40A (57 mg, 0.20 mmol) and p-toluenesulfonic acid monohydrate (47 mg, 0.25 mmol) was stirred in EtOAc-EtOH (4 mL, 10:1) at room temperature for 16 h. The resulting solid was collected and dried under vacuum to afford the title compound (58 mg, 0.11 mmol; 55% yield): $^1$H NMR (300 MHz, CD$_3$OD) δ ppm 7.70 (2H, d, J=8 Hz), 7.44-7.61 (4H, m), 7.17-7.28 (4H, m), 7.02-7.13 (1H, m), 4.86-4.93 (1H, m), 3.90-4.26 (3H, m), 3.44-3.56 (1H, m), 3.30-3.35 (1H, m), 3.03-3.20 (2H, m), 2.76-3.01 (3H, m), 2.36 (3H, s); MS (DCI/NH$_3$): m/z 291 (M+1)$^+$. Anal. Calcd. for C$_{19}$H$_{18}$N$_2$O.1.3C$_7$H$_8$O$_3$S0.6H$_2$O: C, 64.28; H, 5.68; N, 5.34. Found: C, 63.98; H, 5.46; N, 5.52.

Example 41

2-(1,4-Diazabicyclo[3.2.2]non-4-yl)-fluoren-9-one p-toluenesulfonate

Example 41A

2-(1,4-Diazabicyclo[3.2.2]non-4-yl)-fluoren-9-one

A catalyst solution was prepared by mixing tris(dibenzylideneacetone)dipalladium (Pd$_2$(dba)$_3$; 20 mg, 0.022 mmol; Alfa) and racemic 2,2'-bis(diphenylphosphino)-1,1'-binaphthyl (BINAP; 38 mg, 0.061 mmol; Strem) in toluene (1 mL) and heating the mixture to 90° C. for 15 min. The solution was cooled, and then added to a mixture of 1,4-diazabicyclo[3.2.2]nonane (112 mg, 0.889 mmol; see *J. Med. Chem.* 1993, 36, 2311) and 2-bromofluoren-9-one (320 mg, 1.24 mmol; Aldrich) in toluene (3 mL). Sodium tert-butoxide (120 mg, 1.25 mmol; Aldrich) was then added, and the reaction mixture was flushed with nitrogen and heated to 80-85° C. overnight. After cooling to room temperature, the mixture was filtered through diatomaceous earth and purified by chromatography (35 g silica gel, 1-16% gradient of NH$_4$OH-MeOH (1:10) in CH$_2$Cl$_2$) to afford the title compound (116 mg, 0.382 mmol; 43% yield): $^1$H NMR (300 MHz, CD$_3$OD) δ ppm 7.48 (d, J=7 Hz, 1H), 7.39-7.44 (m, 3H), 7.14 (ddd, J=7, 6, 3 Hz, 1H), 7.09 (d, J=3 Hz, 1H), 6.93 (dd, J=8, 3 Hz, 1H), 4.10-4.17 (m, 1H), 3.66 (dd, J=6, 5 Hz, 2H), 2.95-3.17 (m, 6H), 2.09-2.23 (m, 2H), 1.84 (ddd, J=19, 10, 5 Hz, 2H); MS (DCI/NH$_3$): m/z 305 (M+1)$^+$.

Example 41B

2-(1,4-Diazabicyclo[3.2.2]non-4-yl)-fluoren-9-one p-toluenesulfonate

A mixture of product of Example 41A (116 mg, 0.382 mmol) and p-toluenesulfonic acid monohydrate (75 mg, 0.40 mmol) was stirred in EtOAc-EtOH (2 mL, 10:1) at room temperature for 2 h. The resulting solid was collected and dried under vacuum to afford the title compound as a reddish solid (112 mg, 0.227 mmol; 59% yield): $^1$H NMR (300 MHz, CD$_3$OD) δ ppm 7.68-7.73 (m, 2H), 7.45-7.54 (m, 4 H), 7.16-7.25 (m, 4H), 7.04 (dd, J=8, 3 Hz, 1H), 4.37 (ddd, J=7, 5, 2 Hz, 1H), 3.86 (t, J=6 Hz, 2H), 3.49-3.62 (m, 6H), 2.30-2.44 (m, 5H), 2.10-2.24 (m, 2H); MS (DCI/NH$_3$): m/z 305 (M+1)$^+$; Anal. C$_{20}$H$_{20}$N$_2$O'C$_7$H$_8$O$_3$S.H$_2$O: C, H, N.

Example 42

2-(9H-Fluoren-2-yl)-octahydropyrrolo[3,4-c]pyrrole p-toluenesulfonate

Example 42A

5-(9H-Fluoren-2-yl)-hexahydropyrrolo[3,4-c]pyrrole-2-carboxylic acid tert-butyl ester

A mixture of 3-Boc-3,7-diazabicyclo[3.3.0]octane (340 mg, 1.6 mmol; see WO 0181347), 2-bromofluorene (0.47 g, 1.9 mmol), tris(dibenzylideneacetone)dipalladium (0) (Pd$_2$(dba)$_3$; 44 mg, 0.048 mmol; Strem), racemic-2,2'-bis(diphenylphosphino)-1,1'-binaphthyl (BINAP; 50 mg, 0.080 mmol; Strem) and Cs$_2$CO$_3$ (1.0 g, 3.2 mmol; Aldrich) in toluene (25 mL) in a sealed tube was warmed to 85° C. and stirred for 18 h. The material was cooled to ambient temperature, filtered, concentrated under reduced pressure and purified by flash chromatography (silica gel, 50% gradient of EtOAc in hexanes) to afford the title compound (350 mg, 0.93 mmol; 58% yield): MS (DCI/NH$_3$) m/z 377 (M+H)$^+$.

Example 42B 2-(9H-Fluoren-2-yl)-octahydropyrrolo[3,4-c]pyrrole p-toluenesulfonate The product of Example 42A (240 mg, 0.64 mmol) in CH$_2$Cl$_2$ (6 mL) at 0° C. was treated with trifluoroacetic acid (4 mL; EM Science). The mixture was warmed to ambient temperature and stirred for 2 h, then concentrated and purified by flash chromatography (silica gel, 9:1:0.1 CH$_2$Cl$_2$-CH$_3$OH—NH$_4$OH) to afford 2-(9H-fluoren-2-yl)-octahydropyrrolo[3,4-c]pyrrole as its free base (160 mg, 0.58 mmol; 90% yield).

A portion of this material (50 mg, 0.18 mmol) was dissolved in 1:9 EtOH-EtOAc (3 mL) and treated with p-toluenesulfonic acid monohydrate (34 mg, 0.18 mmol). The resulting precipitate was isolated by filtration to afford the title compound (70 mg, 0.13 mmol; 73% yield): $^1$H NMR (300 MHz, CD$_3$OD) δ ppm 2.36 (s, 3H), 3.28 (m, 6H), 3.58 (m, 4H), 3.81 (s, 2H), 6.80 (m, 1H), 7.00 (m, 1H), 7.15 (m, 1H), 7.22 (m, 2H), 7.27 (m, 1H), 7.45 (m, 1H), 7.63 (m, 2H), 7.70 (m, 2H); MS (DCI/NH$_3$) m/z 277 (M+H)$^+$; Anal. calculated for C$_{19}$H$_{20}$N$_2$.1.5C$_7$H$_8$O$_3$S: C, 66.27; H, 6.03; N, 5.24; Found: C, 66.10; H, 6.14; N, 5.47.

Example 43

(1-Azabicyclo[2.2.2]oct-3-yl)-(9H-fluoren-2-yl)-amine di-p-toluenesulfonate

Example 43A (1-Azabicyclo[2.2.2]oct-3-yl)-(9H-fluoren-2-yl)-amine

The filtrate from Example 37B was concentrated and redissolved in MeOH (20 mL). The solution was acidified with 2 drops conc. HCl and treated with 10% Pd/C under a hydrogen balloon atmosphere for 4 d. After removal of the catalyst by filtration, the residue was purified by flash chromatography (35 g silica gel, 1-12% gradient of NH$_4$OH-MeOH (1:10) in CH$_2$Cl$_2$) to provide the crude product (211 mg). This material was purified further by reverse-phase HPLC (30×100 mm Symmetry-C$_8$ column, aq. TFA (0.1%)-MeCN). Fractions containing the desired compound were combined, adjusted to ~pH 10 with Na$_2$CO$_3$, and extracted with CH$_2$Cl$_2$ to afford the title compound (48 mg, 0.17 mmol): MS (DCI/NH$_3$) m/z 291 (M+H)$^+$.

Example 43B (1-Azabicyclo[2.2.2]oct-3-yl)-(9H-fluoren-2-yl)-amine di-p-toluenesulfonate A solution of the product of Example 43A (47 mg, 0.16 mmol) in EtOH-EtOAc (5 mL, 1:10) was treated with a solution of p-toluenesulfonic acid monohydrate (60 mg, 0.32 mmol; Aldrich) in EtOAc (1 mL). The mixture was stirred overnight, then heated briefly to 50° C. and sonicated until a solid formed. The resulting crystals were collected by filtration to afford the title compound (73 mg, 0.12 mmol; 71% yield): $^1$H NMR (300 MHz, CD$_3$OD) δ ppm 7.65-7.74 (m, 6H), 7.49 (d, J=8 Hz, 1H), 7.31 (t, J=7 Hz, 1H), 7.22 (d, J=8 Hz, 5H), 7.15 (s, 1H), 6.97 (d, J=7 Hz, 1H), 4.08-4.20 (m, 1H), 3.79-3.90 (m, 3H), 3.19-3.55 (m, 5H), 2.25-2.42 (m, 8H), 2.02-2.15 (m, 2H), 1.87-2.00 (m, 1H); MS (DCI/NH$_3$) m/z 291 (M+H)$^+$; Anal. C$_{20}$H$_{22}$N$_2$.2C$_7$H$_8$O$_3$S: C, H, N.

Example 44

(R)-3-(9H-Fluoren-2-yloxy)-1-azabicyclo[2.2.2]octane hydrochloride

Example 44A 2-(1-Azabicyclo[2.2.2]oct-3-yloxy)-9H-fluoren-9-ol

A solution of the product of Example 8A (193 mg, 0.633 mmol) in EtOH (10 mL) was treated with 10% Pd/C (20 mg; Aldrich) under a hydrogen balloon atmosphere for 24 h. After the reaction mixture was filtered to remove the catalyst, the residue was purified by flash chromatography (35 g silica gel, 1-12% gradient of NH$_4$OH-MeOH (1:10) in CH$_2$Cl$_2$) to provide the crude product (123 mg). This material was purified further by reverse-phase HPLC (40×100 mm Symmetry-C$_8$ column, aq. TFA (0.2%)-MeCN). Fractions containing the desired compound were combined, adjusted to ~pH 10 with Na$_2$CO$_3$, and extracted with CH$_2$Cl$_2$ to afford the title compound (84 mg, 0.27 mmol; 43% yield): $^1$H NMR (300 MHz, CD$_3$OD) δ ppm 7.57 (t, J=9 Hz, 3H), 7.32 (t, J=7 Hz, 1H), 7.22 (td, J=7, 1 Hz, 1H), 7.16 (d, J=2 Hz, 1H), 6.92 (dd, J=8, 2 Hz, 1H), 5.47 (s, 1H), 4.53-4.62 (m, 1H), 3.33-3.40 (m, 1H), 2.74-3.03 (m, 5H), 2.19 (td, J=7, 3 Hz, 1H), 1.99-2.13 (m, 1H), 1.62-1.89 (m, 2H), 1.43-1.57 (m, 1H); MS (DCI/NH$_3$) m/z 292 (M+H)$^+$.

Example 44B 3-(9H-Fluoren-2-yloxy)-1-azabicyclo[2.2.2]octane hydrochloride

A solution of the product of Example 44A (84 mg, 0.27 mmol) in MeOH (3 mL) was acidified with one drop conc. HCl and treated with 10% Pd/C (10 mg; Aldrich) under a hydrogen balloon atmosphere for 20 h. The reaction mixture was filtered to remove the catalyst, then the volatiles were removed by concentration under vacuum, and the residue was triturated with EtOH-EtOAc to afford the title compound (60 mg, 0.18 mmol; 65% yield): $^1$H NMR (300 MHz, CD$_3$OD) δ ppm 7.73 (t, J=7 Hz, 2H), 7.51 (d, J=7 Hz, 1H), 7.32 (t, J=7 Hz, 1H), 7.24 (dd, J=7, 1 Hz, 1H), 7.19-7.22 (m, 1H), 7.00 (dd, J=8, 2 Hz, 1H), 4.89-4.98 (m, 1H), 3.77-3.89 (m, 3H), 3.25-3.47 (m, 6H), 2.50-2.59 (m, 1H), 2.29-2.43 (m, 1H), 1.82-2.20 (m, 3H); $^1$H NMR (300 MHz, CD$_3$OD) E 7.73 (t, J=7 Hz, 2H), 7.51 (d, J=7 Hz, 1H), 7.32 (t, J=7 Hz, 1H), 7.24 (dd, J=7, 1 Hz, 1H), 7.19-7.22 (m, 1H), 7.00 (dd, J=8, 2 Hz, 1H), 4.89-4.98 (m, 1H), 3.77-3.89 (m, 3H), 3.25-3.47 (m, 5H), 2.50-2.59 (m, 1H), 2.29-2.43 (m, 1H), 1.82-2.20 (m, 3H); MS (DCI/NH$_3$) m/z 292 (M+H)$^+$; Anal. C$_{20}$H$_{21}$NO_HCl.0.5H$_2$O: C, H, N.

Example 45

(S)-3-(9H-Fluoren-2-yloxy)-1-azabicyclo[2.2.2]octane hydrochloride

Example 45A (S)-3-(9H-Fluoren-2-yloxy)-1-azabicyclo[2.2.2]octane

The product of Example 9A (350 mg, 1.15 mmol) was dissolved in MeOH and acidified with conc. HCl (200 μL).

The solution then was treated with 10% Pd/C (70 mg; Aldrich) under a hydrogen atmosphere (60 psi) at 50° C. for 20 h. The reaction mixture was filtered to remove the catalyst, the volatiles were removed by concentration under vacuum, and the residue was purified by flash chromatography (35 g silica gel, 1-12% gradient of NH$_4$OH-MeOH (1:10) in CH$_2$Cl$_2$) to afford the title compound (230 mg, 0.79 mmol; 69% yield): $^1$H NMR (300 MHz, CD$_3$OD) δ ppm 7.69 (d, J=8 Hz, 2H), 7.49 (d, J=7 Hz, 1H), 7.30 (t, J=7 Hz, 1H), 7.20 (td, J=7, 1 Hz, 1H), 7.13 (d, J=2 Hz, 1H), 6.93 (dd, J=8, 2 Hz, 1H), 4.60 (dt, J=8, 4, 3 Hz, 1H), 3.84 (s, 2H), 3.39 (ddd, J=14, 8, 2 Hz, 1H), 2.80-3.08 (m, 5H), 2.22 (td, J=7, 3 Hz, 1H), 2.03-2.16 (m, 1H), 1.66-1.91 (m, 2H), 1.46-1.60 (m, 1H); MS (DCI/NH$_3$) m/z 292 (M+H)$^+$.

Example 45B (S)-3-(9H-Fluoren-2-yloxy)-1-azabicyclo[2.2.2]octane hydrochloride A solution of the product of Example 45A (230 mg, 0.79 mmol) in EtOH (5 mL) was treated with a solution of HCl in dioxane (200 μL, 0.80 mmol; 4 M; Aldrich). After stirring for 30 min, there was no evidence of solid formation so the reaction was concentrated under vacuum to about one-half its original volume, and EtOAc was added until cloudiness persisted. The mixture was stirred for an additional 30 min and the crystals collected by filtration to afford the title compound (192 mg, 0.58 mmol; 74% yield): $^1$H NMR (300 MHz, CD$_3$OD) δ ppm 7.73 (t, J=7 Hz, 2H), 7.51 (d, J=7 Hz, 1H), 7.32 (t, J=7 Hz, 1H), 7.19-7.27 (m, 2H), 7.00 (dd, J=8, 2 Hz, 1H), 4.90-4.97 (m, 1H), 3.78-3.89 (m, 3H), 3.32-3.49 (m, 6H), 2.55 (td, J=6, 4 Hz, 1H), 2.29-2.43 (m, 1H), 1.83-2.20 (m, 3H); MS (DCI/NH$_3$) m/z 292 (M+H)$^+$; Anal. C$_{20}$H$_{21}$NO_HCl 0.1H$_2$O: C, H, N.

Example 46

(R)-3-(5,5-Dioxo-5H-5λ$^6$-dibenzothiophen-3-yloxy)-1-aza-bicyclo[2.2.2]octane p-toluenesulfonate

Example 46A (R)-3-(5,5-Dioxo-5H-5λ$^6$-dibenzothiophen-3-yloxy)-1-aza-bicyclo[2.2.2]octane A mixture of 3,7-dibromodibenzothiophene-5,5-dioxide (0.60 g, 1.75 mmol; see *J. Med. Chem.* 1978, 21, 1084), (R)-(−)-quinuclidin-3-ol (280 mg, 2.2 mmol; Acros), copper (I) iodide (33 mg, 0.17 mmol; Aldrich), 1,10-phenanthroline (63 mg, 0.35 mol; Aldrich) and powdered cesium carbonate (0.86 g, 2.64 mmol; Aldrich) in toluene (2 mL) was heated to 110° C. with vigorous stirring for 30 h. After cooling to room temperature, the reaction mixture was filtered through diatomaceous earth, rinsing with ethyl acetate and dichloromethane, and the residue purified by flash chromatography (80 g silica gel, 1:10:89 NH$_4$OH-MeOH—CH$_2$Cl$_2$) to afford the title compound (0.23 g, 0.67 mmol; 38% yield): MS (DCI/NH$_3$): m/z 342 (M+1)$^+$.

Example 46B (R)-3-(5,5-Dioxo-5H-5λ$^6$-dibenzothiophen-3-yloxy)-1-aza-bicyclo[2.2.2]octane p-toluenesulfonate The product of Example 46A (0.23 g, 0.67 mmol) was converted to the title compound (287 mg, 0.56 mmol; 83% yield) according to the procedure described in Example 1D: $^1$H NMR (300 MHz, CD$_3$OD) δ ppm 1.84-2.20 (m, 3H), 2.23-2.33 (m, 1H), 2.35 (s, 3H), 2.51-2.62 (m, 1H), 3.28-3.53 (m, 5H), 3.76-3.97 (m, 1H), 4.97-5.14 (m, 1H), 7.22 (d, J=8 Hz, 2H), 7.34 (dd, J=8, 2 Hz, 1H), 7.49 (d, J=2 Hz, 1H), 7.55 (t, J=8 Hz, 1H), 7.71 (t, J=8 Hz, 3H), 7.80 (d, J=8 Hz, 1H), 7.96 (t, J=8 Hz, 2H); MS (DCI/NH$_3$) m/z 342 (M+H)$^+$; Anal. C$_{19}$H$_{19}$N$_0$O$_3$S.C$_7$H$_8$O$_3$S: C, H, N.

Example 47

(S)-3-(5,5-Dioxo-5H-5λ$^6$-dibenzothiophen-3-yloxy)-1-azabicyclo[2.2.2]octane p-toluenesulfonate

Example 47A (S)-3-(5,5-Dioxo-5H-5λ$^6$-dibenzothiophen-3-yloxy)-1-aza-bicyclo[2.2.2]octane A mixture of 3,7-dibromodibenzothiophene-5,5-dioxide (0.60 g, 1.75 mmol; see *J. Med. Chem.* 1978, 21, 1084), (S)-(−)-quinuclidin-3-ol (280 mg, 2.2 mmol; Acros), copper (I) iodide (33 mg, 0.17 mmol; Aldrich), 1,10-phenanthroline (63 mg, 0.35 mol; Aldrich) and powdered cesium carbonate (0.86 g, 2.64 mmol; Aldrich) in toluene (2 mL) was heated to 110° C. with vigorous stirring for 30 h. After cooling to room temperature, the reaction mixture was filtered through diatomaceous earth, rinsing with ethyl acetate and dichloromethane, and the residue purified by flash chromatography (80 g silica gel, 1:10:89 NH$_4$OH-MeOH—CH$_2$Cl$_2$) to afford the title compound (0.37 g, 1.08 mmol; 63% yield): MS (DCI/NH$_3$): m/z 342 (M+1)$^+$.

Example 47B (S)-3-(5,5-Dioxo-5H-5λ$^6$-dibenzothiophen-3-yloxy)-1-aza-bicyclo[2.2.2]octane p-toluenesulfonate The product of Example 47A (0.37 g, 1.08 mmol) was converted to the title compound (424 mg, 0.83 mmol; 77% yield) according to the procedure described in Example 1D: $^1$H NMR (300 MHz, CD$_3$OD) δ ppm 1.84-2.20 (m, 3H), 2.23-2.33 (m, 1H), 2.35 (s, 3H), 2.51-2.62 (m, 1H), 3.28-3.53 (m, 5H), 3.76-3.97 (m, 1H), 4.97-5.14 (m, 1H), 7.22 (d, J=8 Hz, 2H), 7.34 (dd, J=8, 2 Hz, 1H), 7.49 (d, J=2 Hz, 1H), 7.55 (t, J=8 Hz, 1H), 7.71 (t, J=8 Hz, 3H), 7.80 (d, J=8 Hz, 1H), 7.96 (t, J=8 Hz, 2H); MS (DCI/NH$_3$) m/z 342 (M+H)$^+$; Anal. C$_{19}$H$_{19}$N$_2$O$_3$S.C$_7$H$_8$O$_3$S: C, H, N.

Example 48

1-(5,5-Dioxo-5H-5λ$^6$-dibenzothiophen-3-yl)-4-methyl piperazine trifluoroacetate A catalyst solution was prepared by mixing tris(dibenzylideneacetone)dipalladium (Pd$_2$(dba)$_3$; 16 mg, 0.017 mmol; Alfa) and racemic 2,2'-bis(diphenylphosphino)-1,1'-binaphthyl (BINAP; 22 mg, 0.035 mmol; Strem) in toluene (2 mL) and heating the mixture to 80° C. for 15 min. The solution was cooled, and then added to a mixture of N-methylpiperazine (520 μL, 4.69 mmol; Aldrich), and 3,7-dibromodibenzothiophene-5,5-dioxide (0.33 g, 1.88 mmol; see *J. Med. Chem.* 1978, 21, 1084) in toluene (3 mL). Sodium tert-butoxide (120 mg, 1.20 mmol; Aldrich) was then added, and the reaction mixture was flushed with nitrogen and heated to 80-85° C. overnight (16 h). After cooling to room temperature, the mixture was filtered through diatomaceous earth and the residue purified by preparative HPLC [Waters Xterra RP$_{18}$ 30×100 mm column, 5-95% gradient of MeCN-aq. TFA (0.1%)] to afford the title compound (147 mg, 0.36 mmol, 40% yield): $^1$H NMR (300 MHz, CD$_3$OD) δ ppm 2.98 (s, 3H), 3.37-3.55 (m, 8H), 7.35 (dd, J=9, 3 Hz, 1H), 7.48 (d, J=2 Hz, 1H), 7.53 (d, J=7 Hz, 1H), 7.69 (t, J=8 Hz, 1H), 7.77 (d, J=7 Hz, 1H), 7.86-7.95 (m, 2H); MS (DCI/NH$_3$) m/z 315 (M+H)$^+$; Anal. C$_{17}$H$_{18}$N$_2$O$_2$S.C$_2$HF$_3$O$_2$: C, H, N.

Example 49

(1S,5S)-3-(5,5-Dioxo-5H-5λ$^6$-dibenzothiophen-3-yl)-3,6-diazabicyclo[3.2.0]heptane p-toluenesulfonate

Example 49A 3-(5,5-Dioxo-5H-5λ$^6$-dibenzothiophen-3-yl)-3,6-diazabicyclo[3.2.0]heptane-6-carboxylic acid tert-butyl ester A catalyst solution was prepared by mixing tris(dibenzylideneacetone)dipalladium (Pd$_2$(dba)$_3$; 58 mg, 0.064 mmol; Alfa) and racemic 2,2'-bis(diphenylphosphino)-1,1'-binaphthyl (BINAP; 80 mg, 0.13 mmol; Strem) in toluene (4 mL) and heating the mixture to 80° C. for 15 min. The solution was cooled, and then added to a mixture of the product of Example 19L (0.51 g, 2.40 mmol) and 3-bromo-dibenzothiophene-5,5-dioxide (0.60 g, 1.60 mmol; see *J. Med. Chem.* 1978, 21, 1084), in toluene (5 mL). Cs$_2$CO$_3$ (1.04 g, 3.2 mmol; Aldrich) was then added, and the reaction mixture was flushed with nitrogen and heated to 80-85° C. overnight (16 h). After cooling to room temperature, the reaction mixture was filtered through diatomaceous earth, rinsing with ethyl acetate and dichloromethane, and the residue purified by flash chromatography (80 g silica gel, 10-40% gradient of EtOAc in hexanes) to afford the title compound (0.56 g, 1.35 mmol; 84% yield): MS (DCI/NH$_3$) m/z 413 (M+H)$^+$.

Example 49B (1S,5S)-3-(5,5-Dioxo-5H-5λ$^6$-dibenzothiophen-3-yl)-3,6-diazabicyclo[3.2.0]heptane The product of Example 49A (0.56 g, 1.35 mmol) in CH$_2$Cl$_2$ (20 mL) was cooled to 0° C. and treated with trifluoroacetic acid (5 mL; EM Science). After 15 min the ice bath was removed and the reaction mixture stirred at room temperature overnight. Volatiles were removed under reduced pressure. The residue was purified by flash chromatography (80 g silica gel, 1:10:89 NH$_4$OH-MeOH—CH$_2$Cl$_2$) to afford the title compound (0.35 g, 1.12 mmol; 83% yield): MS (DCI/NH$_3$): m/z 313 (M+1)$^+$.

Example 49C (1S,5S)-3-(5,5-Dioxo-5H-5λ$^6$-dibenzothiophen-3-yl)-3,6-diazabicyclo[3.2.0]heptane p-toluenesulfonate The product of Example 49B (0.35 g, 1.12 mmol) was converted to the title compound (205 mg, 0.42 mmol; 38% yield) according to the procedure described in Example 1D: $^1$H NMR (300 MHz, CD$_3$OD) δ ppm 2.34 (s, 3H), 3.16 (dd, J=11, 6 Hz, 1H), 3.26 (dd, J=13, 5 Hz, 2H), 3.46-3.61 (m, 1H), 3.76 (dd, J=11, 5 Hz, 1H), 4.00 (d, J=11 Hz, 1H), 4.16-4.34 (m, 2H), 5.07 (dd, J=7, 5 Hz, 1H), 7.18-7.26 (m, 3H), 7.31 (d, J=2 Hz, 1H), 7.49 (t, J=8 Hz, 1H), 7.68 (t, J=7 Hz, 3H), 7.76 (d, J=6 Hz, 1H), 7.84-7.92 (m, 2H); MS (DCI/NH$_3$) m/z 313 (M+H)$^+$; Anal. C$_{17}$H$_{16}$N$_2$O$_2$S.C$_7$H$_8$O$_3$S.0.33H$_2$O: C, H, N.

Example 50

(1S,5S)-3-(5,5-Dioxo-5H-5λ$^6$-dibenzothiophen-3-yl)-6-methyl-3,6-diazabicyclo[3.2.0]heptane trifluoroacetate A solution of the product of Example 49C (160 mg, 0.37 mmol) in water (2 mL), was treated with formaldehyde (38% aq., 5 mL) and NaBH(OAc)$_3$ (200 mg, 0.94 mmol; Aldrich). After stirring at room temperature for 60 hours, the reaction mixture was concentrated under vacuum and purified by preparative HPLC [Waters XTerra RP$_{18}$ 30×100 mm column, 5-95% gradient of MeCN-aq. TFA (0.1%)] to afford the title compound (97 mg, 0.22 mmol, 60% yield): $^1$H NMR (300 MHz, CD$_3$OD) δ ppm 2.98 (s, 3H), 3.12-3.22 (m, 1H), 3.21-3.30 (m, 2H), 3.43-3.63 (m, 1H), 4.01 (d, J=11 Hz, 1H), 4.30 (d, J=15 Hz, 1H), 4.96 (s, 1H), 7.24 (dd, J=9, 2 Hz, 1H), 7.34 (s, 1H), 7.49 (t, J=7 Hz, 1H), 7.68 (t, J=8 Hz, 1H), 7.77 (d, J=7 Hz, 1H), 7.86-7.95 (m, 2H); MS (DCI/NH$_3$) m/z 327 (M+H)$^+$; Anal. C$_{18}$H$_{18}$N$_2$O$_2$S.C$_2$HF$_3$O$_2$.0.2H$_2$O: C, H, N.

Example 51

4-(5,5-Dioxo-5H-5λ$^6$-dibenzothiophen-3-yl)-1,4-diazabicyclo[3.2.2]nonane p-toluenesulfonate

Example 51A 4-(5,5-Dioxo-5H-5λ$^6$-dibenzothiophen-3-yl)-1,4-diazabicyclo[3.2.2]nonane A catalyst solution was prepared by mixing tris(dibenzylideneacetone)dipalladium (Pd$_2$(dba)$_3$; 15 mg, 0.016 mmol; Alfa) and racemic 2,2'-bis(diphenylphosphino)-1,1'-binaphthyl (BINAP; 21 mg, 0.033 mmol; Strem) in toluene (1 mL) and heating the mixture to 90° C. for 15 min. The solution was cooled, and then added to a mixture of 1,4-diazabicyclo[3.2.2]nonane (105 mg, 0.83 mmol; see *J. Med. Chem.* 1993, 36, 2311) and 3,7-dibromodibenzothiophene-5,5-dioxide (0.60 g, 1.60 mmol; see *J. Med. Chem.* 1978, 21, 1084), in toluene (3 mL). Cs$_2$CO$_3$ (1.04 g, 3.2 mmol; Aldrich) was then added, and the reaction mixture was flushed with nitrogen and heated to 80-85° C. overnight. After cooling to room temperature, the mixture was filtered through diatomaceous earth and purified by chromatography (35 g silica gel, 1-10% gradient of NH$_4$OH-MeOH (1:10) in CH$_2$Cl$_2$) to afford the title compound (102 mg, 0.30 mmol, 36% yield): MS (DCI/NH$_3$) m/z 341 (M+H)$^+$.

Example 51B 4-(5,5-Dioxo-5H-5λ$^6$-dibenzothiophen-3-yl)-1,4-diazabicyclo[3.2.2]nonane p-toluenesulfonate A mixture of the product of Example 51A (102 mg, 0.30 mmol) and p-toluenesulfonic acid monohydrate (67 mg, 0.35 mmol) was stirred in EtOAc-EtOH (2 mL, 10:1) at room temperature for 2 h. The resulting solid was collected and dried under vacuum to afford the title compound as a reddish solid (117 mg, 0.228 mmol, 76% yield): $^1$H NMR (300 MHz, CD$_3$OD) δ ppm 2.11-2.28 (m, 2H), 2.32-2.47 (m, 5H), 3.50-3.65 (m, 6H), 3.96 (t, J=6 Hz, 2H), 4.41-4.52 (m, 1H), 7.23 (d, J=8 Hz, 3H), 7.33 (d, J=3 Hz, 1H), 7.47 (t, J=8 Hz, 1H), 7.63-7.79 (m, 4H), 7.85 (d, J=8 Hz, 2H); MS (DCI/NH$_3$) m/z 341 (M+H)$^+$; Anal. C$_{19}$H$_{20}$N$_2$O$_2$S.C$_7$H$_8$O$_3$S.0.6H$_2$O: C, H, N.

Example 52

(S)-2-(1-Azabicyclo[2.2.2]oct-3-yloxy)-xanthen-9-one trifluoroacetate

Example 52A

2-Iodoxanthen-9-one

A solution of xanthen-9-one (1.96 g, 10.0 mmol; Aldrich) in trifluoroacetic acid-CH$_2$Cl$_2$ (1:1, 40 mL) was chilled to 0° C. and treated with N-iodosuccinimide (NIS; 2.25 g, 10.0 mmol; Lancaster), added portionwise over 1 h. After an additional 1 h at 0° C., the ice bath was removed and stirring continued for 8 h. Residual oxidant was quenched with aq. NaS$_2$O$_3$ and the mixture was extracted with CH$_2$Cl$_2$. The organic phase was washed with NaHCO$_3$, dried over MgSO$_4$, and the residue purified by flash chromatography (120 g silica gel, 10-100% CH$_2$Cl$_2$-hexanes) to afford the title compound (1.75 g, 5.43 mmol; 54% yield): $^1$H NMR (300 MHz, CDCl$_3$) δ ppm 8.66 (d, J=2 Hz, 1H), 8.34 (dd, J=8, 2 Hz, 1H), 7.98 (dd, J=9, 2 Hz, 1H), 7.75 (ddd, J=9, 7, 2 Hz, 1H), 7.50 (dd, J=8, 1 Hz, 1H), 7.40 (ddd, J=8, 7, 1 Hz, 1H), 7.28 (d, J=9 Hz, 1H); MS (DCI/NH$_3$) m/z 323 (M+H)$^+$, 340 (M+NH$_4$)$^+$.

Example 52B (S)-2-(1-Azabicyclo[2.2.2]oct-3-yloxy)-xanthen-9-one

A mixture containing the product from Example 52A (160 mg, 0.50 mmol), (S)-quinuclidinyl (65 mg, 0.51 mmol), copper (I) iodide (9 mg, 0.05 mmol; Aldrich), 1,10-phenanthroline (18 mg, 0.1 mmol; Aldrich) and powdered cesium carbonate (250 mg, 0.767 mmol; Aldrich) in dry toluene (0.5 mL) in a sealed vial under nitrogen was heated to 110° C. with vigorous stirring for 36 h. After cooling to room temperature, the reaction mixture was filtered through diatomaceous earth, rinsing with CH$_2$Cl$_2$, concentrated and purified by flash chromatography (35 g silica gel, 1-10% gradient of NH$_4$OH-MeOH (1:10) in CH$_2$Cl$_2$) to provide the crude product (68 mg). This material was purified further by reverse-phase HPLC (40×100 mm Symmetry-C$_8$ column, 5-30% aq. TFA (0.1%)-MeCN). Fractions containing the desired product were combined, adjusted to pH 10 with Na$_2$CO$_3$, and extracted with CH$_2$Cl$_2$ to afford the title compound (53 mg, 0.17 mmol; 34% yield): $^1$H NMR (300 MHz, CDCl$_3$) δ ppm 8.35 (dd, J=8, 2 Hz, 1H), 7.73 (ddd, J=9, 7, 2 Hz, 1H), 7.64 (d, J=3 Hz, 1H), 7.43-7.53 (m, 2H), 7.30-7.42 (m, 2H), 4.55-4.64 (m, 1H), 3.44 (ddd, J=14, 8, 2 Hz, 1H), 2.88-3.15 (m, 5H), 2.26-2.34 (m, 1H), 1.98-2.13 (m, 1H), 1.61-1.91 (m, 2H), 1.41-1.56 (m, 1H); MS (DCI/NH$_3$): m/z 322 (M+1)$^+$.

Example 52C (S)-2-(1-Azabicyclo[2.2.2]oct-3-yloxy)-xanthen-9-one trifluoroacetate The product from Example 52B (53 mg, 0.17 mmol) was dissolved in methanol (500 µL) and treated with trifluoroacetic acid (2 drops). The mixture was diluted with ether (5 mL) and stirred at room temperature for 1 h. The resulting precipitate was collected by centrifugation and washed with ether, affording the title compound (45 mg, 0.10 mmol; 62% yield): $^1$H NMR (300 MHz, CD$_3$OD) δ ppm 8.29 (dd, J=8, 2 Hz, 1H), 7.85 (ddd, J=9, 7, 2 Hz, 1H), 7.72 (d, J=3 Hz, 1H), 7.59-7.67 (m, 2H), 7.54 (dd, J=9, 3 Hz, 1H), 7.47 (ddd, J=8, 7, 1 Hz, 1H), 4.99-5.07 (m, 1H), 3.90 (ddd, J=14, 8, 2 Hz, 1H), 3.32-3.49 (m, 5H), 2.55-2.63 (m, 1H), 2.28-2.41 (m, 1H), 1.85-2.23 (m, 3H); MS (DCI/NH$_3$): m/z 322 (M+1)$^+$; Anal. C$_{20}$H$_{19}$NO$_3$.C$_2$HF$_3$O$_2$.0.1H$_2$O: C, H, N.

Example 53

2-(3,7-Diazabicyclo[3.3.0]oct-3-yl)-xanthen-9-one trifluoroacetate

Example 53A 2-(7-Boc-3,7-diazabicyclo[3.3.0]oct-3-yl)-xanthen-9-one

A mixture of 3-Boc-3,7-diazabicyclo[3.3.0]octane (235 mg, 1.11 mmol; see WO 0181347), 2-iodoxanthen-9-one (362 mg, 1.12 mmol; see Example 52A), tris(dibenzylideneacetone)dipalladium (0) (Pd$_2$(dba)$_3$; 22 mg, 0.024 mmol; Alfa), racemic-2,2'-bis(diphenylphosphino)-1,1'-binaphthyl (BINAP; 37 mg, 0.059 mmol; Strem) and sodium tert-butoxide (166 mg, 1.73 mmol; Acros) in toluene (5 mL) was flushed with nitrogen and warmed to 85° C. with vigorous stirring for 6 h. The reaction mixture was cooled to ambient temperature, filtered through diatomaceous earth with an EtOAc rinse, concentrated under reduced pressure, and purified by flash chromatography (35 g silica gel, 5-50% gradient of EtOAc in hexanes) to afford the title compound as a yellow foam (275 mg, 0.677 mmol; 61% yield): $^1$H NMR (300 MHz, CDCl$_3$) δ ppm 8.35 (dd, J=8, 2 Hz, 1H), 7.69 (ddd, J=9, 7, 2 Hz, 1H), 7.47 (d, J=8 Hz, 1H), 7.43 (d, J=9 Hz, 1H), 7.30-7.38 (m, 2H), 7.05 (dd, J=9, 3 Hz, 1H), 3.57-3.73 (m, 4H), 3.24-3.45 (m, 4H), 2.97-3.12 (m, 2H), 1.46 (s, 9H); MS (DCI/NH$_3$): m/z 407 (M+1)$^+$.

Example 53B 2-(3,7-Diazabicyclo[3.3.0]oct-3-yl)-xanthen-9-one

A solution of the product from Example 53A (275 mg, 0.677 mmol) in CH$_2$Cl$_2$ (5 mL) was chilled to 0° C. and treated with trifluoroacetic acid (5 mL). After 15 min, the ice bath was removed and stirring was continued for an additional 1 h. The solution was concentrated under vacuum and the residue was purified by flash chromatography (35 g silica gel, 1-10% gradient of NH$_4$OH-MeOH (1:10) in CH$_2$Cl$_2$) to provide the title compound (97 mg, 0.32 mmol; 47% yield): $^1$H NMR (300 MHz, CDCl$_3$) δ ppm 8.35 (dd, J=8, 2 Hz, 1H), 7.69 (ddd, J=9, 7, 2 Hz, 1H), 7.47 (dd, J=8, 1 Hz, 1H), 7.38-7.44 (m, 2H), 7.34 (td, J=7, 1 Hz, 1H), 7.14 (dd, J=9, 3 Hz, 1H), 3.44-3.53 (m, 2H), 3.27 (dd, J=9, 3 Hz, 2H), 3.12-3.21 (m, 2H), 2.96 (td, J=7, 3 Hz, 2H), 2.87 (dd, J=11, 3 Hz, 2H); MS (DCI/NH$_3$): m/z 307 (M+1)$^+$.

Example 53C 2-(3,7-Diazabicyclo[3.3.0]oct-3-yl)-xanthen-9-one trifluoroacetate A suspension of the product from Example 53B (92 mg, 0.30 mmol) in methanol (1 mL) was treated with trifluoroacetic acid (2 drops), diluted with ether (20 mL) and stirred at room temperature for 8 h. The resulting precipitate was collected by filtration to afford the title compound (104 mg, 0.247 mmol; 82% yield): $^1$H NMR (300 MHz, CD$_3$OD) δ ppm 8.27 (dd, J=8, 2 Hz, 1H), 7.81 (ddd, J=9, 7, 2 Hz, 1H), 7.53-7.61 (m, 2H), 7.36-7.46 (m, 3H), 3.55-3.65 (m, 4H), 3.24-3.43 (m, 6H); MS (DCI/NH$_3$): m/z 307 (M+1)$^+$; Anal. C$_{19}$H$_{18}$N$_2$O$_2$.C$_2$HF$_3$O$_2$: C, H, N.

Example 54

2-(7-Methyl-3,7-diazabicyclo[3.3.0]oct-3-yl)-xanthen-9-one trifluoroacetate

Example 54A

5-Benzyl-2-methyl-tetrahydropyrrolo[3,4-c]pyrrole-1,3-dione

N-Methylmaleimide (23.3 g, 21 mmol; Aldrich) was dissolved in CH$_2$Cl$_2$ (400 mL) in a 3-neck flask, chilled to 0° C. under nitrogen, and treated with trifluoroacetic acid (1.6 mL, 21 mmol; Aldrich). A solution of N-(methoxymethyl)-N-(trimethylsilylmethyl)-benzylamine (49.8 g, 21 mmol; Aldrich) in CH$_2$Cl$_2$ (60 mL) was then added slowly at a rate to maintain the temperature below about 5° C. After the addition was complete, the ice bath was removed and the reaction mixture was stirred for 24 h. The solution was concentrated under vacuum, and the residue was diluted with CH$_2$Cl$_2$ (125 mL), washed with saturated aqueous NaHCO$_3$ (2×100 mL) and brine (2×100 mL). The organic phase was concentrated under vacuum to afford the title compound as a white solid (51.2 g, 21 mmol; 100% yield): $^1$H NMR (300 MHz, CDCl$_3$) δ ppm 7.14-7.37 (m, 5H), 3.57 (s, 2H), 3.28 (d, J=10.2 Hz, 2H), 3.13-3.21 (m, 2H), 3.01 (s, 3H), 2.32-2.42 (m, 2H); MS (DCI/NH$_3$) m/z 245 (M+H)$^+$.

Example 54B

2-Benzyl-5-methyl-octahydropyrrolo[3,4-c]pyrrole

A solution of the product of Example 54A (28 g, 115 mmol) in anhydrous THF (120 mL) was added dropwise over 3 h to a 0° C. solution of LiAlH$_4$ in THF (1 M, 350 mL, 350 mmol; Aldrich) under nitrogen. The mixture was warmed to room temperature, stirred for 30 min, and then heated to reflux for 3 h. After cooling again to 0° C., the reaction was quenched by careful addition of Na$_2$SO$_4$.10H$_2$O (Aldrich). The slurry was stirred overnight, filtered through diatomaceous earth, concentrated under vacuum, and the residue purified by flash chromatography (silica gel, 10% MeOH—CH$_2$Cl$_2$) to provide the title compound (10.2 g, 47 mmol; 41% yield): $^1$H NMR (300 MHz, CDCl$_3$) δ ppm 7.19-7.36 (m, 5H), 3.59 (s, 2H), 2.65-2.78 (m, 4H), 2.50-2.58 (m, 2H), 2.39 (dd, J=9.0, 2.9 Hz, 2H), 2.26-2.35 (m, 5H); MS (DCI/NH$_3$) m/z 217 (M+H)$^+$.

Example 54C

2-Methyl-octahydropyrrolo[3,4-c]pyrrole

The product of Example 54B (10.2 g, 47 mmol) was dissolved in methanol (150 mL) and treated with 10% Pd/C (200 mg; Aldrich) at 50° C. under a hydrogen balloon atmosphere for 16 h. After the catalyst was removed by filtration, and the filtrate was concentrated under vacuum and the residue was purified by flash chromatography (silica gel, 10% MeOH—CH$_2$Cl$_2$) to afford the title compound (5.2 g, 41.2 mmol; 88% yield): $^1$H NMR (300 MHz, CDCl$_3$) δ ppm 2.85-2.98 (m, 2H), 2.53-2.79 (m, 6H), 2.25-2.34 (m, 5H); MS (DCI/NH$_3$) m/z 127 (M+H)$^+$.

Example 54D 2-(7-Methyl-3,7-diazabicyclo[3.3.0]oct-3-yl)-xanthen-9-one

A mixture of the product of Example 54C (100 mg, 0.794 mmol), 2-iodoxanthen-9-one (300 mg, 0.932 mmol; see Example 52A), tris(dibenzylideneacetone)dipalladium (0) (Pd$_2$(dba)$_3$; 16 mg, 0.017 mmol; Aldrich), racemic-2,2'-bis (diphenylphosphino)-1,1'-binaphthyl (BINAP; 26 mg, 0.059 mmol; Aldrich) and sodium tert-butoxide (110 mg, 1.14 mmol; Acros) in toluene (3 mL) was flushed with nitrogen and warmed to 90° C. with vigorous stirring for 16 h. The reaction mixture was cooled to ambient temperature, filtered through diatomaceous earth with a CH$_2$Cl$_2$ rinse, concentrated under reduced pressure, and purified by flash chromatography (35 g silica gel, 1-10% gradient of NH$_4$OH-MeOH (1:10) in CH$_2$Cl$_2$) to provide the title compound (106 mg, 0.331 mmol; 42% yield): $^1$H NMR (300 MHz, CDCl$_3$) δ ppm 8.35 (dd, J=8, 2 Hz, 1H), 7.69 (ddd, J=9, 7, 2 Hz, 1H), 7.46 (dd, J=8, 1 Hz, 1H), 7.43 (d, J=3 Hz, 1H), 7.41 (d, J=9 Hz, 1H), 7.34 (ddd, J=8, 7, 1 Hz, 1H), 7.15 (dd, J=9, 3 Hz, 1H), 3.43-3.52 (m, 2H), 3.32 (dd, J=10, 3 Hz, 2H), 2.97-3.11 (m, 2H), 2.75-2.88 (m, 2H), 2.51 (dd, J=9, 4 Hz, 2H), 2.34-2.41 (m, 3H); MS (DCI/NH$_3$): m/z 321 (M+1)$^+$.

Example 54E 2-(7-Methyl-3,7-diazabicyclo[3.3.0]oct-3-yl)-xanthen-9-one trifluoroacetate A solution of the product from Example 54D (105 mg, 0.328 mmol) in methanol (0.5 mL) was treated with trifluoroacetic acid (2 drops), diluted with ether (5 mL) and stirred at room temperature for 2 h. The resulting precipitate was collected by filtration to afford the title compound (117 mg, 0.256 mmol; 78% yield): $^1$H NMR (300 MHz, CD$_3$OD) δ ppm 8.27 (dd, J=8, 2 Hz, 1H), 7.82 (ddd, J=8, 7, 2 Hz, 1H), 7.40-7.61 (m, 5H), 3.59-3.74 (m, 4H), 3.21-3.51 (m, 6H), 2.95 (s, 3H); MS (DCI/NH$_3$): m/z 321 (M+1)$^+$; Anal. C$_{20}$H$_{20}$N$_2$O$_2$.1.2C$_2$HF$_3$O$_2$: C, H, N.

Example 56

2-(2-Diethylaminoethoxy)-7-(3-diethylaminoprop-1-ynyl)-fluoren-9-one dihydrochloride Example 56A 2-(2-Diethylaminoethoxy)-7-iodo-fluoren-9-one A mixture of 2,7-diiodofluoren-9-one (4.32 g, 10.0 mmol; see J. Chem. Res. (S) 1999, 590), 2-diethylaminoethanol (1.35 mL, 10.2 mmol; Aldrich), copper (I) iodide (190 mg, 1.0 mmol; Aldrich), 1,10-phenanthroline (360 mg, 2.0 mmol; Aldrich) and powdered cesium carbonate (6.5 g, 20 mmol; Aldrich) in dry toluene (10 mL) was heated under nitrogen to 110° C. with vigorous stirring for 24 h. After cooling to room temperature, the reaction mixture was filtered through diatomaceous earth, rinsing with CH$_2$Cl$_2$, and concentrated. The residue was dissolved in CH$_2$Cl$_2$, washed with aq. NaOH, and purified by flash chromatography (120 g silica gel, 1-10% gradient of NH$_4$OH-MeOH (1:10) in CH$_2$Cl$_2$) to provide the title compound (1.85 g, 4.39 mmol; 44% yield): $^1$H NMR (300 MHz, CDCl$_3$) δ 7.90 (d, J=2 Hz, 1H), 7.76 (dd, J=8, 2 Hz, 1H), 7.39 (d, J=8 Hz, 1H), 7.14-7.22 (m, 2H), 7.00 (dd, J=8, 2 Hz, 1H), 4.11 (br s, 2H), 2.52-3.05 (m, 6H), 1.10 (t, J=7 Hz, 6H); MS (DCI/NH$_3$): m/z 422 (M+1)$^+$.

Example 56B

2-(2-Diethylaminoethoxy)-7-(3-diethylaminoprop-1-ynyl)-fluoren-9-one

The product from Example 56A (221 mg, 0.525 mmol) was mixed with 3-diethylamino-1-propyne (150 μL, 1.09 mmol; Lancaster), triethylamine (200 μL, 1.44 mmol; Acros), dichlorobis(triphenylphosphino)palladium (II) (Cl$_2$Pd(PPh$_3$)$_2$; 20 mg, 0.028 mmol; Aldrich), and copper (I) iodide (24 mg, 0.13 mmol; Aldrich) in DMF (5 mL) was heated to 65° C. for 18 h. The reaction mixture was diluted with EtOAc, washed with water and brine, and dried over MgSO$_4$. The residue was purified by flash chromatography (40 g silica gel, 1-12% gradient of NH$_4$OH-MeOH (1:10) in CH$_2$Cl$_2$) to afford the crude product. This material was purified further by reverse-phase HPLC (30×100 mm XTerra RP$_8$ column, aq. TFA (0.1%)-MeCN gradient). Fractions containing the desired product were combined, adjusted to ~pH 10 with Na$_2$CO$_3$, and extracted with CH$_2$Cl$_2$ to afford the title compound (97 mg, 0.24 mmol; 46% yield): $^1$H NMR (300 MHz, CDCl$_3$) δ ppm 7.63 (d, J=1 Hz, 1H), 7.48 (dd, J=8, 1 Hz, 1H), 7.39 (d, J=8 Hz, 1H), 7.33 (d, J=7 Hz, 1H), 7.20 (d, J=2 Hz, 1H), 7.00 (dd, J=8, 2 Hz, 1H), 4.11 (t, J=6 Hz, 2H), 3.66 (s, 2H), 2.91 (t, J=6 Hz, 2H), 2.68 (q, J=7 Hz, 4H), 2.63 (q, J=7 Hz, 4H), 1.13 (t, J=7 Hz, 6H), 1.09 (t, J=7 Hz, 6H); MS (DCI/NH$_3$): m/z 405 (M+1)$^+$.

Example 57

2-Bromo-7-[(1R,5R)-6-methyl-3,6-diazabicyclo[3.2.0]hept-3-yl]-fluoren-9-one p-toluenesulfonate

Example 57A

3-(7-Bromo-9-oxo-9H-fluoren-2-yl)-(1R,5R)-3,6-diazabicyclo[3.2.0]heptane-6-carboxylic acid tert-butyl ester A mixture of 3,6-diazabicyclo[3.2.0]heptane-6-carboxylic acid tert-butyl ester (600 mg, 3.0 mmol; prepared according to patent WO2001081347), 2,7-dibromo-fluoren-9-one (1.3 g, 4 mmol; Aldrich), sodium tert-butoxide (400 mg, 4.2 mmol; Aldrich), tris(dibenzylideneacetone)dipalladium (Pd$_2$(dba)$_3$; 160 mg, 0.17 mmol; Alfa) and racemic 2,2'-bis(diphenylphosphino)-1,1'-binaphthyl (BINAP; 330 mg, 0.53 mmol; Strem) in dry toluene (30 mL) was warmed to 85° C. and stirred under nitrogen atmosphere for 3 h. The reaction mixture was concentrated under vacuum and purified by flash chromatography (80 g silica gel, 40:60 hexanes-EtOAc) to afford the title compound (800 mg, 1.76 mmol; 55% yield): $^1$H NMR (300 MHz, CD$_3$OD) δ ppm 7.56-7.61 (2H, m), 7.47 (1H, d, J=8 Hz), 7.38 (1H, d, J=8 Hz), 7.06 (1H, d, J=3 Hz), 6.92 (1H, dd, J=8, 3 Hz), 4.60-4.67 (1H, m), 3.91-4.16 (2H, m), 3.73-3.86 (1H, m), 3.55-3.66 (1H, m), 3.41-3.51 (1H, m), 2.90-3.27 (3H, m), 1.36-1.55 (9H, s); MS (DCI/NH$_3$): m/z 455 (M+1)$^+$, 457 (M+3)$^+$.

Example 57B

2-Bromo-7-[(1R,5R)-6-methyl-3,6-diazabicyclo[3.2.0]hept-3-yl]-fluoren-9-one The product of Example 57A (800 mg, 1.76 mmol) was treated with trifluoroacetic acid (1.5 mL) in CH$_2$Cl$_2$ (5 mL) at room temperature for 1 h. The mixture was concentrated and the residue was treated with aqueous formaldehyde (37%, 1 mL) and sodium triacetoxyborohydride (422 mg, 2.00 mmol; Aldrich) in water (5 mL). After 16 h, the reaction mixture was concentrated under vacuum and purified by flash chromatography (80 g silica gel, 1:10:89 NH$_4$OH-MeOH—CH$_2$Cl$_2$) to afford the title compound (400 mg, 1.08 mmol; 62% yield): $^1$H NMR (300 MHz, CD$_3$OD) δ 7.55-7.60 (2H, m), 7.46 (1H, d, J=8 Hz), 7.37 (1H, d, J=8 Hz), 7.02 (1H, d, J=3 Hz), 6.86 (1H, dd, J=8, 2 Hz), 3.98-4.05 (1H, m), 3.71-3.82 (2H, m), 3.00-3.40 (5H, m), 2.39 (3H, s); MS (DCI/NH$_3$): m/z 369 (M+1)$^+$, 371 (M+3)$^+$.

Example 57C

2-Bromo-7-[(1R,5R)-6-methyl-3,6-diazabicyclo[3.2.0]hept-3-yl]-fluoren-9-one p-toluenesulfonate A mixture of the product of Example 57B (80 mg, 0.22 mmol) and p-toluenesulfonic acid monohydrate (48 mg, 0.25 mmol) was stirred in EtOAc-EtOH (4 mL, 10:1) at room temperature for 16 h. The resulting solid was collected and dried to afford the title compound (56 mg, 0.10 mmol; 47% yield): $^1$H NMR (500 MHz, DMSO-d$_6$) δ ppm 7.57-7.75 (4H, m), 7.47 (2H, d, J=8 Hz), 6.97-7.14 (4H, m), 4.80-5.04 (1H, m), 3.81-4.49 (4H, m), 3.36-3.54 (1H, m), 3.01-3.17 (2H, m), 2.61-2.95 (3H, m), 2.28 (3H, s); MS (DCI/NH$_3$): m/z 369 (M+1)$^+$, 371 (M+3)$^+$. Anal. Calcd. for C$_{19}$H$_{17}$BrN$_2$O.C$_7$H$_8$O$_3$S: C, 57.67; H, 4.65; N, 5.17. Found: C, 57.66; H, 4.85; N, 4.95.

Example 58

2-(1-Azabicyclo[2.2.2]oct-3-yloxy)-7-bromo-fluoren-9-one trifluoroacetate

Example 58A

2-Bromo-7-iodo-fluoren-9-one

A suspension of 2-iodofluoren-9-one (1.046 g, 3.42 mmol; Maybridge) and iodobenzene diacetate (1.21 g, 3.76 mmol; Aldrich) in 1:1 Ac$_2$O—HOAc (10 mL) was treated with bromine (180 μL, 3.48 mmol; Aldrich) followed by 3 drops concentrated sulfuric acid. The mixture solidified, so it was diluted with acetic acid until it could be stirred. After 2 h, the reaction was quenched with aq. Na$_2$S$_2$O$_3$, neutralized with K$_2$CO$_3$, and filtered. The solid filter cake was washed with water, dried, and recrystallized from hot EtOH to afford the title compound (1.05 g, 2.73 mmol; 80% yield): $^1$H NMR (300 MHz, CDCl$_3$) δ ppm 7.97 (dd, J=2, 1 Hz, 1H), 7.84 (dd, J=8, 2 Hz, 1H), 7.75-7.79 (m, 1H), 7.63 (dd, J=8, 2 Hz, 1H), 7.39 (d, J=7 Hz, 1H), 7.24-7.31 (m, 1H); MS (DCI/NH$_3$): m/z 384 (M+1)$^+$, 386 (M+3)$^+$.

Example 58B

2-(1-Azabicyclo[2.2.2]oct-3-yloxy)-7-bromo-fluoren-9-one trifluoroacetate

A mixture containing 3-quinuclidinyl (695 mg, 5.47 mmol; Aldrich), 2-bromo-7-iodofluoren-9-one (1.05 g, 2.73 mmol;

see Example 58A), copper (I) iodide (50 mg, 0.26 mmol; Aldrich), 1,10-phenanthroline (100 mg, 0.56 mmol; Aldrich) and powdered cesium carbonate (1.25 g, 3.83 mmol; Aldrich) in anhydrous toluene (10 mL) was heated to 110° C. under nitrogen in a sealed tube for 20 h. After cooling to room temperature, the reaction mixture was filtered through diatomaceous earth, rinsing with $CH_2Cl_2$, concentrated and purified by flash chromatography (80 g silica gel, 0-10% gradient of $NH_4OH$-MeOH (1:10) in $CH_2Cl_2$). The crude free base was purified further by reverse-phase HPLC (40×100 mm Symmetry-$C_8$ column, aq. TFA (0.2%)-MeCN gradient). Fractions containing the desired compound were combined and concentrated under vacuum. The oily residue was stirred with EtOAc for 4 h, and the resulting solid collected by filtration to afford the title compound (110 mg, 0.221 mmol; 8% yield): $^1$H NMR (300 MHz, $CD_3OD$) δ ppm 7.65-7.70 (m, 2H), 7.63 (d, J=8 Hz, 1H), 7.51 (d, J=8 Hz, 1H), 7.24 (d, J=2 Hz, 1H), 7.17 (dd, J=8, 2 Hz, 1H), 4.93-5.01 (m, 1H), 3.83 (ddd, J=14, 8, 2 Hz, 1H), 3.25-3.47 (m, 5H), 2.54 (td, J=7, 4 Hz, 1H), 2.23-2.37 (m, 1H), 1.83-2.20 (m, 3H); MS (DCI/$NH_3$): m/z 384 (M+1)$^+$, 386 (M+3)$^+$; Anal. $C_{20}H_{18}BrNO_2 \cdot C_2HF_3O_2$: C, H, N.

Example 59

2-(1-Methylpiperidin-4-yloxy)-7-(piperidin-4-yloxy)-fluoren-9-one dihydrochloride To a solution of 2-(1-methylpiperidin-4-yloxy)-7-(piperidin-4-yloxy)-fluoren-9-one (81 mg, 0.21 mmol; Example 24A) in EtOAc (10 mL) containing a few drops of ethanol was added a solution of HCl in dioxane (4 M, 335 μL, 1.34 mmol; Aldrich). After stirring the mixture for 2 h, the solid was collected by filtration and recrystallized from hot EtOH-EtOAc to afford the title compound (50 mg, 0.11 mmol, 51% yield): $^1$H NMR (300 MHz, $CD_3OD$) δ ppm 1.97-2.11 (m, 3H), 2.11-2.27 (m, 4H), 2.92 (s, 3H), 3.18-3.30 (m, 4H), 3.35-3.47 (m, 4H), 4.72-4.81 (m, 2H), 7.14 (dd, J=8, 2 Hz, 2H), 7.22 (d, J=2 Hz, 2H), 7.50 (d, J=8 Hz, 2H); MS (DCI/$NH_3$) m/z 393 (M+H)$^+$; Anal. $C_{24}H_{28}N_2O_3 \cdot 2HCl$: C, H, N.

Example 60

2-(Hexahydropyrrolo[3,4-c]pyrrol-2-yl)-7-hydroxy-fluoren-9-one hydrochloride

Example 60A 5-(7-tert-Butoxy-9-oxo-9H-fluoren-2-yl)-hexahydro-pyrrolo[3,4-c]pyrrole-2-carboxylic acid tert-butyl ester A mixture of the product of Example 20A (505 mg, 1.08 mmol), tris(dibenzylideneacetone)dipalladium ($Pd_2(dba)_3$; 20 mg, 0.022 mmol; Alfa), 2-(di-t-butylphosphino)-biphenyl (16 mg, 0.054 mmol; Strem), and sodium tert-butoxide (130 mg, 1.35 mmol; Aldrich) in anhydrous toluene (2 mL) was heated to 110° C. under nitrogen for 24 h. The reaction mixture was cooled to room temperature, filtered through diatomaceous earth with $CH_2Cl_2$ and MeOH rinses, and purified by flash chromatography (80 silica gel, 10-80% gradient of EtOAc in hexanes) to afford the title compound (100 mg, 0.20 mmol; 20% yield): $^1$H NMR (300 MHz, $CDCl_3$) δ ppm 7.21 (d, J=8 Hz, 1H), 7.18 (d, J=8 Hz, 1H), 7.02 (d, J=2 Hz, 1H), 6.80-6.88 (m, 2H), 6.52 (dd, J=8, 3 Hz, 1H), 3.20-3.72 (m, 8H), 2.93-3.08 (m, 2H), 1.54 (s, 9H), 1.46 (s, 9H); MS (DCI/$NH_3$): m/z 407 (M-55)$^+$.

Example 60B 2-(Hexahydropyrrolo[3,4-c]pyrrol-2-yl)-7-hydroxy-fluoren-9-one hydrochloride A solution of the product of Example 60A (100 mg, 0.20 mmol) in $CH_2CH_2$ (5 mL) was chilled to 0° C. and treated with trifluoroacetic acid (5 mL). The ice bath was removed and the solution was stirred for 1 h. After evaporation of the volatiles, the residue was purified by reverse-phase HPLC (40×100 mm Symmetry $C_8$ column, aq. TFA (0.2%)-MeCN gradient). Fractions containing the desired product were combined, adjusted to ~pH 10 with $Na_2CO_3$, and extracted with $CH_2Cl_2$ and $CHCl_3$. This material (25 mg, 0.082 mmol) was suspended in EtOAc-EtOH-MeOH and treated with HCl-dioxane (4 M, 18 μL, 0.072 mmol; Aldrich). The resulting solid was collected by centrifugation to afford the title compound (20 mg, 0.058 mmol; 29% yield): $^1$H NMR (300 MHz, $CD_3OD$) δ ppm 7.30 (d, J=8 Hz, 1H), 7.25 (d, J=8 Hz, 1H), 6.94 (dd, J=9, 2 Hz, 2H), 6.84 (dd, J=8, 2 Hz, 1H), 6.78 (dd, J=8, 3 Hz, 1H), 3.53-3.63 (m, 2H), 3.49 (dd, J=10, 2 Hz, 4H), 3.17-3.40 (m, 6H); MS (DCI/$NH_3$): m/z 307 (M+1)$^+$; Anal. $C_{19}H_{18}N_2O_2 \cdot HCl$: C, H, N.

Example 61

2-Amino-7-(5-methylhexahydropyrrolo[3,4-c]pyrrol-2-yl)-fluoren-9-one dihydrochloride Example 61A 2-Bromo-7-(5-methylhexahydropyrrolo[3,4-c]pyrrol-2-yl)-fluoren-9-one A mixture of 3-methyl-3,7-diazabicyclo[3.3.0]octane (297 mg, 2.36 mmol; see Example 54C), 2,7-dibromofluoren-9-one (680 g, 2.01 mmol; Aldrich), tris(dibenzylideneacetone)dipalladium (0) ($Pd_2$ $dba_3$; 37 mg, 0.040 mmol; Alfa), racemic-2,2'-bis(diphenylphosphino)-1,1'-binaphthyl (BINAP; 63 mg, 0.10 mmol; Strem) and sodium tert-butoxide (270 mg, 2.81 mmol; Acros) in 10 mL toluene was warmed to 90° C. and stirred for 16 h. The reaction mixture was cooled to ambient temperature and filtered through Celite, rinsing with $CH_2Cl_2$. After concentrating the solution under reduced pressure, the residue was purified by flash chromatography (120 g silica gel, 1-20% gradient of $NH_4OH$-MeOH (1:10) in $CH_2Cl_2$) to give the crude product. This material was purified further by flash chromatography (40 g Analogix $NH_2$ column, 10-100% EtOAc in hexanes) to afford the title compound as a reddish solid (335 mg, 0.875 mmol; 44% yield): $^1$H NMR (300 MHz, $CDCl_3$) δ ppm 7.64 (d, J=2 Hz, 1H), 7.49 (dd, J=8, 2 Hz, 1H), 7.29 (d, J=8 Hz, 1H), 7.19 (d, J=8 Hz, 1H), 6.95 (d, J=2 Hz, 1H), 6.64 (dd, J=8, 2 Hz, 1H), 3.42-3.53 (m, 2H), 3.29 (dd, J=10, 3 Hz, 2H), 2.99-3.13 (m, 2H), 2.75-2.94 (m, 2H), 2.56 (dd, J=9, 3 Hz, 2H), 2.41 (s, 3H); MS (ESI): m/z 383 (M+1)$^+$, 385 (M+3)$^+$.

Example 61B 2-(Benzhydrylideneamino)-7-(5-methylhexahydro-pyrrolo[3,4-c]pyrrol-2-yl)-fluoren-9-one A mixture of the product of Example 61A (332 mg, 0.867 mmol), benzophenone imine (180 μL, 1.07 mmol; Aldrich), tris(dibenzylideneacetone)dipalladium (0) ($Pd_2$ $dba_3$; 32 mg, 0.035 mmol; Alfa), racemic-2,2'-bis(diphenylphosphino)-1,1'-binaphthyl (BINAP; 54 mg, 0.087 mmol; Strem) and sodium tert-butoxide (125 mg, 1.30 mmol; Aldrich) in 5 mL toluene was flushed with nitrogen and heated at 90° C. for 18 h. The reaction mixture was cooled to ambient temperature and filtered through diatomaceous earth, rinsing with EtOAc. After concentrating the solution under reduced pressure, the residue was purified by column chromatography (90 g silica gel, 1-12% gradient of $NH_4OH$-MeOH (1:10) in $CH_2Cl_2$) to afford the title compound, which was slightly impure (489 mg, >100% yield): MS ($DCI/NH_3$): m/z 484 (M+1)+.

Example 61C

2-Amino-7-(5-methylhexahydropyrrolo[3,4-c]pyrrol-2-yl)-fluoren-9-one

A solution of the product of Example 61B (489 mg, <0.867 mmol) in THF (5 mL) was treated with 5 drops of 1 N HCl and stirred for 3 h at room temperature. The reaction mixture was diluted with $CH_2Cl_2$, washed with dilute aq. NaOH, and concentrated under vacuum. The resulting material was purified by flash chromatography (35 g silica gel, 1-10% gradient of $NH_4OH$-MeOH (1:10) in $CH_2Cl_2$) to afford the title compound (208 mg, 0.652 mmol; <75% yield): $^1$H NMR (300 MHz, $CDCl_3$) δ 7.17 (d, J=8 Hz, 1H), 7.12 (d, J=8 Hz, 1H), 6.94 (d, J=2 Hz, 1H), 6.91 (d, J=2 Hz, 1H), 6.67 (dd, J=8, 2 Hz, 1H), 6.63 (dd, J=8, 2 Hz, 1H), 3.73 (s, 2H), 3.25-3.42 (m, 4H), 3.04-3.21 (m, 2H), 2.40-2.64 (m, 5H); MS ($DCI/NH_3$): m/z 320 (M+1)+.

Example 61D

2-Amino-7-(5-methylhexahydropyrrolo[3,4-c]pyrrol-2-yl)-fluoren-9-one dihydrochloride A suspension of the product of Example 61C (208 mg, 0.652 mmol) in EtOAc-EtOH (5 mL, 4:1) was chilled to 0° C. and treated with HCl-dioxane (4 M, 350 μL, 1.4 mmol; Aldrich). The ice bath was removed and stirring continued for 2 h. The resulting solid was collected by filtration to afford the title compound (238 mg, 0.565 mmol; 87% yield): MS (DCI/$NH_3$): m/z 320 (M+1)+; Anal. $C_{20}H_{21}N_3O\cdot2HCl\cdot1.6H_2O$: C, H, N.

Example 62

2-Dimethylamino-7-(hexahydropyrrolo[3,4-c]pyrrol-2-yl)-fluoren-9-one dihydrochloride Example 62A 5-(7-Dimethylamino-9-oxo-9H-fluoren-2-yl)-hexahydropyrrolo[3,4-c]pyrrole-2-carboxylic acid tert-butyl ester A solution of the product of Example 20C (252 mg, 0.617 mmol) in 1,2-dichloroethane (5 mL) was chilled to 0° C. and treated with aq. formaldehyde (37% w/w; 5 mL, ~62 mmol; Fisher) followed by sodium triacetoxyborohydride ($NaBH(OAc)_3$; 330 mg, 1.56 mmol; Aldrich). The ice bath was removed and vigorous stirring was continued overnight. The mixture was poured into aq. NaOH (0.1 M), extracted with $CH_2Cl_2$ (3×), and purified by flash chromatography (90 g silica gel, 10-100% gradient of EtOAc in hexanes) to afford the title compound as a blue solid (100 mg, 0.231 mmol; 37%): MS ($DCI/NH_3$): m/z 434 (M+1)+.

Example 62B

2-Dimethylamino-7-(hexahydropyrrolo[3,4-c]pyrrol-2-yl)-fluoren-9-one

A solution of the product of Example 62A (98 mg, 0.23 mmol) in $CH_2Cl_2$ (2 mL) was chilled to 0° C. and treated with trifluoroacetic acid (2 mL). The ice bath was removed and the solution was stirred for 1 h. The reaction mixture was diluted with $CH_2Cl_2$, washed with 0.1 N NaOH, and concentrated under vacuum. The resulting residue was purified by flash chromatography (4 g silica gel, 1-10% gradient of $NH_4OH$-MeOH (1:10) in $CH_2Cl_2$) to afford the title compound (63 mg, 0.19 mmol; 84% yield): MS ($DCI/NH_3$): m/z 334 (M+1)+.

Example 62C

2-Dimethylamino-7-(hexahydropyrrolo[3,4-c]pyrrol-2-yl)-fluoren-9-one dihydrochloride A suspension of the product of Example 62B (63 mg, 0.19 mmol) in EtOAc-EtOH (5 mL, 4:1) was chilled to 0° C. and treated with HCl-dioxane (4 M, 100 μL, 0.4 mmol; Aldrich). The ice bath was removed and stirring continued for 2 h. The resulting solid was collected by filtration and rinsed with EtOAc to afford the title compound (60 mg, 0.15 mmol; 77% yield): $^1$H NMR (500 MHz, pyridine-$d_5$/$D_2O$) δ ppm 7.45 (d, J=8 Hz, 1H), 7.39 (d, J=8 Hz, 1H), 7.21 (d, J=2 Hz, 1H), 7.00 (d, J=2 Hz, 1H), 6.81 (dd, J=8, 2 Hz, 1H), 6.69 (dd, J=8, 2 Hz, 1H), 4.01 (dd, J=12, 8 Hz, 2H), 3.45 (dd, J=12, 5 Hz, 2H), 3.38 (dd, J=10, 2 Hz, 2H), 3.27-3.33 (m, 2H), 3.17-3.25 (m, 2H), 2.84 (s, 6H); MS ($DCI/NH_3$): m/z 334 (M+1)+; Anal. $C_{21}H_{23}N_3O_2\cdot HCl\cdot0.2H_2O$: C, H, N.

Example 63

2-Dimethylamino-7-(5-methylhexahydropyrrolo[3,4-c]pyrrol-2-yl)-fluoren-9-one trihydrochloride Example 63A 2-Dimethylamino-7-(5-methylhexahydropyrrolo[3,4-c]pyrrol-2-yl)-fluoren-9-one The product of Example 61D (131 mg, 0.311 mmol) was dissolved in aq. formaldehyde (37% w/w; 3 mL, ~37 mmol; Fisher), cooled to 0° C., and treated with sodium triacetoxyborohydride ($NaBH(OAc)_3$; 210 mg, 0.991 mmol; Aldrich). The ice bath was removed and vigorous stirring was continued overnight. The mixture was poured into aq. NaOH (0.1 M), extracted with $CH_2Cl_2$ (3×), and purified by flash chromatography (40 g silica gel, 10-100% gradient of $NH_4OH$-MeOH (1:10) in $CH_2Cl_2$) to afford the crude product (128 mg). This material was purified further by reverse-phase HPLC (30×100 mm Symmetry $C_8$ column, aq. TFA (0.1%)-MeCN gradient). Fractions containing the desired product were combined, adjusted to ~pH 10 with NaOH, and extracted with $CH_2Cl_2$ and $CHCl_3$ to afford the title compound as a blue solid (82 mg, 0.24 mmol; 76% yield): $^1$H NMR (300 MHz, $CD_3OD$) δ ppm 7.22 (d, J=8 Hz, 1H), 7.21 (d, J=8 Hz, 1H), 6.96 (d, J=3 Hz, 1H), 6.89 (d, J=2 Hz, 1H), 6.77 (dd, J=8, 3 Hz, 1H), 6.72 (dd, J=8, 2 Hz, 1H), 3.24-3.37 (m, 4H), 2.93-3.07 (m, 8H), 2.89 (dd, J=9, 7 Hz, 2H), 2.43 (dd, J=9, 4 Hz, 2H), 2.34 (s, 3H); MS ($DCI/NH_3$): m/z 348 (M+1)+.

Example 63B

2-Dimethylamino-7-(5-methylhexahydropyrrolo[3,4-c]pyrrol-2-yl)-fluoren-9-one trihydrochloride A suspension of the product of Example 63B (82 mg, 0.24 mmol) in EtOAc-EtOH (5 mL, 4:1) was treated with HCl-dioxane (4 M, 120 μL, 0.48 mmol; Aldrich) and stirred overnight. The resulting solid was collected by filtration to afford the title compound (70 mg, 0.15 mmol; 64% yield): $^1$H NMR (500 MHz, pyridine-$d_5$/$D_2O$) δ ppm 7.47 (d, J=8 Hz, 1H), 7.41 (d, J=8 Hz, 1H), 7.18 (s, 1H), 7.05 (s, 1H), 6.82 (t, J=7 Hz, 2H), 4.05 (dd, J=11, 7 Hz, 2H), 3.32-3.51 (m, 6H), 3.20 (s, 3H), 3.09-3.16 (m, 2H), 2.87 (s, 6H); MS (DCI/NH$_3$): m/z 348 (M+1)$^+$; Anal. $C_{22}H_{25}N_3O$·3HCl: C, H, N.

Example 64

N-[7-(Hexahydropyrrolo[3,4-c]pyrrol-2-yl)-9-oxo-9H-fluoren-2-yl]-acetamide bis(trifluoroacetate)

Example 64A

5-(7-Acetylamino-9-oxo-9H-fluoren-2-yl)-hexahydropyrrolo[3,4-c]pyrrole-2-carboxylic acid tert-butyl ester A mixture of the product from Example 20C (52 mg, 0.12 mmol), acetic acid (7.6 mg, 0.18 mmol; EMD) and i-Pr$_2$NEt (22 μL, 0.13 mmol; Aldrich) in THF (2 mL) was cooled to 0° C. and treated with HATU (49 mg, 0.13 mmol; Acros). The ice bath was removed and stirring was continued overnight. The reaction mixture was diluted with CH$_2$Cl$_2$ (50 mL) and washed with NaOH (aq.) and H$_2$O. The organic layer was dried (MgSO$_4$), concentrated under reduced pressure, and the residue was purified by flash chromatography (silica gel, 95:5:1 CH$_2$Cl$_2$-MeOH—NH$_4$OH) to afford the title compound (57 mg, 0.13 mmol; 99% yield): $^1$H NMR (300 MHz, CD$_3$OD) δ ppm 1.46 (9H, s), 2.12 (3H, s), 2.97-3.14 (3H, m), 3.17-3.43 (2H, m), 3.48-3.75 (5H, m), 6.66 (1H, dd, J=8, 2 Hz), 6.85 (1H, d, J=2 Hz), 7.34 (2H, dd, J=8, 7 Hz), 7.56 (1H, dd, J=8, 2 Hz), 7.71 (1H, d, J=2 Hz); MS (DCI/NH$_3$): m/z 448 (M+H)$^+$.

Example 64B

N-[7-(Hexahydropyrrolo[3,4-c]pyrrol-2-yl)-9-oxo-9H-fluoren-2-yl]-acetamide bis(trifluoroacetate)

The product of Example 64A (57 mg, 0.13 mmol) was dissolved in CH$_2$Cl$_2$ (5 mL), chilled to 0° C., and treated with trifluoroacetic acid (2.5 mL). After 15 min the ice bath was removed and the reaction mixture was stirred at room temperature overnight. Volatiles were removed under reduced pressure. The resulting dark purple oil was triturated with ether and dried to afford the title compound (22 mg, 0.035 mmol; 27% yield): $^1$H NMR (300 MHz, CD$_3$OD) δ ppm 2.13 (3H, s), 3.14-3.46 (6H, m), 3.46-3.75 (4H, m), 6.82 (1H, dd, J=8, 2 Hz), 6.96-7.02 (1H, m), 7.40 (2H, dd, J=8, 6 Hz), 7.58 (1H, dd, J=8, 2 Hz), 7.77 (1H, d, J=2 Hz); MS (DCI/NH$_3$): m/z 348 (M+H)$^+$.

Example 65

{7-(Hexahydropyrrolo[3,4-c]pyrrol-2-yl)-9-oxo-9H-fluoren-2-yl}-carbamic acid methyl ester trifluoroacetate

Example 65A

5-(7-Methoxycarbonylamino-9-oxo-9H-fluoren-2-yl)-hexahydropyrrolo[3,4-c]pyrrole-2-carboxylic acid tert-butyl ester A mixture of the product of Example 20C (56 mg, 0.14 mmol) and pyridine (34 μL, 0.42 mmol) in THF (2 mL) was chilled to 0° C. and treated with methyl chloroformate (13 μL, 0.17 mmol). After 30 min the ice bath was removed and stirring was continued overnight. The reaction mixture was poured into Na$_2$HCO$_3$ (aq.), extracted with CH$_2$Cl$_2$ (3×25 mL), and the combined organic phases were dried over MgSO$_4$. The residue was purified by flash chromatography (silica gel, CH$_2$Cl$_2$-MeOH—NH$_4$OH, 95:5:1) to afford the title compound as a solid (48 mg, 0.10 mmol; 75% yield): $^1$H NMR (300 MHz, CD$_3$OD) δ ppm 1.44 (9H, s), 2.98-3.13 (3H, m), 3.19-3.41 (2H, m), 3.48-3.70 (5H, m), 3.74 (3H, s), 6.66 (1H, dd, J=8, 3 Hz), 6.84 (1H, d, J=2 Hz), 7.32 (2H, t, J=8 Hz), 7.44 (1H, dd, J=7, 2 Hz), 7.61 (1H, d, J=2 Hz); MS (DCI/NH$_3$): m/z 464 (M+H)$^+$.

Example 65B

{7-(Hexahydropyrrolo[3,4-c]pyrrol-2-yl)-9-oxo-9H-fluoren-2-yl}-carbamic acid methyl ester trifluoroacetate The product of Example 65A (48 mg, 0.10 mmol) was dissolved in 5 mL CH$_2$Cl$_2$, chilled to 0° C., and treated with trifluoroacetic acid (TFA; 2.5 mL). After 15 min the ice bath was removed and the reaction mixture was stirred at room temperature overnight. Volatiles were removed under reduced pressure. The resulting dark purple oil was triturated with ether and dried to afford the title compound (36 mg, 0.057 mmol; 55% yield): $^1$H NMR (300 MHz, CD$_3$OD) δ ppm 3.20-3.34 (4H, m), 3.35-3.44 (2H, m), 3.48-3.66 (4H, m), 3.72-3.77 (3H, m), 6.81 (1H, dd, J=8, 2 Hz), 6.98 (1H, d, J=2 Hz), 7.37 (2H, t, J=8 Hz), 7.43-7.50 (1H, m), 7.66 (1H, d, J=2 Hz); MS (DCI/NH$_3$): m/z 364 (M+H)$^+$.

Example 66

6-(Hexahydropyrrolo[3,4-c]pyrrol-2-yl)-9-oxa-1-azaanthracen-10-one hydrochloride

Example 66A

6-Bromo-9-oxa-1-azaanthracen-10-one

Sodium metal (2.30 g, 100 mmol) was added to ice-cooled methanol (75 mL) with stirring under nitrogen. After the sodium had reacted completely, a slurry of 4-bromophenol (8.65 g, 50 mmol) and 2-chloronicotinic acid (7.88 g, 50 mmol) in methanol (50 mL) was added. The resulting light yellow solution was concentrated under vacuum, and the solid residue was taken up in DMF (50 mL) and heated to 130° C. for 18 h. The mixture was cooled, concentrated under vacuum, and the residue was diluted with water (50 mL) and extracted with ether (2×50 mL). The aqueous phase was acidified with 5% sulfuric acid (60 mL) to pH ~3, and the slurry was stirred for 1 h and the precipitate was isolated by filtration and dried at 50° C. The tan solid (3.48 g), a 3:2 mixture of 2-(4-bromophenoxy)nicotinic acid and 2-chloronicotinic acid, was used directly for the cyclization. The solid (1.0 g) was added in one portion to a solution of phosphorous pentoxide (2.6 g) in methanesulfonic acid (27 g) at 80° C. The brownish solution was heated at 80° C. for 15 h, then cooled and poured onto ice (100 g). The mixture was brought to pH>9 by addition of 50% NaOH (17 mL) and extracted with dichloromethane (2×40 mL). The organic extract was dried (MgSO$_4$) and concentrated to provide the title compound as a white solid (0.32 g, 8% from 4-bromophenol). $^1$H NMR (300 MHz, CD$_3$OD) δ ppm 7.59 (dd, J=8, 5 Hz, 1H), 7.64 (d, J=8 Hz, 1H), 8.00 (dd, J=9, 3 Hz, 1H), 8.36 (d, J=2 Hz, 1H), 8.73 (dd, J=8, 2 Hz, 1H), 8.78 ppm (dd, J=5, 2 Hz, 1H); MS (DCI/NH$_3$) m/z 276/278 (M+H)$^+$.

Example 66B 5-(10-Oxo-10H-9-oxa-1-azaanthracen-6-yl)-hexahydropyrrolo[3,4-c]pyrrole-2-carboxylic acid tert-butyl ester 3-Boc-3,7-diazabicyclo[3.3.0]octane (170 mg, 0.73 mmol; see WO 0181347), Pd$_2$dba$_3$ (30 mg, 0.036 mmol; Alfa), racemic-BINAP (41 mg, 0.072 mmol; Strem) and Cs$_2$CO$_3$ (360 mg, 1.1 mmol; Aldrich) were combined with toluene (20 mL). The product of Example 66A (201 mg, 0.73 mmol) was added, and the mixture was evacuated and purged with nitrogen three times. The mixture was heated to 85° C. for 6 h, cooled, and transferred directly to a column of silica gel and eluted with hexanes-EtOAc (50:50 step gradient to 0:100) to provide the title compound as a yellow solid (195 mg, 60%): MS (DCI/NH$_3$) m/z 408 (M+H)$^+$.

Example 66C 6-(Hexahydropyrrolo[3,4-c]pyrrol-2-yl)-9-oxa-1-azaanthracen-10-one hydrochloride A solution of the product of Example 66B (66 mg, 0.16 mmol) in EtOAc (5 mL) was treated with 4N HCl/dioxane (1 mL, 4 mmol), and the resulting orange mixture was stirred for 3 h at room temperature. The mixture was concentrated, and the residue was crystallized from 95% EtOH (25 mL) to provide the title salt as a bright yellow solid (29 mg, 50%): $^1$H NMR (300 MHz, CD$_3$OD) δ ppm 3.15-3.35 (m, 4H), 3.36-3.49 (m, 2H), 3.50-3.71 (m, 4H), 7.41 (s, 1H), 7.41-7.49 (m, 1H), 7.56 (dd, J=8, 5 Hz, 1H), 7.59-7.70 (m, 1H), 8.62-8.87 ppm (m, 2H); MS (DCI/NH$_3$) m/z 308 (M+H)$^+$; Anal. Calc. For C$_{18}$H$_{17}$N$_3$O$_2$.HCl.H$_2$O: C, 62.55; H, 5.31; N, 12.16. Found: C, 62.44; H, 5.19; N, 11.93.

Example 67

6-(5-Methyl-hexahydropyrrolo[3,4-c]pyrrol-2-yl)-9-oxa-1-azaanthracen-10-one dihydrochloride The product of Example 66B (70 mg, 0.17 mmol) was combined with 37% formalin (200 μL) and formic acid (4 mL) and the red solution was warmed to 100° C. for 2 h. The mixture was cooled and concentrated under vacuum, and the residue was purified by preparative HPLC [30×100 mm Xterra® RP$_{18}$ column eluting with MeCN-0.1 M NH$_4$HCO$_3$ (pH 10) buffer (5:95-95:5) over 23 min] to provide the free base of the title compound as a bright yellow solid (24 mg, 30%). This was taken up in EtOAc (3 mL) and treated with 4N HCl/dioxane (0.1 mL). The mixture was concentrated under vacuum, and the residue was stirred with fresh ethyl acetate for 20 h, then filtered and dried under vacuum to provide the title salt as a yellow-orange solid: $^1$H NMR (300 MHz, CD$_3$OD) δ ppm 2.94 and 2.98 (s, epimeric NMe, 3H), 3.01-3.08 (m, 1H), 3.12-3.26 (m, 2H), 3.33-3.54 (m, 3H), 3.54-3.79 (m, J=15, 9 Hz, 3H), 3.88-4.12 (m, 1H), 7.38-7.51 (m, 1H), 7.47-7.53 (m, J=2, 2 Hz, 1H), 7.56 (dd, J=8, 5 Hz, 1H), 7.56-7.71 (m, 1H), 8.59-8.87 (m, 2H); MS (DCI/NH$_3$) m/z 322 (M+H)$^+$; Anal. Calc. for C$_{19}$H$_{19}$N$_3$O$_2$.2HCl: C, 57.88; H, 5.37; N, 10.66. Found: C, 57.53; H, 5.29; N, 10.44.

Example 68

Determination of Biological Activity

To determine the effectiveness of representative compounds of this invention as α7 nAChRs, the compounds of the invention were evaluated according to the [$^3$H]-methyllycaconitine (MLA) binding assay and considering the [$^3$H]-cytisine binding assay, which were performed as described below.

[$^3$H]-Cytisine Binding

Binding conditions were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 μg of protein and 0.75 nM [$^3$H]-cytisine (30 C$_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (–)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 μL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/1+[Ligand]/K$_D$].

[$^3$H]-Methyllycaconitine (MLA) binding

Binding conditions were similar to those for [$^3$H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM CaCl$_2$, 2 mM MgCl$_2$, and 50 mM Tris-Cl, pH 7.4, 22° C.). Samples containing 100-200 μg of protein, 5 nM [3H]-MLA (25 C$_i$/mmol; Perkin Elmer/NEN Life Science Products, Boston, Mass.) and 0.1% bovine serum albumin (BSA, Millipore, Bedford, Mass.) were incubated in a final volume of 500 μL for 60 minutes at 22° C. Seven log-dilution concentrations of each compound were tested in duplicate. Non-specific binding was determined in the presence of 10 μM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS.

Packard MicroScint-20® scintillation cocktail (40 μL) was added to each well and radioactivity was determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/1+[Ligand]/K_D]$.

Compounds of the invention had $K_i$ values of from about 1 nanomolar to about 10 micromolar when tested by the [$^3$H]-MLA assay, many having a $K_i$ of less than 1 micromolar. [$^3$H]-Cytisine binding values of compounds of the invention ranged from about 50 nanomolar to at least 100 micromolar. The determination of preferred compounds typically considered the $K_i$ value as measured by MLA assay in view of the $K_i$ value as measured by [$^3$H]-cytisine binding, such that in the formula $D=K_i^3{}_{H\text{-}cytisine}/K_{i\,MLA}$, D is about 50. Preferred compounds typically exhibited greater potency at α7 receptors compared to α4β2 receptors.

Compounds of the invention are α7 nAChRs ligands that modulate function of α7 nAChRs by altering the activity of the receptor. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula (I):

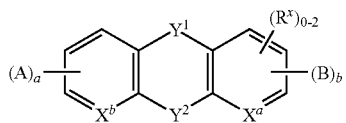

(I)

or a pharmaceutically acceptable salt or amide thereof, wherein:

A and/or B are
a group of formula (g):

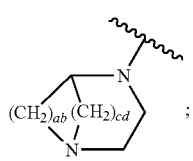

(g)

$X^a$ and $X^b$ are each independently C(H);
$Y^1$ is S, S(O), or S(O)$_2$;
$Y^2$ is a bond;
$R^x$ is independently selected at each occurrence from the group consisting of halogen, alkoxy, amino, alkylamino, dialkylamino, acylamino, dialkylaminoalkyl, and cyano;
a is 0 or 1;
b is 0 or 1; provided that when one of a and b is 0, the other is 1; and
ab is 2 or 3, and cd is 1 or 2.

2. The compound according to claim 1, wherein the group of formula (g) is selected from the group consisting of:

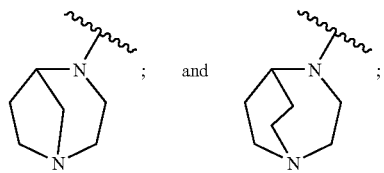

and enantiomers thereof.

3. The compound according to claim 1, selected from the group consisting of:

3,7-bis[(3S)-1-azabicyclo[2.2.2]octan-3-yloxy]-dibenzothiophene;
2-[(1S,5S)-3,6-diazabicyclo[3.2.0]heptan-3-yl]-dibenzothiophene-5,5-dioxide;
3,7-bis[3,7-diazabicyclo[3.3.0]octan-3-yl]-dibenzothiophene-5,5-dioxide;
3,7-bis[7-methyl-3,7-diazabicyclo[3.3.0]octan-3-yl]-dibenzothiophene-5,5-dioxide;
3-[3,7-diazabicyclo[3.3.0]octan-3-yl]-dibenzothiophene-5,5-dioxide;
3-[7-methyl-3,7-diazabicyclo[3.3.0]octan-3-yl]-dibenzothiophene-5,5-dioxide;
3-amino-7-[3,7-diazabicyclo[3.3.0]octan-3-yl]-dibenzothiophene-5,5-dioxide;
2,7-bis-[3,7-diazabicyclo[3.3.0]octan-3-yl]-dibenzothiophene-5,5-dioxide;
1-(5,5-dioxo-5H-5λ$^6$-dibenzothiophen-3-yl)-4-methylpiperazine;
(1S,5S)-3-(5,5-dioxo-5H-5λ$^6$-dibenzothiophen-3-yl)-3,6-diazabicyclo[3.2.0]heptane;
(1S,5S)-3-(5,5-dioxo-5H-5λ$^6$-dibenzothiophen-3-yl)-6-methyl-3,6-diazabicyclo[3.2.0]heptane; and
4-(5,5-dioxo-5H-5λ$^6$-dibenzothiophen-3-yl)-1,4-diazabicyclo[3.2.2]nonane.

4. A pharmaceutical composition comprising a therapeutically effective amount of a compound of claim 1 in combination with a pharmaceutically acceptable carrier.

* * * * *